(12) United States Patent
Zivkovic et al.

(10) Patent No.: US 12,055,553 B2
(45) Date of Patent: Aug. 6, 2024

(54) METHOD FOR DIAGNOSING RISK FOR INFLAMMATORY DISEASE THROUGH GLYCAN PROFILING

(71) Applicant: The Regents of the University of California, Oakland, CA (US)

(72) Inventors: Angela Zivkovic, Saint Helena, CA (US); Carlito B. Lebrilla, Davis, CA (US); Emanual Maverakis, Folsom, CA (US)

(73) Assignee: The Regents of the University of California, Oakland, CA (US)

( * ) Notice: Subject to any disclaimer, the term of this patent is extended or adjusted under 35 U.S.C. 154(b) by 1055 days.

(21) Appl. No.: 16/491,541

(22) PCT Filed: Mar. 9, 2018

(86) PCT No.: PCT/US2018/021788
§ 371 (c)(1),
(2) Date: Sep. 5, 2019

(87) PCT Pub. No.: WO2018/165574
PCT Pub. Date: Sep. 13, 2018

(65) Prior Publication Data
US 2021/0132089 A1 May 6, 2021

Related U.S. Application Data

(60) Provisional application No. 62/469,839, filed on Mar. 10, 2017.

(51) Int. Cl.
*G01N 33/92* (2006.01)
*A61K 31/7004* (2006.01)
*A61K 31/7008* (2006.01)

(52) U.S. Cl.
CPC ......... *G01N 33/92* (2013.01); *A61K 31/7004* (2013.01); *A61K 31/7008* (2013.01); *G01N 2333/775* (2013.01); *G01N 2333/81* (2013.01); *G01N 2400/00* (2013.01); *G01N 2800/7095* (2013.01)

(58) Field of Classification Search
CPC .. A61K 31/01; A61K 31/501; A61K 31/7004; A61K 31/7008; A61K 36/48; A61K 36/899; A61K 45/06; A61K 38/1709; A61K 38/1774; G01N 33/92; G01N 33/53
USPC ..................................................... 514/62, 33
See application file for complete search history.

(56) References Cited

U.S. PATENT DOCUMENTS

| 6,271,213 B1 * | 8/2001 | Henderson ........... A61K 31/726 514/53 |
| 2004/0234631 A1 | 11/2004 | Hoie |
| 2017/0312338 A1 | 11/2017 | Rodriguez Oquendo |

FOREIGN PATENT DOCUMENTS

| WO | 2001/075170 A1 | 10/2001 | |
| WO | 2007/132291 A2 | 11/2007 | |
| WO | 2015/105883 A1 | 7/2015 | |
| WO | WO 2015/105883 * | 7/2015 | ............. G01N 33/92 |
| WO | WO 2015/105883 A1 * | 7/2015 | ............. G01N 33/53 |

OTHER PUBLICATIONS

Krishnan et al., Journal of Proteome, 2015, 14, 5109-5118.*
Krishnan, S. et al.; "Combined High-Density Lipoprotein Proteomic and Glycomis Profiles in Patients at Risk for coronary Artery Disease"; *Journal of Proteome Research*; vol. 14; Nov. 4, 2015; pp. 5109-5118.
International Search Report and Written Opinion in PCT/US2018/021788 mailed May 30, 2018; 11 pages.
Huang, J. et al.; "Glycomic Analysis of High Density Lipoprotein Shows a Highly Sialylated Particle"; *Journal of Proteome Research*; vol. 13, No. 2; Jan. 13, 2014; pp. 681-691.
Krishnan, S. et al.; "HDL Glycoprotein composition and Site-Specific Glycosylation Differentiates Between Clinical Groups and Affects IL-6 Secretion in Lipopolysaccharide-Stimulated Monocytes"; *Scientific Reports*; vol. 7, No. 43728; Mar. 13, 2017; pp. 1-15.
Savinova, O.V. et al.; "Reduced Apolipoprotein Glycosylation in Patients with the Metabolic Syndrome"; *PLoS One*; vol. 9, No. 8; Aug. 12, 2014; pp. 1-9.
Tang, X. et al.; "Quantitative glycoproteomics of high-density lipoproteins"; *RSC Advances*; vol. 12; 2022; pp. 18450-18456.

* cited by examiner

*Primary Examiner* — Yih-Horng Shiao
(74) *Attorney, Agent, or Firm* — Kilpatrick Townsend and Stockton LLP

(57) ABSTRACT

Methods of detecting altered HDL functionality as well as adjusting HDL functionality are described.

24 Claims, 28 Drawing Sheets

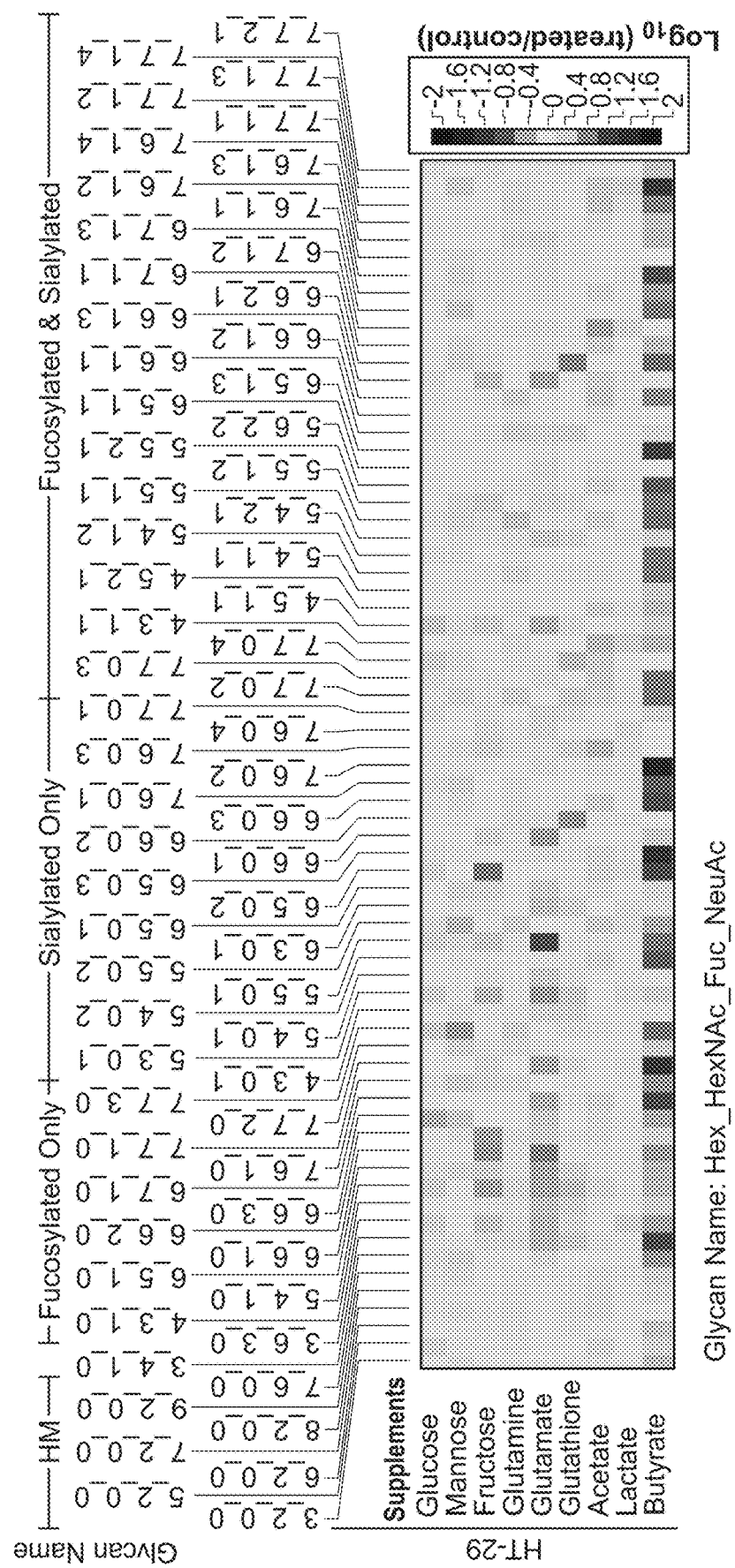
FIG. 15A (Cont. 1)

FIG. 17B (Cont. 1)

Table 3: Percent change in abundances of cell surface glycans on Caco-2 and HT-29 after addition of supplements. Columns are grouped according to glycan type. Significant changes (control to treated) are indicated by colored arrows.

| | HM[a] | | C/H | | C/H-F | | C/H-S | | C/H-FS | |
|---|---|---|---|---|---|---|---|---|---|---|
| | Caco-2 | HT-29 | Caco-2 | HT-29 | Caco-2 | HT-29 | Caco-2 | HT-29 | Caco-2 | HT-29 |
| Glutamine 10mM | ↑507%[b] | ↑39.8% | ↑467% | ↑64.2% | ↑25.5% | ↑27.4% | ↓25.7% | ↓2.6% | ↓47.1% | ↓15.0% |
| Glutathione 2mM | ↑0.1% | ↑37.1% | ↑9.1% | ↓10.0% | ↑1.5% | ↓6.1% | ↓21.3% | ↓0.5% | ↑2.6% | ↑1.8% |
| Glutamate 2mM | ↓12.2% | ↓2.9% | ↓12.9% | ↓56.6% | ↓0.4% | ↓44.4% | ↓10.1% | ↑5.7% | ↑2.3% | ↑16.3% |
| Fructose 50mM | ↑511% | ↑8.3% | ↑672% | ↓42.3% | ↑28.3% | ↓32.7% | ↓29.6% | ↑3.2% | ↓49.7% | ↑11.8% |
| Lactose 70mg/mL | ↑6.3% | | ↑26.8% | | ↓20.5% | | ↑37.7% | | ↓0.6% | |
| Glucose 25mM | ↓5.8% | ↓4.5% | ↑5.5% | ↓20.0 | ↓0.7% | ↓13.9% | ↑1.1% | ↑5.1% | ND | ↑6.7% |
| Mannose 25mM | ↓8.7% | ↑53.6% | ↓17.6% | ↓13.9% | ↑16.9 | ↓12.1% | ↓1.7% | ↑10.7 | ↓3.3% | ↓0.3% |
| Galactose | ↑125% | | ↑88.8% | | ↓20.4% | | ↓12.3% | | ↓28.3% | |

FIG. 19

| | HM[a] | | C/H | | C/H-F | | C/H-S | | C/H-FS | |
|---|---|---|---|---|---|---|---|---|---|---|
| | Caco-2 | HT-29 | Caco-2 | HT-29 | Caco-2 | HT-29 | Caco-2 | HT-29 | Caco-2 | HT-29 |
| Fucose 25mM | ↓50.9% | | ↓91.0% | | ↑91.0% | | ↓39.7% | | ↑7.4% | |
| GlcNAc 25mM | ↓0.7% | | ↑24.8% | | ↑61.2% | | ↓53.9% | | ↓9.4% | |
| GalNAc 25mM | ↑17.% | | ↑234% | | ↑120% | | ↓31.8% | | ↓27.5% | |
| Ac5-Sia 10mM | ↑4.2% | | ↑8.0% | | ↑11.7% | | ↓12.8% | | ↓3.5% | |
| Sialic acid 25mM | ↓97.1% | ↑162% | ↓100% | ↑103% | ↓74.7% | ↓9.3% | ↑698% | ↑120% | ↓72.3% | ↓71.0% |
| Acetic acid 50mM | ↓82.1% | ↓353% | ↑731% | ↑98.8% | ↓42.9% | ↓32.1% | ↑655% | ↑117% | ↓70.3% | ↓75.4% |
| Acetic acid 10mM | ↑65.8% | ↑73.3% | ↑159% | ↑59.7% | ↑60.0% | ↑35.4% | ↓8.8% | ↓11.7% | ↓26.4% | ↓2.6% |
| Lactic acid 10mM | ↑25.3% | ↓2.9% | ↑103% | ↑18.8% | ↑41.6% | ↑4.6% | ↓3.3% | ↓5.3% | ↓17.7% | ↓5.0% |
| Butyric acid 10mM | ↑27.1% | ↑171% | ↑54.4% | ↑66.7% | ↑72.3% | ↑262% | ↓31.9% | ↓39.7% | ↓12.1% | ↓28.6% |

[a]HM = High mannose; C = Complex; H = Hybrid; F = Fucosylated; S = Sialylated; ND = No change detected
[b]Red and blue arrows indicate statistically significant (two-tailed, unpaired Student's t-test, $p < 0.05$) increases and decreases in relative abundances compared to untreated controls, respectively.

FIG. 19 (Cont.)

METHOD FOR DIAGNOSING RISK FOR INFLAMMATORY DISEASE THROUGH GLYCAN PROFILING

CROSS-REFERENCE TO RELATED PATENT APPLICATIONS

The present patent application is a US National Phase Application Under 371 of PCT/US2018/021788 filed Mar. 9, 2018, which claims benefit of priority to U.S. Provisional Patent Application No. 62/469,839, filed Mar. 10, 2017, which is incorporated by reference for all purposes.

STATEMENT AS TO RIGHTS TO INVENTIONS MADE UNDER FEDERALLY SPONSORED RESEARCH AND DEVELOPMENT

This invention was-made with government support under grant nos. DK070005, DK075004, DK085153, GM049077, OD008752, and TRO00002 awarded by the National Institutes of Health. The government has certain rights in the invention.

BACKGROUND OF THE INVENTION

High density lipoproteins (HDL) are primarily known for their atheroprotective functions, particularly reverse cholesterol transport, reducing oxidation of LDL, and protecting the endothelial wall [Toth, P. P. et al., *Journal of clinical lipidology* 7, 484-525, doi:10.10165, j.jacl.2013.08.001 (2013)]. In the past ten years, additional functions of HDL have been discovered, including those related to inflammation [Zhu, X. & Parks, J S., *Annu Rev Nutr* 32, 161-182, doi:10.1146/annurev-Nutr-071811-150709 (2012)] and immune function [Feingold, K. R. & Grunfeld, C., *J Lipid Res* 52, 1-3, doi:10.1194/jlr.E012138 (2011)]. A recent analysis of multiple genome-wide association studies of inflammatory diseases comprising a total of over 200,000 individuals found multiple shared risk loci between HDL and immune pathways [Andreassen, O. A. et al., *PloS one* 10, e0123057, doi:10.1371/journal.pone.0123057 (2015)].

HDL has three known pathways by which it interacts with the immune system. 1). By various mechanisms, HDL can protect against septic shock [van Leeuwen, H. J. et al., *Neth J Med* 59, 102-110, doi:S0300297701001449[pii](2001)]. Specifically, it can bind and neutralize lipopolysaccharide (LPS) produced by gram-negative bacteria for subsequent transfer to and degradation by the liver [Levine, D. M. et al., *Proc Natl Acad Sci USA* 90, 12040-12044 (1993); Munford, R. S. et al., *J Clin Invest* 70, 877-888 (1982)]. It can also protect against-septic shock by transferring LPS to Low Density Lipoproteins (LDL). 2) HDL particles can deplete cholesterol from immune cells, there by reducing lipid raft-associated signalling [Yin, K. et al., *J Atheroscler Thromb* 19, 823-836(2012)]. 3) HDL particles can have a direct anti-inflamatory effect on immune cells via the transcriptional down-regulation of cytokines [De Nardo, D. et al., *Nature Immunology* 15, 152-160, doi:10.1038/ni.2784 (2014). Importantly, for each of these studies HDL was prepared from pooled serum samples; thus, the existence of patient-to-patient variation in the immunodulatory properties of HDL is currently unknown. Given the wide inter-individual compositional variation of HDL, identifying the components of HDL that correlate with its effect on immune response is useful.

BRIEF SUMMARY OF THE INVENTION

In some embodiments, methods of determining high density lipoprotein (HDL) functional capacity in a human ae provided. In some embodiments, the method comprises
   a. obtaining an HDL sample from a human;
   b. detecting in the sample levels of glycosylation in the HDL sample.

In some embodiments, the detecting comprises detecting levels of glycosylation of one or more specific proteins in the HDL sample. In some embodiments, the detecting comprises detecting comprises detecting a level of at least one glycosylation type for all proteins in the HDL sample (i.e., levels of particular or general glycosylation across all protein in HDL sample).

In some embodiments, the method further comprises: c. comparing the level of the glycosylation (e.g., generally or of specific proteins) to a control value, thereby determining HDL functional capacity in the human. In some embodiments, the control value is:
   a value indicating the level of glycosylation(e.g., generally or for each specific protein) detected in a healthy individual; or
   a value indicating the level of glycosylation(e.g., generally or for each specific protein) detected in an individual having functional HDL; or
   a value indicating the level of glycosylation(e.g., generally or for each specific protein) detected in an individual having dysfunctional HDL.

In some embodiments, the detecting comprises detecting the level of glycosylation of:
   ApoC-III,
   Mono-sialylated ApoC-III,
   ApoC-III_74_2221,
   Non-sialylated alpha-2HS-glycoprotein (A2HSG),
   Di-sialylated A2HSG,
   A2HSG_O_346_2200,
   A2SG_O_176_5402,
   alpha-1-antitrypsin (A1AT),
   A1AT_70_5402,
   A1AT_271_5402,
   A1AT_70_5412,
   A1AT_107_5412, or
   A1AT_271_5412, In some embodiments, the detecting comprises detecting the level of glycosylation of:
   i. ApoC-III, and
   mono-sialic ApoC-III, and
   ApoC-III_74_2221; or
   ii. A1AT, and
   di-sialic A1AT (e.g., glycans 5402 and 5412), or
   iii. non-sialic A2HSG, and
   A2HSG_O_346_2200, and
   di-sialic A2HSG, and
   A2HSG_176_5402.

In some embodiments, the HDL functional capacity is the capacity to affect an inflammatory response. In some embodiments the HDL functional capacity is the level of pro-inflammatory HDL or HDL lacking in anti-inflammatory capacity in the sample.

In some embodiments, the method further comprises:
   d. administering an effective amount of (e.g., dietary) monosaccharides or other sugars and/or altering dietary pattern, or other dietary/pharmaceutical/other treatments that alter the expression or activity of glycosyltransferase genes and/or otherwise affect the glycosylation of HDL proteins, to the diagnosed patient.

In-some embodiments, the monosaccharides comprise at least one of the following in an amount sufficient to alter the level of glycosylation for at least one of the specific proteins in the human: galactose, fructose, fucose, or N-acetyl glucosamine. In some embodiments the sugars administered include, for example, any type or combination of monosaccharides including trioses, tetroses, pentoses, hexoses, heptoses, amino sugars (e.g. N-acetylglucosamine, galactosamine, and glucosamine). The combinations of sugars can be administered as mixtures of monosaccharides and/or dietary sugars in the form of disaccharides and polysaccharides.

In some embodiments, the detecting comprises binding the specific protein in the sample with a binding reagent that specifically binds the specific protein or an oligosaccharide thereon. In some embodiments, the binding agent is a lectin or an antibody.

In some embodiments, the detecting comprises mass spectrometry or liquid chromatography.

Also provided are methods of improving high density lipoprotein (HDL) function in a human in need thereof. In some embodiments, the method comprises administering a sufficient, amount of monosaccharides or other sugars to improve HDL function in the human, wherein before the administrating the human has HDLs having levels of glycosylation (generally or of one or more specific proteins) indicative of reduced HDL function compared to healthy humans and wherein after the administrating the human has HDLs having levels of glycosylation (generally or of the one or more specific proteins) indicative of improved HDL function compared to before the administering.

In some embodiments, be monosaccharides comprise at least or more of galactose, fructose, fucose, or N-acetyl glucosamine. In some embodiments, the sugars administered include, for example, any type or combination of monosaccharides including trioses, tetroses, pentoses, hexoses, heptoses, amino sugars (e.g., N-acetylglucosamine, galactosamine, and glucosamine). The combinations of sugars can be administered as mixtures of monosaccharides and/or dietary sugars in the form of disaccharides and polysaccharides.

In some embodiments, before the administering, an HDL sample is obtained from the human and the level of glycosylation of HDL protein (e.g. at least one or more of the specific proteins) is detected.

In some embodiments, after the administering, an HDL sample is obtained from the human and the level of glycosylation of HDL protein (e.g., at least one or more of the specific proteins) is detected.

Also provided are reaction mixtures comprising:
a human sample enriched for high density lipoproteins (HDLs); and
one or more reagent specific for (i.e., that binds or specifically binds) a specific HDL protein or glycan in the sample.

In some embodiments, the specific HDL protein is selected from ApoC-III,
Mono-sialylated ApoC-III,
ApoC-III_74_2221,
Non-sialylated-alpha-2HS-glycoprotein (A2HSG),
Di-sialylated A2HSG,
A2HSG_O_346_2200,
A2HSG_176_5402,
alpha-1-antitrypsin (A1AT),
A1AT_70_5402,
A1AT_271_5402,
A1AT_70_5412,
A1AT_107_5412, or
A1AT_271_5412.

In some embodiments, the reaction mixture comprises:
i. a reagent that specifically binds ApoC-III, and
a reagent that specifically binds mono-sialic ApoC-III, and
a reagent that specifically binds ApoC-III_74_2221; or
ii. a reagent that specifically binds A1AT, and
a reagent that specifically binds di-sialic A1AT (e.g., glycans 5402 and 5412);
iii. a reagent that specifically binds non-sialic A2HSG, and
a reagent that specifically binds A2HSG_O_346_2200, and
a reagent that specifically binds di-sialic A2HSG, and
a reagent that specifically binds A2HSG_176_5402.

Other embodiments will be apparent from review of the remainder of this application.

BRIEF DESCRIPTION OF THE DRAWINGS

FIG. 6A-C. Chromatogram of identified cell surface glycans released from Caco-2. Profiles are shown for (A) Caco-2 untreated, (B) Caco-2 after addition of glutamine, and (C) Caco-2 grown under low pH with addition of acetic acid. Monosaccharide symbols follow the SNFG (Symbol Nomenclature for Glycans) system details at NCBI (Varki, A., Cummings, R. D., et al, 2015).

FIG. 19. Percent change in abundances of cell surface glycans on Caco-2 and HT-29 after addition of supplements. Columns are grouped according to glycan type. Significant changes (control to treated) are indicated by colored arrows.

DETAILED DESCRIPTION OF THE INVENTION

Figure 1:
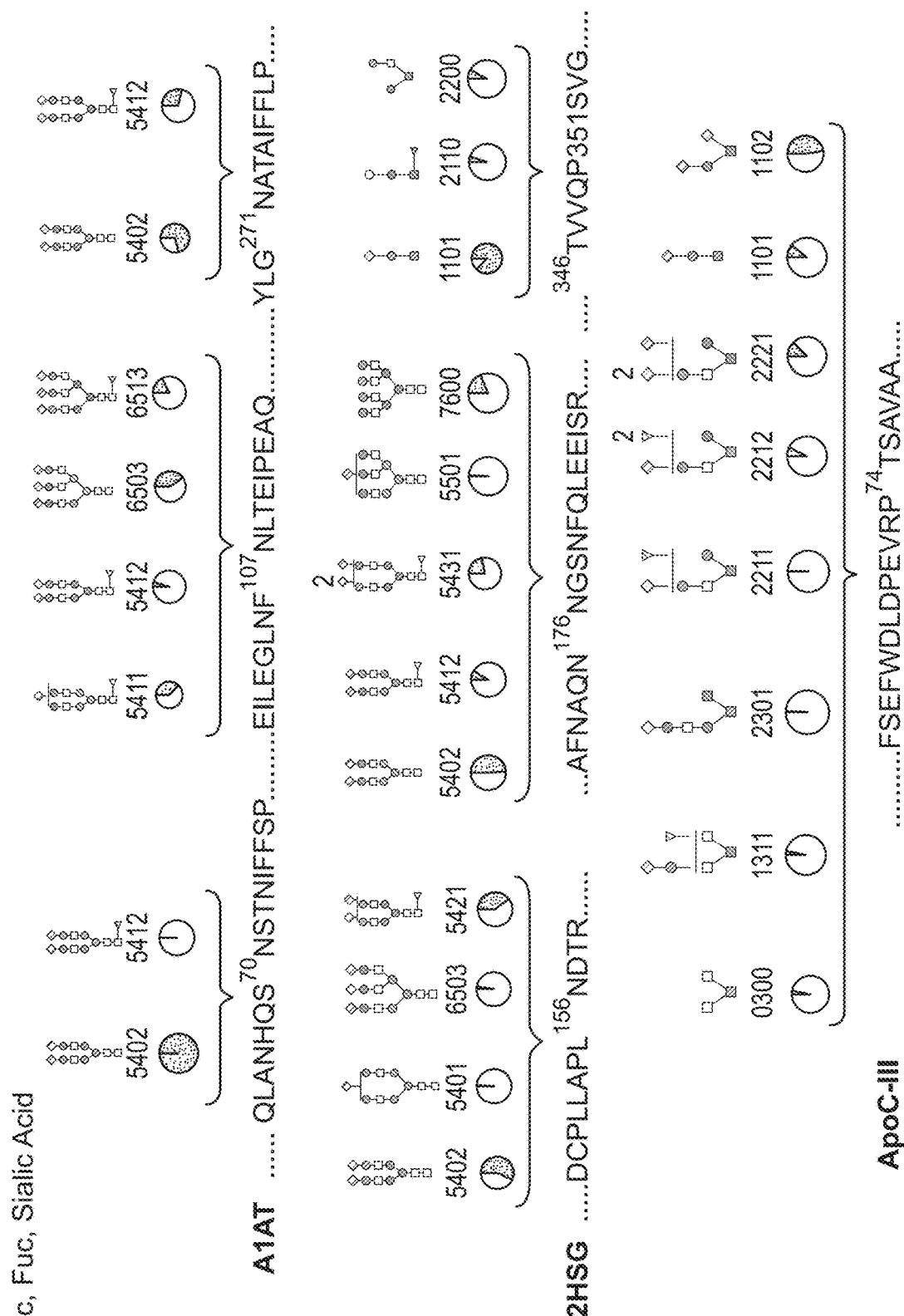
FIG. 1. Protein backbone and putative structures for N and O-glycopeptides including their relative abundances within the site. There were three N-linked glycosylated sites in A1AT, 2 N-linked and 2 O-inked glycosylation sites in A2HSG while ApoC-III bad only one site populated with O-linked glycans. The modified amino acid number is shown in red and the residue modified with O-glycans is colored green. The glycan monosaccharides annotation includes (blue ■) N-acetylglucosamine (HexNAc), (green •) mannose, (yellow •) galactose, (○) hexose, (red ▲) fucose, (purple ♦) N-acetyl neuraminic acid. The four number glycan code represents the number of hexoses, HexNAc, fucose, and N-acetyl neuraminic acid residues in that order. The pie charts shows the relative abundances of different glycans within a given protein standard site.

The inventors have discovered that the level of glycosylation of high density lipoproteins (HDLs), e.g., both general glycosylation of proteins generally in HDL and particularly site-specific glycosylation of HDLs, are indicative of HDL function. For example, the Inventors have shown that the level of site-specific glycosylation of certain HDL proteins (and also changes in overall glycosylation such as overall extent of sialylation or fucosylation or galactosylation or level of N-acetylglucosamine, or the degree of branching, or the ratios of glycan compositions on the overall N- and O-glycan of the total glycoproteome of HDL) is associated with immunomodulatory function of HDLs. Accordingly, the detection of site-specific glycosylation or overall N- and/or O-glycan profiles in glycoproteins can be used to assess HDL function, including immunomodulatory function, in humans.

Further, the present application also describes that administration of monosaccharides to humans having impaired HDL function can result in improved HDL function. This is based in part on the discovery that monocytes incubated with sugars had an altered HDL glycosylation that reflected a healthier glycosylation profile.

HDLs have the ability to regulate immune responses. For example, HDL particles can have an anti-inflammatory effect on immune cells, e.g., by down-regulation of cytokine expression. In the methods described herein, one can detect levels of glycosylation of one or more specific proteins in HDL and optionally can use the levels to predict HDL functional capacity. While not required for the methods described herein, it will be appreciated that one can measure immunomodulatory activity of immune cells in several ways. For instance, the examples describe an assay to measure an HDL's effect on immune cells by contacting the HDLs to monocytes stimulated with lipopolysaccharide and then measuring the effect of the contacting on IL-6 expression. In other embodiments, other immune cells (e.g., macrophages, dendritic cells, B cells, T cells) can be assayed. Immune cells assayed can be primary cells or cell lines. Moreover, while IL-6 expression was a measured output in the examples below, it will be appreciated that other sorts of immunomodulation can be measured in immune cells. For example, one can instead or in conjunction measure levels of other cytokines, stimulation of specific inflammatory signaling pathways such as NFκB pathway stimulation, expression of genes or proteins involved in inflammation pathways, examine morphological or other physiological or structural changes to cells such as transformation to other cell types or differentiation into other phenotypes. In addition, in the example described herein bacterial lipopolysaccharide was used to stimulate the monocytes to elicit measurable levels of IL-6 in the culture media, however, other stimulants can be used as well for example, citrullinated fibrinogen, oxidized lipids, advanced glycation end products, or other stimulants that elicit the secretion of other cytokines or the induction of other inflammatory signaling pathways.

The methods described herein allow for obtaining and assaying HDL samples from an individual(e.g., from a human or non-human animal). HDLS can be isolated from for Example, whole blood or serum. Serum lipoproteins comprise a heterogeneous population of lipid-protein complexes that can be grouped into broad classes, very low (VLDL), low (LDL) and high (HDL) density, based on differences in particle density related to lipid and protein content. VLDL and LDL are composed of predominately lipid, while high density lipoproteins have a higher content of protein (about 50%). In some embodiments, the density of LDL is between 1.006-1.063 g/ml while that of HDL particles is 1.063-1.25 g/ml. In some embodiments, HDL are identified by their size range of 5-15 nm in size and/or electrophoretic mobility as measured and separated by a variety of other techniques including FPLC/size exclusion chromatography, get electrophoresis, chemical precipitation, and a variety of combined approaches combining density, size, or structure/charge.

Classical methods to separate HDL from VLDL and LDL employ sequential density ultracentrifugation using potassium bromide salt solutions prepared with densities in the range of each lipoprotein class. Alternative methods for isolation of HDLs include, but are not limited to those described in, e.g., US Patent Publication Nos, 2015/0331000 or 2013/0231461.

The level of glycosylation of a "specific protein" refers to the amount or concentration of a glycosylation (e.g. either total glycosylation the specific protein or a particular glycan at a particular site) on a particular specific protein. "Specific protein" refers to proteins having the same amino acid sequence. HDs are a mixture of different specific proteins that are fractionated together in view of their common physical properties (e.g., density, size, and/or charge). Specific proteins making up HDLs include, but are not limited to, those in Table 1 as well as for example, ApoE, ApoC-II, ApoA-II, ApoC-I, ApoJ, ApoD, ApoM, PON1, or SAA4.

Table 1 below provides a listing of specific proteins, and in some cases specific glycosylation types and sites that were identified as differing in HDL populations having normal or reduced anti-inflammatory function. Some of the entries in Table 1 include the specific site and glycan type. For example, "A1AT_70_5402" refers to the protein A1AT (alpha-1-antitrypsin), amino acid at position 70, and the glycan type of "5402." The latter numbering system can be decoded as follows: Glycan composition was designated by the number of hexose (Hex) residues, N-acetylhexosamine (HexNAc) residues, fucose (Fuc) residues, and N-acetylneuraminic acid-(NeuAc) residues. Thus, the glycan is 5 Hex, 4 HexNAc, 0 Fuc, and 2 NeuAc.

TABLE 1

| Marker/Glycoprotein/Glycan | Increased in Dysfunctional/Pro-inflammatory HDL | Decreased in Dysfunctional/Pro-inflammatory HDL |
| --- | --- | --- |
| ApoC-III | X | |
| % Mono-sialylated ApoC-III | | X |
| ApoC-III_74_2221 | | X |
| % Non-sialylated A2HSG | X | |
| % Di-sialylated A2HSG | | X |
| A2HSG_O_346_2200 | X | |
| A2HSG_176_5402 | | X |
| A1AT | | X |
| A1AT_70_5402 | X | |
| A1AT_271_5402 | X | |
| A1AT_70_5412 | X | |
| A1AT_107_5412 | X | |
| A1AT_271_5412 | X | |

In some embodiments, the level of glycosylation at more than one specific HDL protein is detected. Optionally the combination of levels can be used to tore accurately predict HDL immuno function. For example, in some embodiments, 2, 3, 4, or more of the proteins in Table 1 and/or selected from ApoE, ApoC-II, ApoA-II, ApoC-I, ApoJ, ApoD, ApoM, PON1, or SAA4 are assayed for a leveled of glycosylation. Additional specific HDL glycoproteins are described in, e.g., Vaisar, *Curr Vasc Pharmacol.* 2012 July;

10(4): 410-421. In a non-limiting example, in some embodiments, the methods comprise detection pf the glycosylation level of (see also FIG. 7):
  i. ApoC-III, and
    mono-sialic ApoC-III, and
    ApoC-III_74_2221; or
  i. A1AT, and
    di-sialic A1AT (e.g., glycans 5402 and 5412); or
  iii. non-sialic A2HSG, and
    A2HSG_346_2200, and
    di-sialic A2HSG, and
    A2HSG_176_5402.

Alternatively, the level of a specific type of glycosylation, or of glycosylation in general, across different HDL proteins can be detected and optionally correlated with HDL functionality.

Glycosylation of HDL proteins can be detected in any way available. In some embodiments, mas spectrometry, capillary electrophoresis, or liquid chromatography is used to detect glycosylation. In other embodiments, a binding reagent that specifically binds a specific HDL-protein, or glycan is used to bind and quantify glycosylation of a specific protein. Exemplary binding reagents can include, for example, antibodies or lectins. Lectins bind specific glycans or classes of glycans and thus can be used to distinguish different types of glycosylation on a protein. In some embodiments, the simple can be applied to an array of lectins and/or antibodies and subsequently detected. Exemplary methods include those described in, e.g., Yan et al., Anal. Chem., 83 (22), 85094516 (2011). Other methods of detecting-glycosylation include those described in, e.g., U.S. Pat. Nos. 7,332,355 and 7,838,634 and 8,927,300.

In some embodiments, a reaction mixture is provided in which one or more HDLs or a sample enriched for HDLs is combined with one or more reagent that binds glycans, or specific glycosylated sites on specific HDLs. In some embodiments, the one or more reagent is linked to a solid support or is linked to s detectable label. Examples of detectable labels include, but are not limited to, biotin, enzymes(e.g., HRP), radioisotopes, chemiluminescent labels, or fluorescent labels. Exemplary solid supports can include but are not limited to beads or solid surfaces (e.g., plastic, polystyrene or other).

Once the sample(s) from the human subject have been analyzed as described above, a value index is generated based on the level of glycosylation at one more sites in the one or more specific proteins in the HDL sample. When two or more levels (e.g., glycosylation of different specific proteins or specific sites), the each level can be weighted and combined. Thus, in some embodiments, a teat value may be provided by (a) weighting the determined level of each level with a predefined coefficient, and (b) combining the weighted level to provide a test value. The combining step can be by straight addition or averaging (i.e., weighted equally), by a one or more predefined coefficients; or other statistical methods.

Once generated, the value from a sample can be compared to one or more threshold (control) value(s) to provide a prediction of HDL functionality (e.g., immunomodulatory function) in the sample and thus of the human from which the sample was obtained. In order to establish a threshold value for practicing the method a reference population of subjects can be used. In some embodiments, a population of healthy humans, i.e., having normal HDL levels, can be used. Optionally, the patients are of similar age or similar ethnic background. The status of the selected patients can be confirmed by well established, routinely employed methods including but not limited to general physical examination of the individuals and general review of their medical history. Alternatively, a population of humans having impaired HDL functionality can be used to generate a control value indicative of a particular HDL impairment. For example, in some embodiments, the humans can be selected for having metabolic syndrome, e.g., as described in more detail in the examples.

Furthermore, the selected group of individuals will generally be of sufficient size, such that the average value in the sample obtained from the group can be reasonably regarded as representative of a particular indication, for example indicative of impaired HDL functionality or not.

Once an average value is established based on the individual values found in each subject of the selected group, this average or median or representative value, or profile can be used as a threshold value. For example, a sample value different than(lower or higher depending on how the value is calculated) than the healthy threshold value or range can in some embodiments indicate a more than average likelihood of that be individual has impaired HDL functionality (e.g.; impaired HDL immunomodulatory functionality) whereas a sample value at or within a threshold value can indicate normal HDL functionality. In some embodiments, a standard deviation is also determined during the same process. In some cases, separate threshold values may be established for separately defined groups having distinct characteristics such as age, gender, or ethnic background.

In some embodiments, the sample is, compared to one or more reference or threshold values. In some embodiments, the sample value is deemed to reflect impaired functionality if it is at least 1, 2, 3, 4, 5, 10, 15, 20 or more standard deviations different than the healthy reference value subjects.

In some embodiments, a computer-based analysis program is used to translate the raw data generated by the detection methods described herein (e.g., the presence, absence, or amount of a given glycosylation) into a score of predictive value to a clinician. The score, as determined according to the methods above, can predict HDL functionality of a human patient.

Any of the comparison methods described herein may be totally or partially performed with a computer system including one or more processors, which can be configured to perform the steps. Thus, embodiments are directed to computer system configured to perform the steps of any of the methods-described herein, potentially with different components performing a respective step or a respective group of steps. Although presented as numbered steps, steps of methods herein can be performed at a same time or in a different order. Additionally, portions of these steps may be used with portions of other steps from other methods. Also, oil or portions of a step may be optional. Any of the steps of any of the methods can be performed with modules, circuits, or other means for performing these steps.

In some aspects of the present disclosure, a computer product is provided. The computer product can comprise a non-transitory computer readable medium storing a plurality of instructions that when executed determine a human subject's HDL functionality using the criteria described herein. In some embodiments, the instructions include receiving a set of determined glycosylation levels for one or more site on one or more specific HDL protein (e.g., as described herein) in a biological sample from the subject; comparing the set of determined glycosylation levels to a set of reference values for the sites on one or more specific HDL; scoring each glycosylation level as indicative of impaired or normal HDL functionality, wherein determination is impaired if the values differ (increased or decreased) from a healthy threshold value or range; and optionally determining the subject's risk of impaired HDL functionality by based on a calculation.

Any of the computer systems mentioned herein may utilize any suitable number of subsystems. Examples of such subsystems are shown in FIG. 1 in computer-apparatus 100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 1 are interconnected via a system bus 175. Additional subsystems such as a printer 174, keyboard 178, storage device(s) 179, monitor 176, which is coupled to display adapter 182, and others are shown. Peripherals and input/output (I/O) devices, which couple to I/O controller 171, can be connected to the computer system by any number of means known in the art, such as serial port 177. For example, serial port 177 or external interface 181 (e.g. Ethernet, Wi-Fi, etc.) can be used to connect computer system 100 to a wide area network such as the Internet, a mouse input device, or a scanner. The interconnection via system bus 175 allows the central processor 173 to communicate with each subsystem and to control the execution of instructions from system memory 172 or the storage device(s) 179 (e.g., a fixed disk, such as a hard drive or optical disk), as well as the exchange of information between subsystems. The system memory 172 and/or the storage device(s) 179 may embody a computer readable medium. Any of the data mentioned herein can be output from one component to another component and can be output to the user.

A computer system can include a plurality of the same components or subsystems, e.g., connected together by external interface 181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM); a read only memory (ROM), a magnetic medium, such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD or on entire computer system), and may be present on or within different computer products within a system or network. A computer system may include a monitor, printer, or other suitable display for providing any of the results mentioned herein to a user.

Also provided herein are methods of altering HDL functionality (e.g., the anti-inflammatory function of HDLs) in an individual by administration of a monosaccharide sugar to the individual. Exemplary monosaccharides that can be administered to an individual can include, but are not limited to, galactose, fructose, fucose, or N-acetyl glucosamine or a food or composition comprising a suitable amount of the monosaccharide (e.g., *spirulina*). In some embodiments, the individual to whom the monosaccharides is administered has reduced HDL functionality (e.g., has reduced anti-inflammatory activity compared to a healthy or normal or average human). For example, in some embodiments, the individual has been determined to have altered levels of HDL glycosylation as described herein compared to healthy individuals and the amount of the monosaccharide(s) is sufficient to change the level of HDL glycosylation to a level closer to a normal (healthy) level of glycosylation. In other embodiments, a altered diet can be recommended and implemented by the individual (e.g., from a high fat diet to a "Mediterranean"—like diet). In some embodiments, prebiotic or probiotic compositions are administered to the individual.

In some embodiments, the monosaccharides are administered in a pharmaceutical composition with a physiologically (i.e., pharmaceutically) acceptable carrier. The term "carrier" refers to a typically inert substance used as a diluent or vehicle for a diagnostic of therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there am a wide variety of suitable formulations of pharmaceutical compositions of the present invention (See, e.g., Remington's Pharmaceutical Sciences, 17$^{th}$ ed., 1989).

The presently described compositions can be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Dosage forms can be prepared for mucosal (e.g., nasal, sublingual, vaginal, buccal; or rectal), parenteral (e.g., subcutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms-suitable for parenteral administration to a patient; and sterile solids (e.g., crystalline or amorphous solids) that can be reconstituted to provide liquid dosage forms suitable for parenteral administration to a patient.

Injectable compositions can comprise a solution of the monosaccharides suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoprotein for enhanced stability, such as albumin, lipoprotein, globulin, etc. In some embodiments, normal buffered saline (135-150 mM NaCl) is used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc.

EXAMPLES

The following examples are offered to illustrate, but not to limit, the claimed invention.

Example 1

A goal of this study was to determine whether HDL glycoprotein composition affects HDL's immunomodulatory function. HDL were, purified from healthy controls (n–13), subjects with metabolic syndrome (MetS)(n–13), and diabetic hemodialysis (HD) patients (n=24). Concentrations of HDL-bound serum amyloid A (SAA), lipopolysaccharide binding protein (LBP), apolipoprotein A-I (ApoA-I), apolipoprotein C-III (ApoC-III), α-1-antitrypsin (A1AT), and α-2-HS-glycoprotein (A2HSG); and the site-specific glycovariations of ApoC-II, A1AT, and A2HSG were measured. Secretion of interleukin 6 (IL-6) in lipopolysaccharide-stimulated monocytes was used as a prototypical assay of HDL's immunomodulatory capacity. HDL from HD patients were enriched in SAA, LBP, ApoC-III, di-sialylated ApoC-III (ApoC-III$_2$) and desialylated A2HSG. HDL that increased IL-6 secretion were enriched in ApoC-III, di-sialylated glycans at multiple A1AT glycosylation sites and desialylated A2HSG, and depleted in mono-sialylated ApoC-III (ApoC-III$_1$). Subgroup analysis on HD patients who experienced an infectious hospitalization event within 60 days (HD+) (n=12), vs. those with no event (HD−) (n=12) showed that HDL from HD+ patients-were enriched in SAA but had lower levels of sialylation across glycoproteins. Our results demonstrate that HDL glycoprotein composition, including the site-specific glycosylation, differentiate between clinical groups, correlate with HDL's immunomodulatory capacity, and may be predictive of HDL's ability to protect from infection.

Our current understanding of the inter-individual variability in HDL's immunomodulatory effects is rudimentary and somewhat contradictory. For example, investigators have demonsrated at the HDL-associated proteins, apolipoprotein A-I (ApoA-I) [Umemoto, T, et al., Circ Res 112, 1345-1354, doi:10.1161/CIRCRESAHA.11 1.300581 (2013)], serum amyloid A (SAA) [Eklund, K. K. et al., Crit Rev Immunol 32, 335-348 (2012)], and ApoC-III [Grunfeld, C.& Feingold, K. R., J Lipid Res 49, 1605-1606, di:10.1194/jk.E80001]-JLR200 (2008)] have opposing immunomodulatory properties. ApoA-I suppresses cytokine release in a variety of cell types [De Nardo, D. et al., Nature Immunology 15, 152-460, doi:10.1038/ni.2784 (2014); Umemoto. T. et al., Circ Res 112, 1345-1354, doi:10.1161/CIRCRESAHA.111.300581 (2013)] whereas SAA simulates the release of cytokines and chemotaxis [Eklund, K. K. et al, Crit Rev Immunol 32, 335348 (2012)]. Also, it has been demonstrated that HDL loses its anti-inflammatory and anti-oxidant capacity in the setting of the acute phase response [Van Lenten B. J. et al., J Lipid Res 48, 2344-2353, doi:10.1194/jlr.M700138-JLR200(2007); Van Lenten, B. J. et al., J Clin Invest 96, 2758-2767, doi:10.1172/JCID18345 (1995)]. Likewise, it has been shown that HDL's anti-inflammatory capacity is reduced in metabolic diseases including type 2 diabetes and MetS (reviewed in [Kontush, A. & Chapman, M. J., Pharmacol Rev 58, 342-374, doi:$8/3/342[pii]10.1124/pr.58.3.1 (2006)]). Given these results, we hypothesize that the net immunomodulatory capacity of an individual's HDL will be dependent on their specific ADL composition.

However, correlating HDL composition with function is a daunting task because the highly complex HDL proteome has over 100 proteins, many of which are associated with cholesterol transport and lipid metabolism. How these proteins are also associated with the acute phase response; immunity, and inflammation is an area of active investigation[Vaisar, T. et al., J Clin Invest 117, 746-756, doi:10.1172/JC126206 (2007); Vaisar, T., Current vascular pharmacology 10, 410-421 (2012); Alwaili, K. et al., Biochim Biophys Acta 1821, 405-415, doi:10.1016/j.bbalip.2011.07.013 (2012)]. Another dimension of complexity is added by the fact that most of the HDL-associated proteins are glycosylated and the Individual structures of the decorating glycans will likely alter the Immunomodulatory properties of the proteins [Maverakis, E. et al., J Autoimmun 57, 1-13, doi: 10.1016/j.jaut.2014.12.002 (2015)]. To focus on the individual glycovariants of the HDL-associated proteins, we have previously developed a method to characterize the HDL glycoproteome [Huang, L. et al., J Proteome Res 13, 681-691, doi:10.1021/pr4012393 (2014)], and identified the importance of both sialylation and fucosylation in distinguishing among individuals who have coronary artery disease from those who do not [Krishnan, S. et al., J Proteome Res, doi:10.1021/acs.jproteome.5b00730 (2015)]. Another group has reported a similar finding. In HDL from patients with MetS both the amount of ApoC-III and SAA, and the glycosylation of ApoC-II, were altered compared to healthy controls [Savinova, O. V. et al., PloS one 9, e104833, doi:10.1371/journal.pone.0104833 (2014)], Thus, it is becoming increasingly apparent that there is differential expression of the HDL glycoproteome in health and disease; however, little is known about how glycan alterations affect HDL function.

The primary objectives of this study were to determine whether HDL glycoprotein composition: 1) differentiates between clinical groups, 2) modifies the effect of HDL-on response phenotype in monocytes stimulated with lipopolysaccharide(LPS), and 3) is associated with risk for infectious hospitalization in a high-risk group. Using our in-house developed technology, a detailed analysis of HDL composition was conducted on each sample including the concentrations of the HDL bound proteins; ApoC-III, α-1-antitrypsin (A1AT), and α-2-HS-glycoprotein (A2HSG), the quantification of the site-specific glycovariations of these proteins, a well as the concentrations of ApoA-I, serum amyloid A (SAA), LPS binding protein (LBP), cholesterol, and measurement of HDL particle size by dynamic light scattering. Our results demonstrate that HDL composition, including the site-specific glycosylation, differentiates between clinical groups, correlates with HDL's ability to modulate the LPS-induced monocyte cytokine-response, and may be predictive of HDL's ability to protect against infection.

Methods

Sample Collection

Serum samples from a total of 50 subjects who had participated in three previously conducted human studies were analyzed for this study. Five healthy control subjects who were part of a training run for the lager study, and 13 participants diagnosed with MetS who participated in a human study to assess the effects of high fat meals on postprandial inflammation, were randomly selected for this project. Both the healthy and MetS subjects bad to meet a set of Inclusion criteria, including not currently taking any medications and not having experienced any recent illnesses. MetS was characterized as having three out of the following five metabolic traits as defined by the American Heart Association: waist circumference>40 inches for men and 35 inches for women, fasting plasm triglyceride (TG) ≥150 mg/dL, fasting plasma HDL cholesterol (HDL-C)<40 mg/dL for meal and <50 mg/dL for women, blood pressure≥130/85 mmgH, and fasting glucose≥100 mg/dL [Israili, Z. H. et al., American journal of therapeutics 14; 386-402, doi:10.1097/01.pap.0000249936.05650.0c (2007)]. The institutional Review Board of the University of California at Davis approved this study protocol, and all participants gave written informed consent prior to starting the study, as well as consent for the use of their biological specimens and anonymized data in follow-up studies. All methods of this study were carried out in accordance with approved guidelines. The study was registered at clinicaltrials.gov under NCT01811329. Seven additional healthy control subjects who participated in a methods development study donated blood samples through a study that was approved by the Institutional Review Board of the University of California at Davis Subjects provided written informed consent and the study followed all approved guidelines for the protection of subjects.

The ACTIVE/ADIPOSE study enrolled prevalent hemodialysis patients from 14 centers in San Francisco CA and Atlanta GA from June 2009 through August 2011 [Collins, A. J. et al., Am J Kidney Dis 57, A8, e1-526, doi 10.1053/j.ajkd.2010, 10.007 (2011)1]. Blood was drawn prior to dialysis every six months, separated by centrifugation at the local facility and then shipped on dry ice to the core laboratory at the University of California Davis where it was thawed once, aliquoted and then frozen over liquid $N_2$ until assay. Body composition was measured as Body Mass Index, waist circumference. Stored samples that had not been previously thawed were obtained from patients enrolled in the ACTIVE/ADIPOSE study [Johansen, K. L. et al., Am J Kidney Dis 64, 600-607, doi:10.10534.ajkd.2014, 03.016 (2014)] with type 2 diabetes mellitus receiving hemodialysis (HD) who were hospitalized for an infectious event within 4 to 56 days (mean 24.5±23.6 days) of the blood collection (n=13), and patients with diabetes mellitus receiving HD who remained infection-free for at least the subsequent two years (median 799.5, $25^{th}$ percentile 800 $75^{th}$ percentile 840) (n–13) The samples were grouped for analysis based on the time until first infectious event. Two samples (one from the HD+ group and one from the HD– group) did not have adequate HDL levels to complete the Immune cell assays at the 30 mg/dL HDL cholesterol final concentration and were therefore excluded from analysis.

HDL Isolation by Ultracentrifugation

Preparation of HDL was performed as described previously [Huang; J. et al., J Proteome Res 13, 681-691, doi: 10.1021/pr4012393 (2014)] and scaled up for preparative purposes. Potassium Bromide (KBr) densities of 1.019, 1.063 and 1.340 g/mL were freshly made weekly and verified using the Densito 30PX portable densitometer (Mettler Toledo, Columbus, OH, USA). Briefly, plasma samples (1.9 mL) were previously adjusted to d=1.019 by adding a concentrated KBr solution (d=1.340) and underlaid to KBr solution of d=1.019 for a final volume of 4.7 mL tube (OptiSeal, Beckman Coulter). Ultracentrifugation was performed using a Beckman Optima MAX-TL equipped with a TLA-110 fixed-anglerotor (Beckman Coulter) for 2 h, at 657,000×g and 15° C. The VLDL-IDL fraction of density lower than 1.019 was recovered from the top of the tube (1.9 mL), and the remaining infranate was adjusted to d=1,063 and underlaid with KBr solution of the same density (d=1.063) followed by ultracentrifugation for 3 h. After centrifugation, the LDL supernate fraction (1.9 mL) was collected and the infranate containing the HDL fraction adjusted to d=1.210, and 4.7 mL subjected to ultracentrifugation for 3.5 h. The HDL fraction (121-1.063 g/mL) was collected from the top of the tube (1.0 mL) and subjected to diafiltration using Amicon ultra-3K centrifugal filter devices. During this process the HDL fractions were desalted by washing out the KBr salt with water (Optima LC/MS) by two consecutive steps of centrifugation for 25 min at 4° C. and I4,000×g. The concentrated HDL fraction was recovered in Optima Water for glycoproteomic analysis and in PBS for the immune experiments.

HDL Fractions Analyses

Each of the following was measured in the separated HDL fractions. HDL cholesterol was measured using a colorimetric Total Cholesterol assay from Cellbiolabs (Cellbiolabs, San Diego CA). ApoA-I was measured using the Cellbiolabs human ApoA-I Elisa kit (Cellbiolabs, San Diego CA). Total Endotoxins were measured using a chromogenic LAL (Linulus Amebocyte Lysate) assay (Pierce Biotechnologies, Grand Island, NY) in a subset of 18 samples to verify that there was no significant contamination on of the isolated HDL with LPS, and that there were no differences in the amount of LPS in the isolated HDL fractions between groups. There were negligble levels of endotoxin in the samples and there were so differences in endotoxin levels between groups (data not shown). LBP was measured using an electrochemiluminescent assay (Meso Scale Discovery, Rockville, MD). ApoA-I and LBP were normalized to total cholesterol in the HDL fraction.

Glycoproteomic Analysis

Apolipoprotein C-III (Apo C-III), α-1-antitrypsin (A1AT), α-2-human serum glycoprotein (A2HSG) from human plasma and recombinant human apo serum amyloid A (SAA) wet purchased from Sigma-Aldrich (St. Lous, MO). Sequencing grade modified trypsin and dithiothreitol (DTT) were purchased from Promega (Madison, WI). Iodoacetamide (IAA) was purchased from Sigma-Aldrich (St. Louis, MO). All the trypsin digestion experiments were carried out in freshly made 50 mM $NH_4HCO_3$ solutions. For the tandem mass spectrometry experiments, 20 ug of ApoC-III, A1AT, A2HSG, and SAA in 100 uL ammonium bicarbonate solutions were reduced using 2 uL of 550 mM DTT in 60° C. for 50 min then alkylated using 4 uL of 450mMIAA in the dark at room temperature for 30 min and digested at 37° C. overnight using 1 ug of trypsin. Digestion reactions were stopped by placing the samples in −20° C. for 1 hr. the resulting tryptic digests were injected into the LC QE-Orbitrap instrument without-any sample cleanup. 10 uL of HDL samples were added to 90 uL of the buffer solution and digested using the above procedure but 2 ug of the trypsin was used for the digestion. Byonic software (San Carlos, CA) was used to identify the peptides and the glycopeptides using accurate mass and fragment ion patterns.

For the peptide and glycopeptide quantitation, the four protein standards were pooled together and digested using trypsin. Serial dilution was performed and 6 concentration levels with ratios 1:22.5:2:5:2 were created for the protein concentration measurements, the highest concentration being 0.1810. The peptides and glycopeptides were analyzed using Agilent 1290 infinity LC system coupled to an Agilent 6490 triple quadrupole (QqQ) mass spectrometer (Agilent technologies, Santa Clara, CA). Thea analytical column used for UPLC separation was an Agilent eclipse plus C18 (RRHD 1.8 μm, 2.1×100 mm) connected to an Agilent eclipse plus C18 pre-column (RRHD 1.8 μm, 2.1×5 mm). 2 uL of the HDL ample solutions were injected and analyzed using a 14-minute binary gradient as follows: 0.0-0.5 min, 2% B; 0.5-5, 2-15% B; 5-10 min, 15-44% B; 10-12.1 min, 44-100% flush at 100% B for 1.1 min and equilibrium for 0.8 min at 2% B. Solvent A was composed of 3% acetonitrile, 0.1% formic acid in while solvent B was 90% acetonitrile, 0.1% formic acid all in nano pure water (v/v). The sample flow rate was 0.5 mL/min.

The MS parameters for the glycopeptides have been optimized before in our lab [Hong, Q. et al., *Analytical Chemistry* 85, 8585-8593, doi:10.1021/ac4009995 (2013)]. Briefly, positive ion mode was used to ionize the samples at unit resolution. The dynamic multiple reaction monitoring (MRM) mode that monitors analyte transitions only when they are eluting from the LC was used for quantitation. The collision energies for each peptide and the glycopeptide transitions were optimized to achieve optimum sensitivity. Unique peptides for each protein and the common glycan oxonium fragments, such as m/z 204.08 (He % NAc) 366, 14 (Hex1HexNAc1), 292,09(Neu5Ac) and 274.09 (Neu5Ac—$H_2O$) were used to quantify proteins and glycopeptides respectively. Protein concentrations (in ion counts) were normalized to the total cholesterol in the HDL extract. Each glycopeptide concentration (in ion counts) was normalized to the total amount of its parent protein (in ion counts). Agilent Mass Hunter quantitative analysis software was used to analyze the MRM data with limit of detection signal to noise ratio (S/N)≥3 and limit of quantitation S/N≥6. Glycan composition was designated by the number of hexose (Hex) residues, N-acetylhexosamine (HexNAc) residues, fucose (Fuc) residues, and N-acetylneuraminic acid (NeuAc) residues. As an example, a glycan containing 5 Hex, 4 HexNAc, 0 Fuc and 2 NeuAc residues was designated by the name 5-4-0-2. Nomenclature for each glycopeptide includes the protein name, followed by the site of the glycan attachment, and the glycan composition (e.g. A1AT_70_5402).

Monocyte Assay

Heparinized blood samples from healthy adult donors were purchased from BloodSource (Mater, CA). Peripheral blood mononuclear cells (PBMCs) were isolated using Ficoll-Paque density gradients (GE Healthcare Bioscience). Cells were resuspended in RPMI 1640 tissue culture medium supplemented with 5% fetal bovine serum and 100 U/ml penicillin-streptomycin (all from Gibco BRL, Gaithersburg, Md.), washed in the medium and then were counted-using an automated TC20 cell counter (Bio-rad). Monocytes were positively isolated from PBMCs using BD IMag™ CD14 magnetic particles (BD Biosciences) according to the manufacturer's protocol. Monocytes were cultured in duplicate in a 96 well plate (1~2×$10^6$ cells/ml, 200 ml/well) with or without 10 ng/ml LPS (PS-EK from *E. coli* K12, InvivoGen) in the presence or absence of HDL from individual subjects for 24 hours, with a 0 LPS, 0 HDL negative control. Cholesterol concentrations in the separated HDL fractions were measured as described above, and used to concentrate each sample to a final concentration of 30 mg/dL cholesterol in the well. Culture supernatant aliquots for cytokine measurement were stored at −80° C. until analysis.

Cytokine Measurement

We selected IL-6 as a prototypical cytokine to measure as it is one of the classic cytokines released by monocytes in response to LPS and its impact on plaque development and morphology has been well described [Schieffer, B. et al., *Circulation* 110, 3493-3500, doi:10.1161/01.CIR.0000148135.08582.97 (2004); Tous, M. et al., *Cytokine* 34, 224-232, doi:10.1016/j.cyto.2006.05.007 (2006)]. Culture supernatant samples were diluted (1:2) using culture medium. Assays were performed according to the manufacturer's instructions. Briefly, 50 μl of each diluted sample were added to a suspension of beads coated with primary antibody against IL-6 in each well of an assay plate and incubated for 30 min at room temperature in the dark with shaking at 450 rpm. After the incubation, the beads were washed 3 times and subsequently reacted with a mixture of biotin-conjugated secondary antibody. After a 30 min reaction, the beads were again washed and re-suspended in assay buffer containing streptavidin-phycoerythrin (Str-PE). After 10 min of agitation at room temperature in the dark, the beads were washed and re-suspended in assay buffer. Concentrations of IL-6 were measured using a Bio-Plex 200 (Bio-Rad Laboratories, Inc., Hercules, CA, USA) with known concentrations of human IL-6 standard (Bio-Rad). Bio-Plex Manager software (Bio-Rad) was used to calculate the concentrations of IL-6 in each well.

HDL Particle Size Measurement

HDL size was measured using the 90Plus/BI-MAS Particle Size Analyzer (Brookhaven Instruments Corp., Holtsville, NY) and the MAS OPTION Software, which combines the photon correlation spectroscopy (PCS) technique with Quasi-elastically scattered light (QELS). Twenty five ul aliquots of native HDL extracts were diluted to make up to a 1 mL aliquot of PBS in a Sarstedt Acryl Cuvette (Sarstedt AG & Co, Germany), and placed in the cuvette bolder in the Particle Size Analyzer. Three-minute measurements were collected, and processed by the MAS OPTION software forming an autocorrelation function returning size in mm.

Statistical Analyses

All statistical analyses were performed using R-statistical software (R core development, Vienna) and JMP (R) Pro11.2.0 64-bit (SAS institute, Cary NC), and Microsoft Office Excel (Microsoft, Seattle WA). Shapiro-Wilk tests were used to determine the normality of data distribution. When data were normally distributed, ANOVA with Tukey's post hoc was used. When data were not normally distributed, non-parametric van der Weardan's test, followed by Steel-Dwaas post hoc tests were used. The quantity of IL-6 in each well where HDL was added was converted to a % change in IL-6 relative to the 0 HDL treatment to calculate IL-6 response using the following formula:

$$\left( \frac{\left(\left(\frac{pg}{mL} IL\text{-}6 \text{ in } LPS - HDL\right) - \left(\frac{pg}{mL} IL\text{-}6 \text{ in } LPS + HDL\right)\right)}{(pg/mL\ IL\text{-}6 \text{ in } LPS - HDL))} * 100 \right)$$

The negative control wells (i.e. 0 HDL and 0 LPS) had no cytokine response. The % change values were used to categorize individual subjects' HDL into either enhancement (where IL-6 response was a positive value) or suppression (where IL-6 response was a negative value) of IL-6 response, Van der Wearden's non-parametric tests were used to identify group differences between control, MetS and HD subjects, as well as IL-6 response groups. Steel-Dwaas multiple comparison tests were used with a p<0.05 as an indicator of significance.

Partial Least Squares Discriminant Analysis (PLS-DA) was used to explain the variance between clinical groups (contol vs MetS vs HD) as well as IL-6 response groups (IL-6 increased vs. decreased). A random $2/3^{rd}$ subset was chosen to be the training set and the other $1/3^{rd}$ to be the test set for cross-validating each PLS model. External cross-validation was done by extracting PLS models from three repeated runs of the test-training set validation. The models were built using the NIPALS method, which extracts one factor at a time and Was used to evaluate which variables primarily explain the variation between groups. The optimal models were chosen based on the goodness of prediction statistic Q2. In addition, the coefficients of multiple determination $R^2$ for independent and dependent variables were also used to determine the goodness of fit. Both these statistics were also considered while evaluating variable selection. Variables that had a Variable Importance Plot (VIP) score of >1 were considered as the primary variables driving the separation between groups. The model diagnostics (Q2, $R^2X$, $R^2Y$) are all reported as mean±standard deviation.

Glycopeptides for each protein were also summed based on whether they were sialylated, fucosylated, or undecorated, and then mol percentages were calculated for these categories including mol % non-fucosylated, mol % monofucosylated, mol % difucosylated, mol % non-sialylated, mol % mono-sialylated; mol % di-sialylated, mol % undecorated (i.e. neither fucosylated nor sialylated), mol % fucosylated+sialylated (i.e. fucosylated and sialylated). In each case, the mol % category was calculated as the amount of the category divided by the total glycopeptides for each protein (e.g. A1AT mol % monofucosylated was calculated as the total of monofucosylated glycopeptides on A1AT divided by the total glycopeptides on A1AT). The individual glycopeptide date and mol % categories were also evaluated to determine differences between the IL-6 response groups, and between the HD patients who developed infections and those who did not also using the van der Wearden test, with Steel-Dwaas correction for pair-wise comparison errors.

Results

Anthropometric and Clinical Characteristics

Table 1 compares controls to the MetS and HD groups. The Control group had a significantly lower BMI compared to the MetS group (p<0.001), as well as the HA group (p<0.001). The control group was also significantly younger than the HD (p<0.001)group. No differences were found between groups in HDL particle size. Cholesterol in the isolated HDL was significantly higher in the control compared to the HD group (p=0.031). ApoC-III and LBP were higher in both HD and MetS compared to controls (p<0.01 for both). SAA was higher in the HD group compared to control and MetS groups (p<0.001 for both). The MetS group had higher circulating triglycerides compared to HD (p<0.01). Plasma TG and CRP levels were not measured in the control subjects. The MetS subjects had lower systolic blood pressure compared to HD (p<0.01), as did the controls (p<0.01).

Glycoprotein and Site-Specific Glycopeptide Composition in the Clinical Groups

The glycopeptides monitored on each of the 3 proteins (i.e. A1AT, A2HSG, and ApoC-III), as well as the relative distribution of glycans on each site as measured in the protein standard are depicted in FIG. 1. As shown in the figure, there were three N-linked glycosylated sites in A1AT, 2 N-linked and 2 O-linked glycosylation sites in A2HSG, and one O-linked glycosylated site in ApoC-III. For each glycan composition a putative structure is depicted, with the pie charts showing the relative abundances of different glycans within a given site based on analyses of the protein standards.

Figure 2:
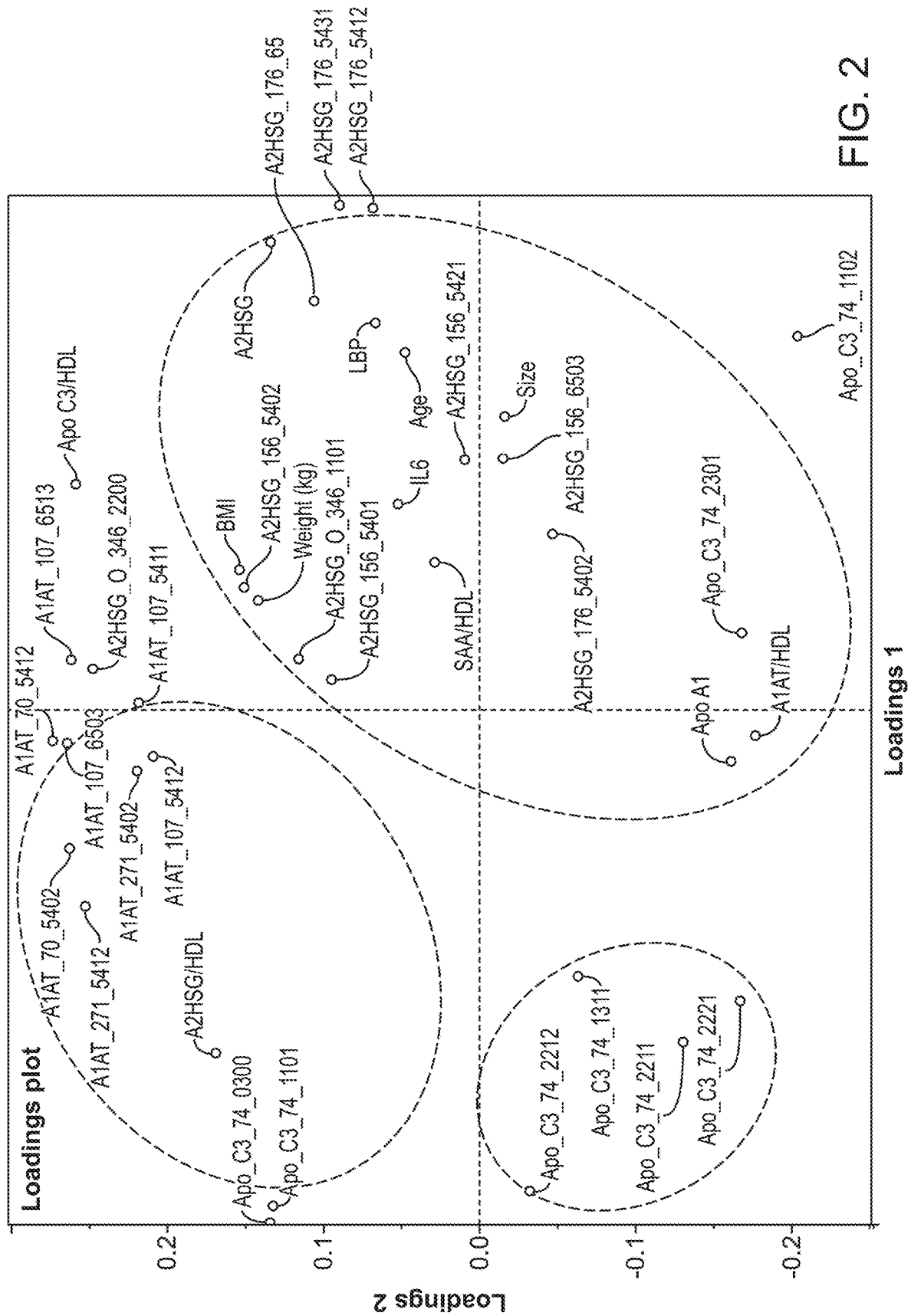
FIG. 2: PLS-DA model Loadings, Scores and Variable importance plots discriminating anthropometric, clinical and glycoproteomic variables in n=50 individuals based on clinical groups—controls, diabetic patients on hemodialysis (HD), and subjects with metabolic syndrome (MetS). The loadings plot displays the anthropometric, clinical and glycopeptide variables that explain the variance between the groups (highlighted using blue for MetS, red for controls, and green for HD), while the scores plot indicates the groups of participants in each of the clinical group, and their distribution in this dimensional space. The X and Y axes represent the X-loadings $1^{st}$ and $2^{nd}$ components respectively. The variable importance plot identified 14 primary variables (highlighted using colors blue, green and red) that drive the difference between the clinical groups. The model had a Q2 of 0.92, explaining 62% of variance in X variables, and 79% of variance in Y variables.
Figure 2:
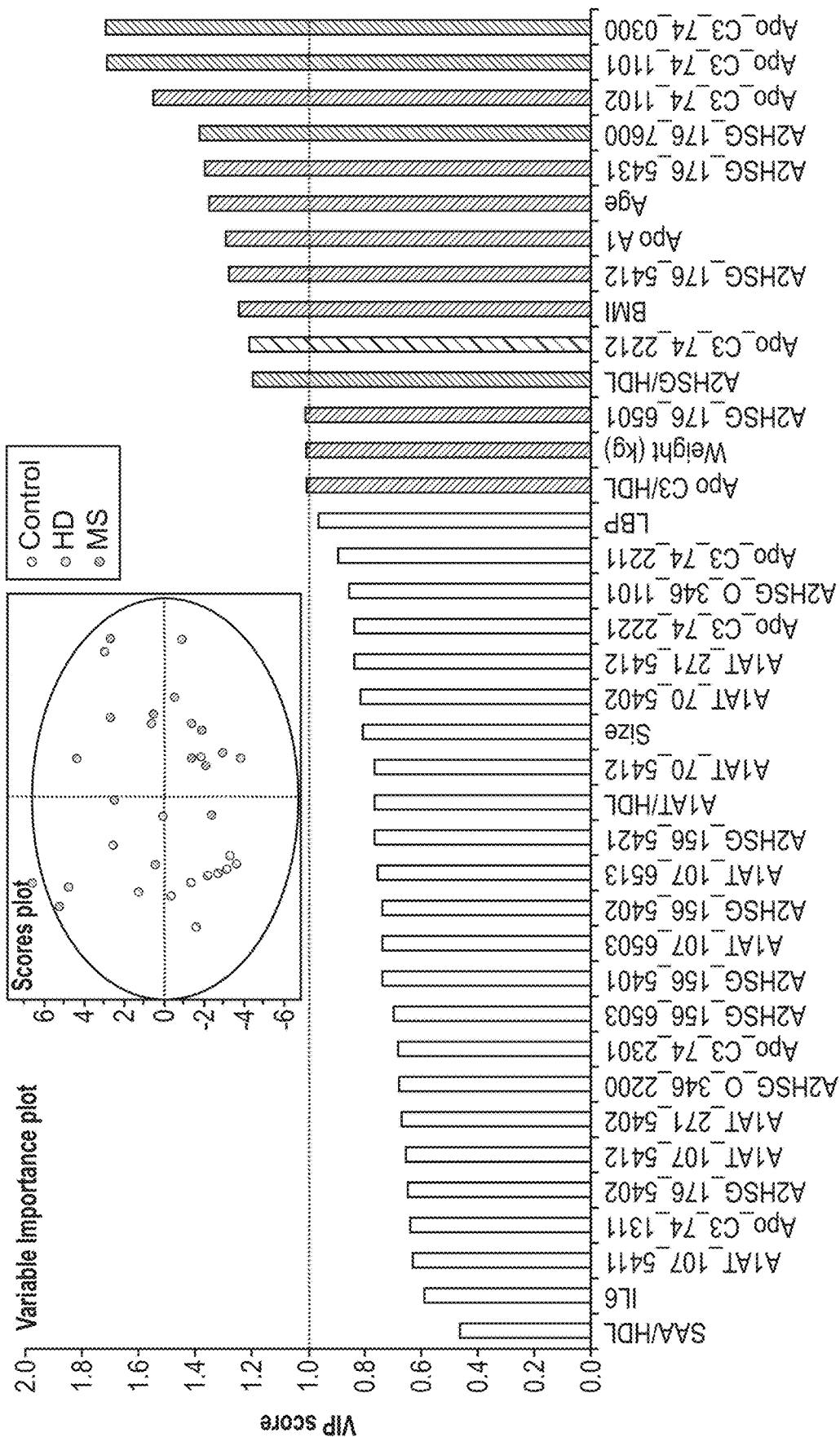

FIG. 2 displays the variance in anthropometric, clinical and glycopeptide variables between the clinical groups. In the loadings plot, the blue highlighted section corresponds to variables associated with the blue dots in these plot, belonging to the MetS group. Similarly, the green highlight and green dots represent the HD group, and the red highlight and red dots represent the control group. The variable importance plot also has variables colored blue, green or red, with variables that have a VIP>1 deemed significant in the discriminant analysis corresponding to the Mets, HD and control groups respectively. The HD group was defined by higher ApoC-III, ApoA-I, body weight, BMI, age, as well as the glycopeptides A2HSG_176_6501, A2HSG_176_5412, A2HSG_176_5431, and Apo C3_74_1102. Mets was characterized by higher A2HSG, A2HSG_176_7600, ApoC3_74_1101, and ApoC3_74_0300. Controls were marked by higher ApoC3_74_2212. The PLS-DA model had a Q2 value of 0.92+/−0,01, an $R^2X$ value of 0.62+/−0.01 and $R^2Y$ value of 0.79+/−0.01. The number of variables with VIP values>1 was 14, and given the high Q2 and $R^2X$ and $R^2Y$ values, these VIP variables are strong predictors of separation into the MetS, HD and control groups.

Figure 3:
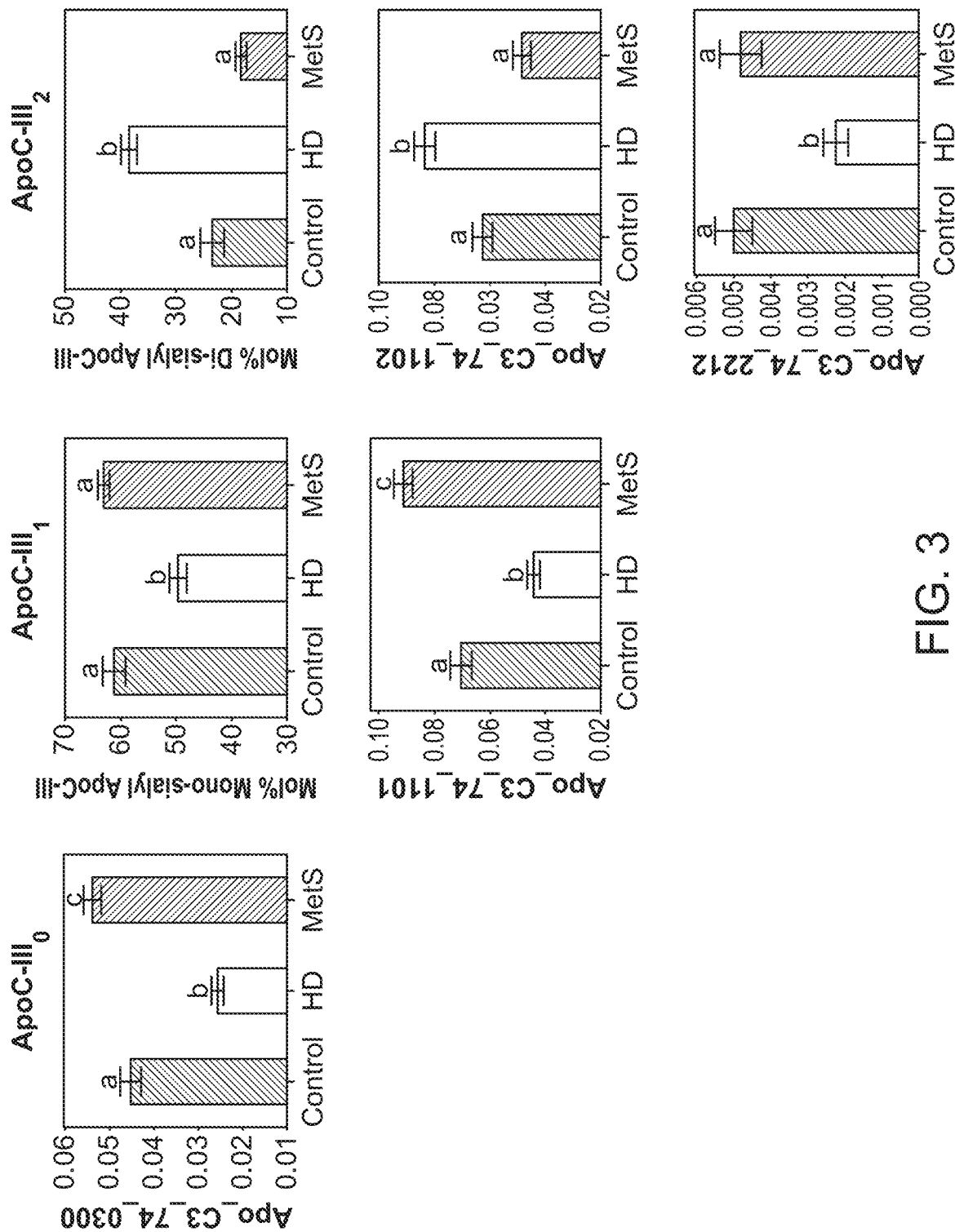
FIG. 3. Apolipoprotein C-III (ApoC-III) glycosylation patterns in HDL isolated from control, diabetic patients on hemodialysis (HD), and metabolic syndrome (MetS) subjects. Significant differences between groups by post-hoc tests at p<0.05 indicated by 'a', 'b' and 'c' superscripts. ApoC-III$_0$, non-sialylated; ApoC-II$_1$, mono-sialylated; ApoC-III$_2$, di-sialylated.

Non-parametric univariate analysis also showed significant differences between the clinical groups (control vs MetS vs HD) in the glycosylation patterns for the three glycoproteins that were characterized. The key results for ApoC-III are shown in FIG. 3. The non-sialylated isoform of ApoC-III. (ApoC-III$_0$) was represented by the single undecorated glycan 0300 on site 74, and was significantly lower in HD compared to controls and MetS subjects (p<0.001 for both) and higher in MetS than controls (p=0.031). The mol % of mono-sialylated ApoC-III isoforms (ApoC-III$_1$) was significantly lower in HD than control and MetS subjects (p≤0.01 for both). The mono-sialylated glycan 1101 on site 74 was lowest in HD, highest in MetS, and intermediate in control subjects (p≤0.005 for three). The mol % of di-sialylated ApoC-III isoforms (ApoC-III$_2$) was significantly higher in HD than controls and MetS subjects (p≤0.001 for both), with levels being lowest in MetS (though the difference between Mets and controls was NS). The di-sialylated glycan 1102 on site 74 was also increased in HD compared to controls and MetS subjects (p≤0.01 for both) with levels being lowest in MetS (although again, the difference between MetS and controls was NS). However the opposite pattern was seen with the di-sialylated glycan 2212, which was lower in HD than in controls and MetS subjects (p≤0.005 for both). Thus, while MetS subjects bad the lowest levels of sialylation in ApoC-III, HD patients had a specific enrichment in ApoC-III$_2$ with controls being intermediate.

Figure 4:
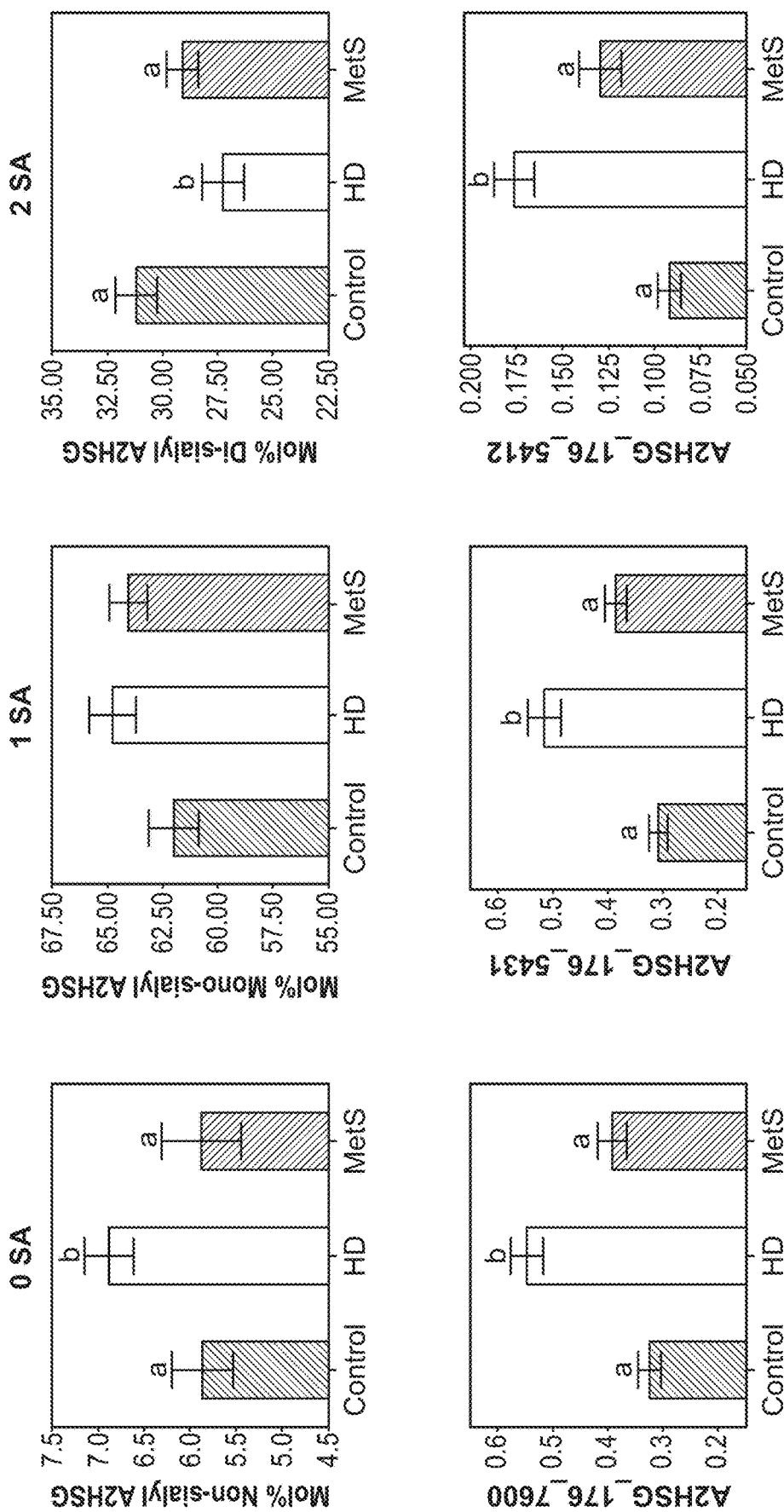
FIG. 4: Glycosylation patterns of α-2HS-glycoprotein (A2HSG, fetain A) in HDL isolated from control, hemodialysis (HD), and metabolic syndrome (MetS) subjects 0, 1 and 2 SA represent non-, mono- and di-sialylated glycoforms. Significant differences between groups by post-hoc tests at p<0.05 indicated by 'a' and 'b' superscripts.

Results for A2HSG are shown in FIG. 4. The mol % of non-sialylated A2HSG was significantly higher in the HD subjects compared to controls (p=0.035). The mol % mono-sialylated A2HSG glycoforms did not reach statistical significance but showed a trend toward an increase in HD compared with control subjects, with MetS subjects being intermediate. On the other hand, the mol % of di-sialylated A2HSG was significand lower in HD compared to controls and MetS (p<0.05). Both the individual non-sialylated glycan 7600 on site 176 and the di-sialylated glycan 5412 on site 176 were significantly increased in HD compared with control and MetS subjects (p<0.005 for non-sialylated and p<4.01 for di-sialylated for all three), as was the mono-sialylated glycan 5431 on site 176 (p<0.01 for both). Thus, HD patients generally bad less sialylation in A2HSG but increased levels of the specific glycan 5412.

Figure 12:
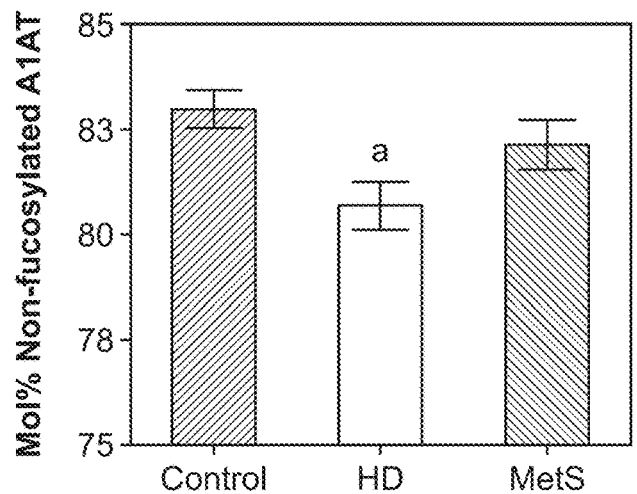
FIG. 12: Difference between clinical groups in non-fucosylated alpha-1 antitrypsin (A1AT), disialytated A1AT and monofucosylated alpha-2HS-glycoprotein (A2HSG) between control subjects, diabetic patients on hemodialysis (HD), and subjects with metabolic syndrome (MetS). Significant differences ('a' subscript indicate individual group differences at p<0:05).
Figure 12:
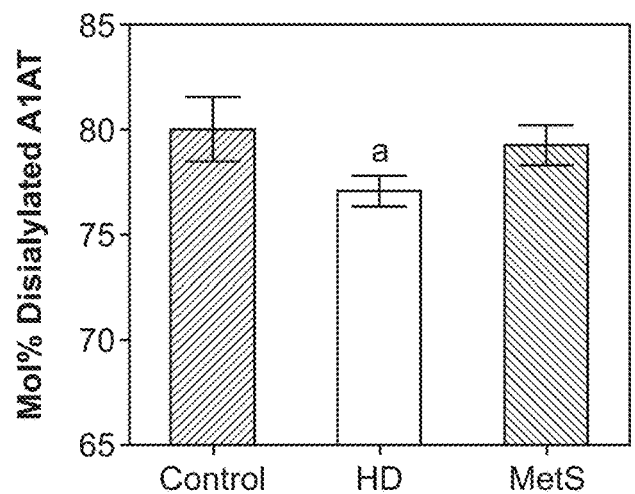
Figure 12:
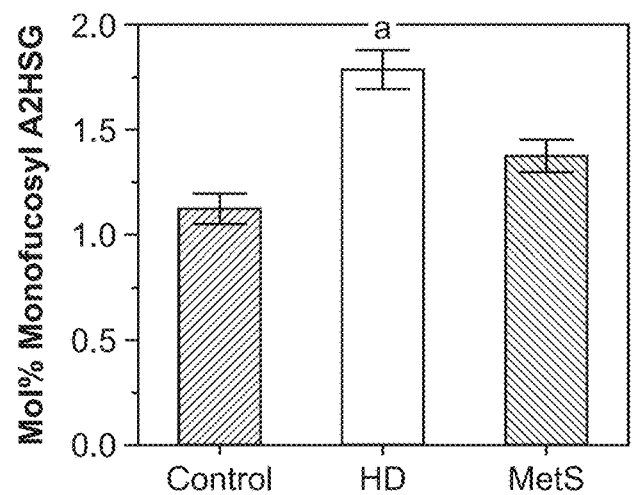

HD patients bad less non-fucosylated, more monofucosylated, and less di-sialylated A1AT compared to MetS and controls (p<0.05), with no differences between MetS and controls (FIG. 12). These data indicate that an enrichment in fucosylated glycans on A1AT may be characteristic of HD patients.

IL-6 Response Groups

Figure 5:
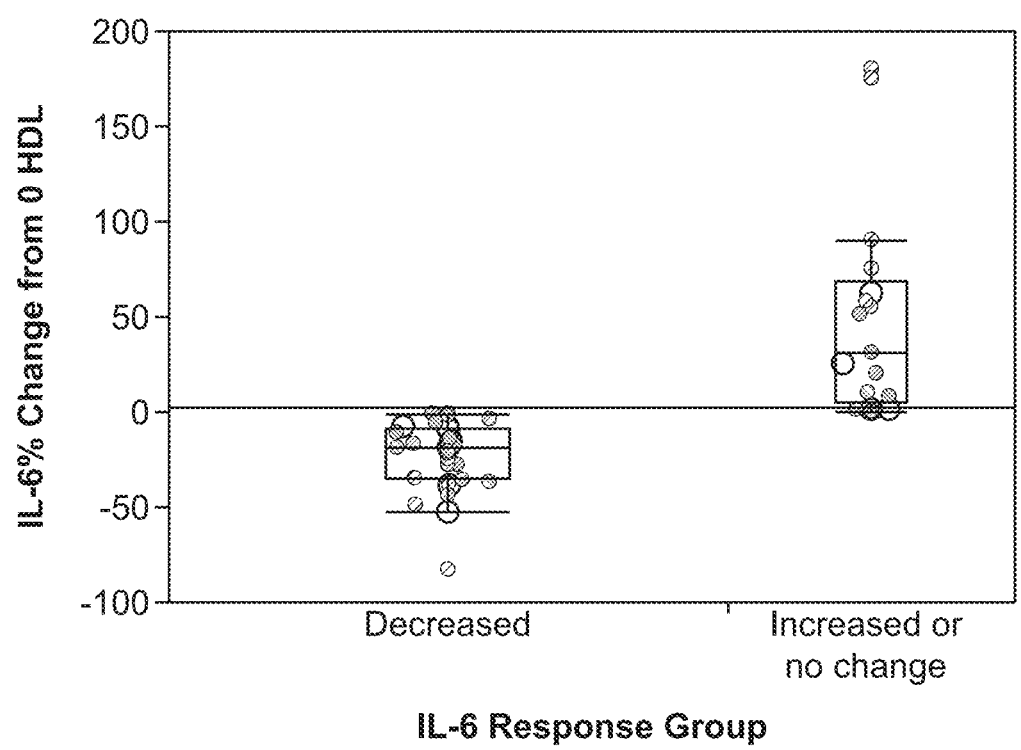
FIG. 5: IL-6% response in the decreased vs. increased or no change groups. Experimental subjects with different health conditions were grouped based on their HDL pre-exposure to standard monocytes causing decrease vs increase or no change in IL-6 secretion upon lipopolysaccharide (LPS) stimulation. Control subjects (green circles); metabolic syndrome subjects (blue circles); diabetic patients receiving hemodialysis who had an infectious hospitalization event(filled red circles) and those who did not have an infectious event(open red circles).
Figure 6:
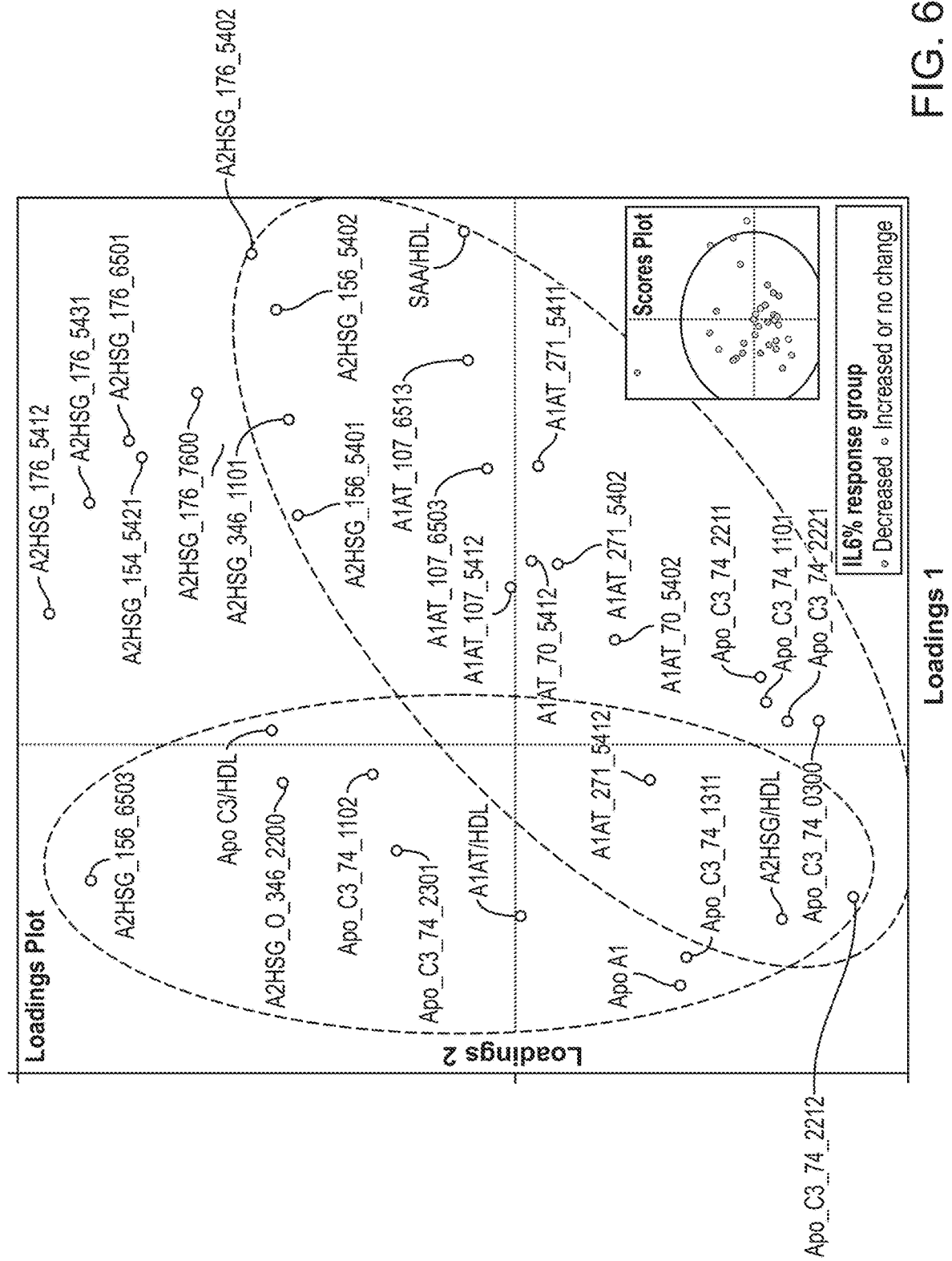
FIG. 6: PLS-DA model Loadings, Scores and Variable importance plots discriminating glycoproteomic variables in n=50 individuals based on IL-6 response groups (percentage change in IL-6 secretion with HDL pre-incubation in LPS-stimulated monocytes)—Decreased (color red) or Increased or no change (color blue). The loadings plot displays the glycopeptide variables that explain the variance between the groups, while the scores plot indicates the groups of participants in each of the IL-6 response group, and their distribution in this dimensional space. The variable importance plot identified 13 primary variables (highlighted using colors blue and red) that drive the difference between the IL-6 response groups. The model had a Q2 of 0.14, explaining 37% of variance in X variables, and 31% of variance in Y variables.
Figure 6:
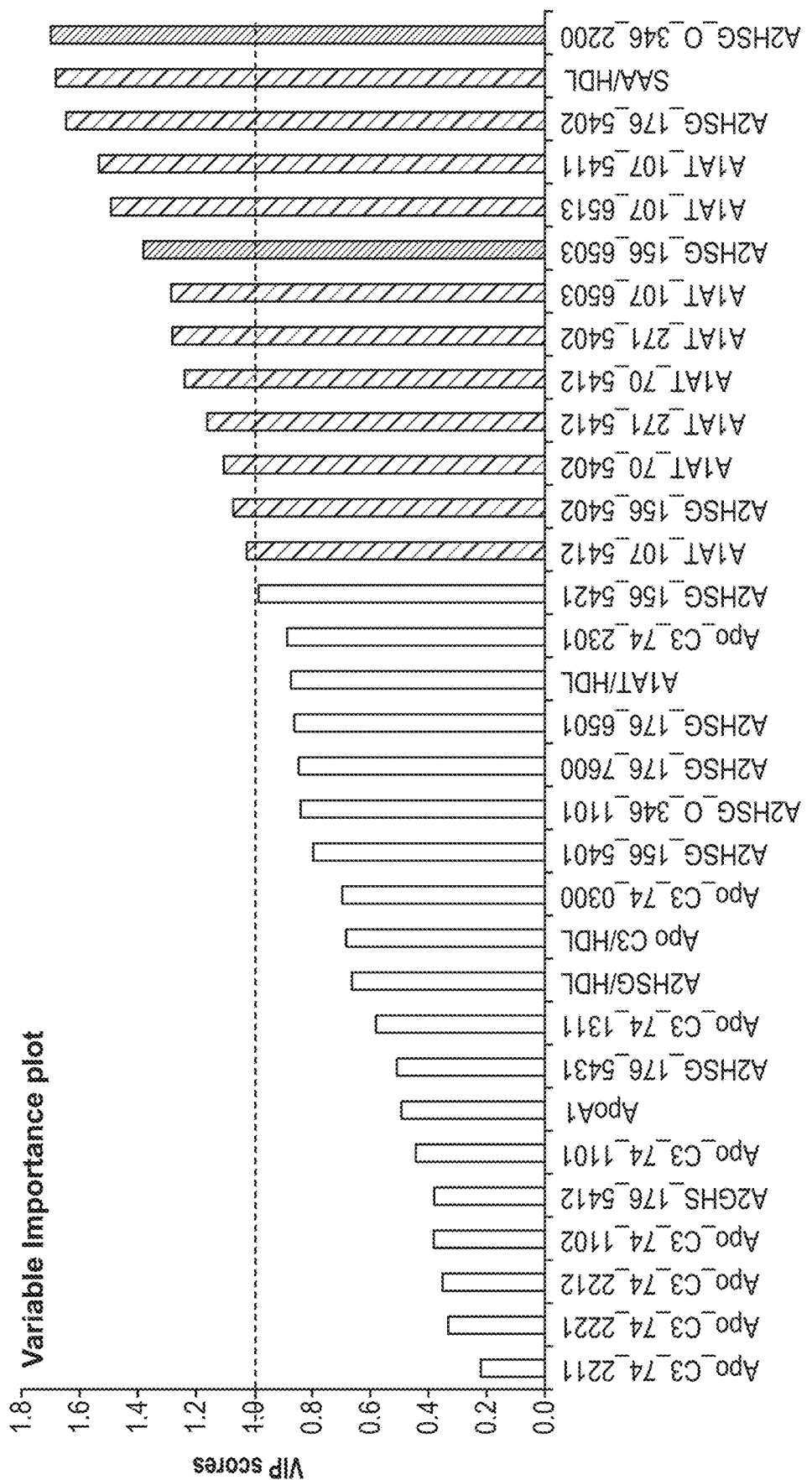

Out of the 50 HDL samples analyzed 33 decreased and 17 increased or did not change IL-6 secretion in monocytes in response to LPS stimulation (FIG. 5). The grand mean in IL-6 response across all 50 HDL samples was no effect on IL-6 secretion. However, the range in responses across the 50 individual, HDL samples was from an 83% decrease to a 180% increase in IL-6 relative to 0 HDL. Given this wide range of IL-6 responses to HDL we separated responders versus non-responders to evaluate how the HDL glycoforms differed between these groups. Thus, subjects were divided into those whose HDL increased (i.e. IL-6% change ≥0) vs. decreased (i.e. IL-6% change <0.0) IL-6 response. The mean response of the group In which HDL increased IL-6 secretion was a 50% increase in IL-6, and the mean response in the group that decreased IL-6 secretion was a 23% decrease in IL-6. There was a mixture of samples from each of the 4 clinical groups (controls, MetS, HD+ and, HD− subjects) in both of the IL-6 response groups, suggesting that the ability of HDL to suppress IL-6 secretion in LPS-stimulated monocytes may not be directly linked to the clinical characteristics of the patient but rather, more likely, the composition of their HDL particles. In support of this hypothesis, a multivariate model for IL-6 groups could not be fitted by the NIPALS PLSDA algorithm, using a $\frac{1}{3}^{rd}$ $\frac{2}{3}^{rd}$ training and test set paradigm, when the anthropometric, clinical, and glycopeptide data were include. However, the PLS DA models using only glycopeptides to predict the IL-6 response groups were successful (FIG. 6). The red and blue highlighted regions in the loadings plot correspond to the red and blue dots in the scores plot denoting decreased (red) and increased or no change in IL-6. (blue) groups. Similar to FIG. 2, the VIP variables are highlighted using red and blue colors to indicate decreased and increased IL-6 response groups. The Q2 value was 0.14+/−0.01, and R$^2$ values were 0.38+/−0.17 and 0.31+/−0.21 for the X and Y variables respectively, with 13 variables having VIP values>1.

Figure 7A:
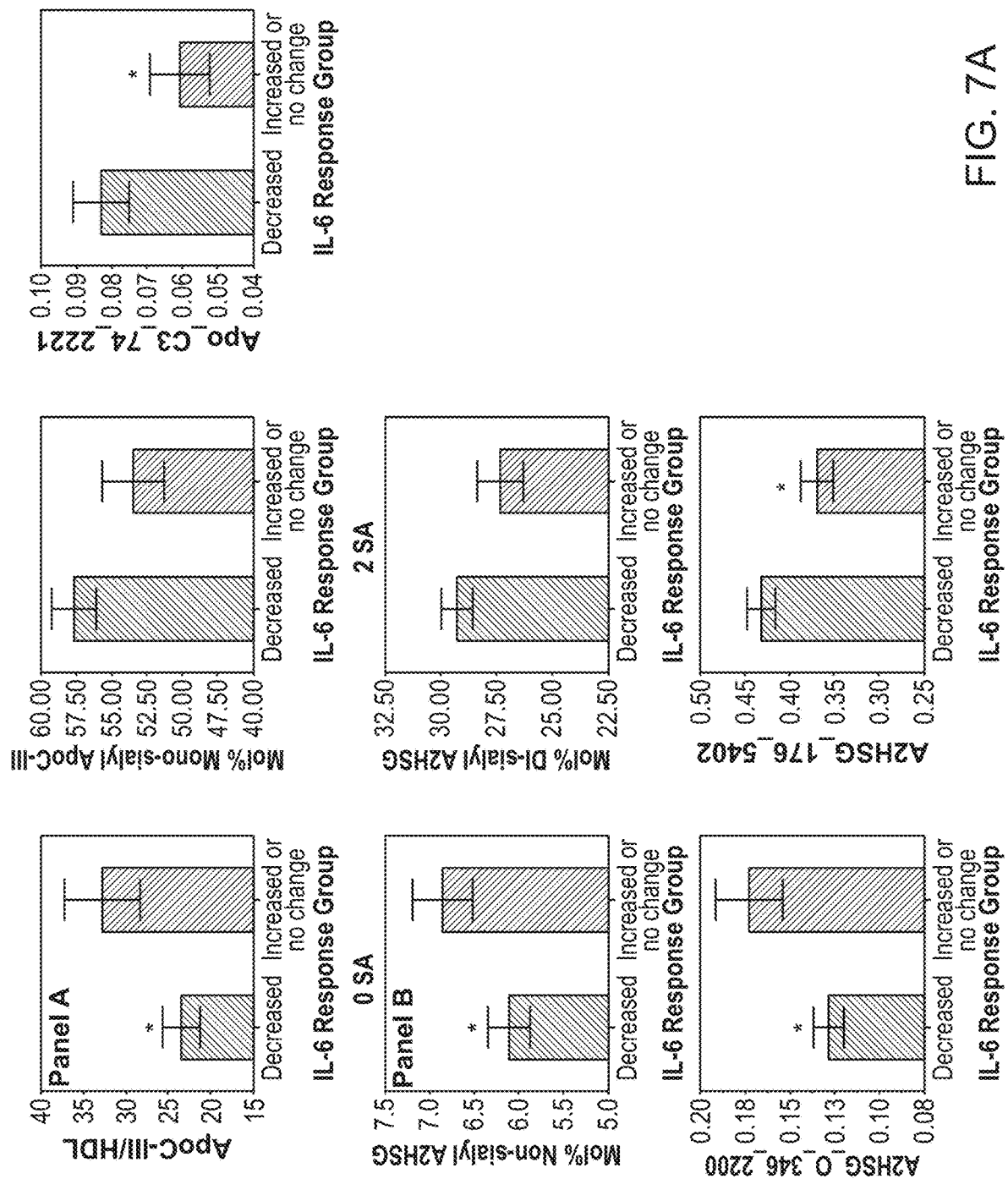
FIG. 7: Panel A: Differences in protein amounts and glycosylation patterns of apolipoprotein C-III (ApoC-II) by interleukin 6 (IL-6) response group comparing HDL that decreased vs. increased or did not change secretion of IL-6 in-LPS-stimulated monocytes. Panel B: Differences in glycosylation patterns in α-2HS-glycoprotein(A2HSG, fetuin A) between IL-6 response groups comparing isolated HDL that decreased vs. increased or led to no change in IL-6 secretion in LPS-stimulated monocytes. Panel C: Differences in protein amounts and glycosylation patterns of α-1-antitrypsin (A1AT) by IL-6 response group comparing HDL that decreased vs. increased or did not change secretion of IL-6 in LPS-stimulated monocytes. Differences are indicated using '*' at p<05.
Figure 7B:
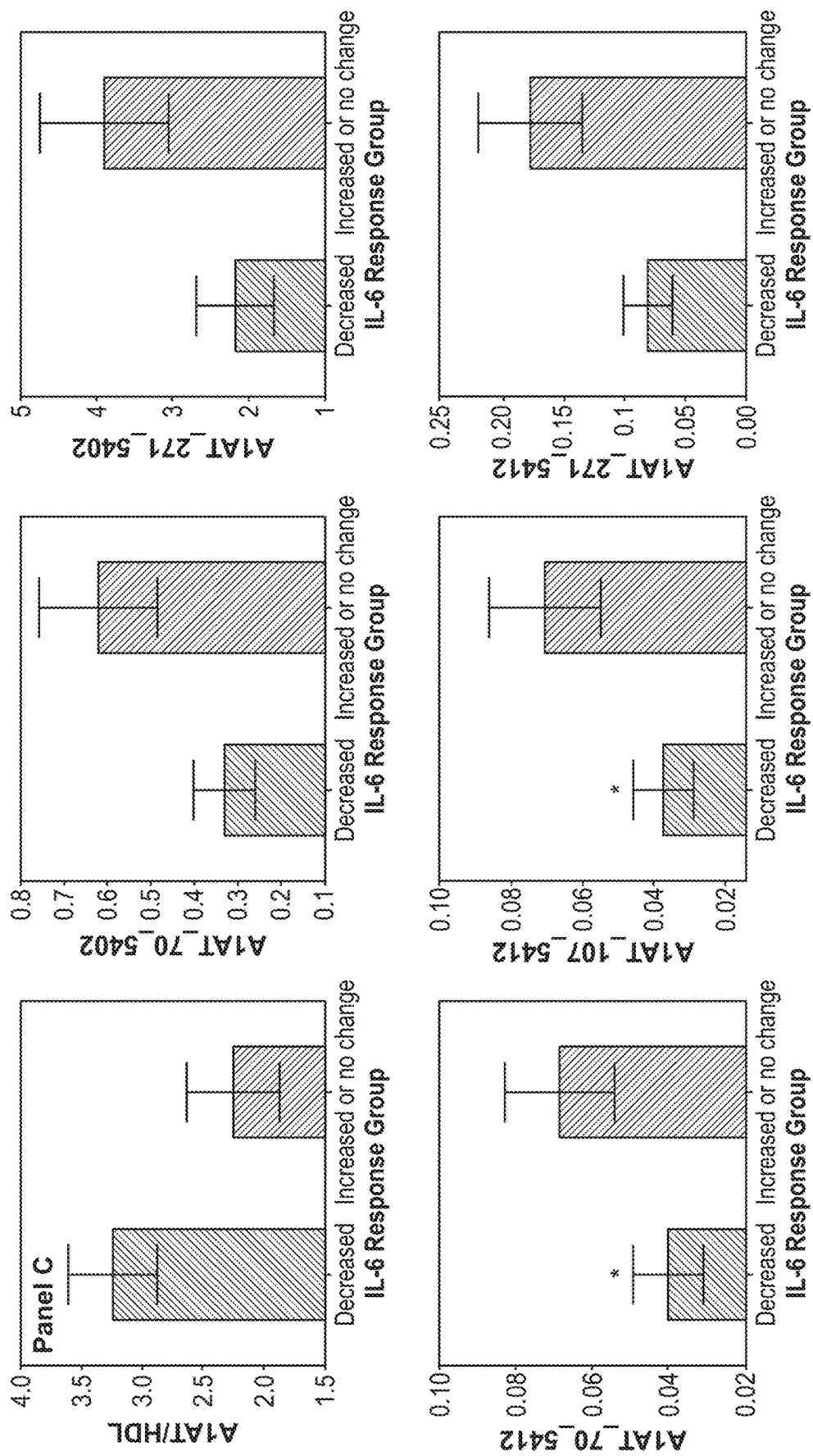

There were no differences in most of the anthropometric and clinical parameters (blood pressure, BMI, weight, etc.) and several of the measured proteins (LBP, ApoA-I, SAA, A2HSG) between the IL-6 response groups (data not shown). ApoC-III was higher in HDL that increased, IL-6 secretion (p=0.043), while the level of the individual mono-sialylated glycan 2221 was lower in HDL that increased IL-6 secretion (p<0.05)(FIG. 7, Pavel A). Mol % monosialylated ApoC-III$_1$, also showed a trend toward being lower in the HDL that increased IL-6 secretion. HDL that increased IL-6 secretion in stimulated monocytes had higher levels of non-sialylated A2HSG isoforms though these did not reach statistical significance (FIG. 7, Panel B). Illustrating this pattern, the individual non-sialylated O-glycan 2200 on site 346 (p=0.017) was lower and the di-sialylated N-glycan 5402 on site 176 (p=0.015) was higher in those HDL that increased IL-6 response. AAT was lower (although it did not reach statistical significance) in HDL that increased IL-6 response (FIG. 7 Panel C), and there were significantly higher levels of two specific desilylated glycans. These two glycans were the mono-fucosylated glycoform 5412, which was higher on two different sites (70 and 107, p<0.05 for both), in HDL that increased IL-6 response. Thus, HDL that increased IL-6 secretion were enriched in the glycan 5412 on A1AT, had lower levels of sialylation in A2HSG as well as lower levels of the glycan 5402 on A2HSG, and increased levels of total ApoC-III and decreased ApoC-III$_1$.

Figure 13:
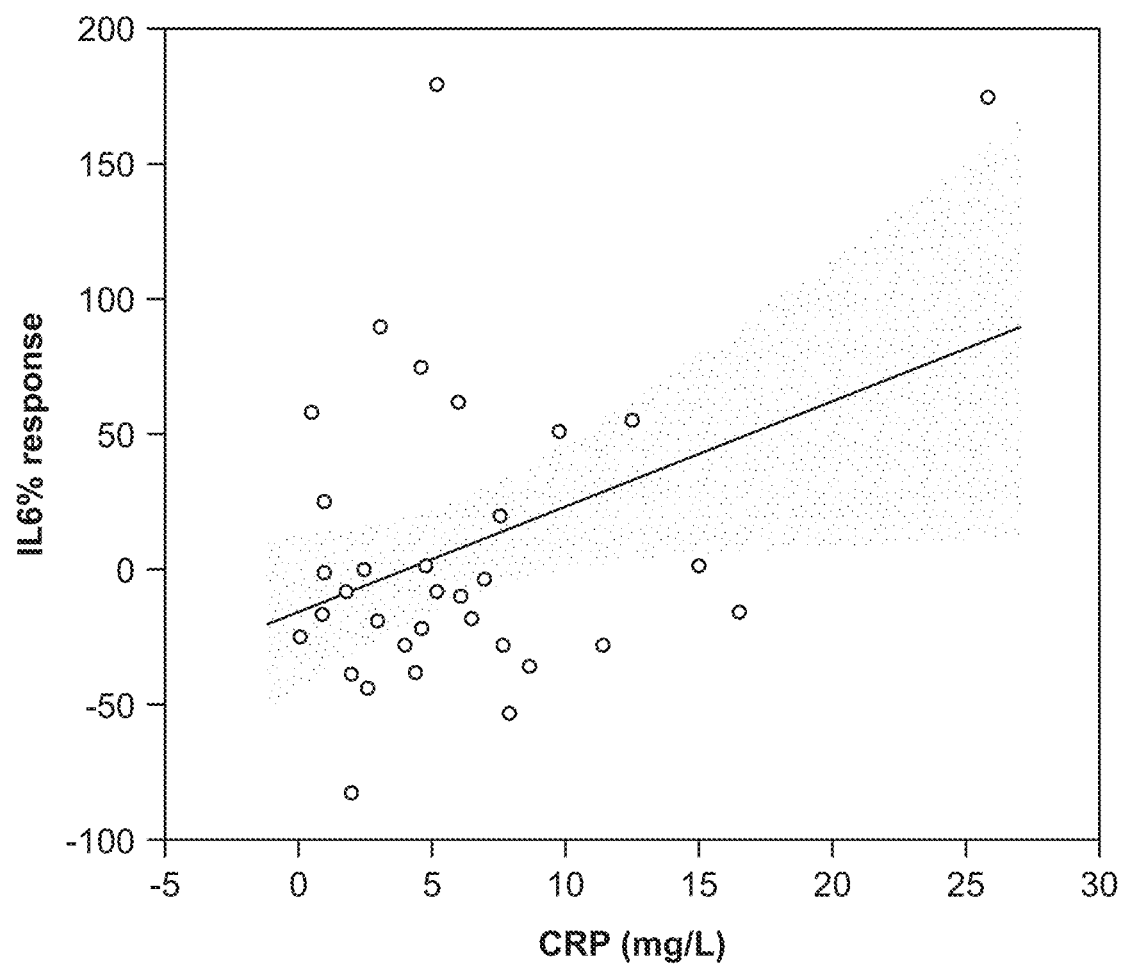
FIG. 13: Positive correlation between IL-6 percent response and CRP (mg/dL) in n=37 patients (diabetic patients on hemodialysis, red dots; and patients with metabolic syndrome, blue dots).

IL-6 response was positively correlated with plasma CRP (p=0.03, r$^2$=0.133)(FIG. 13; correlation calculated with CRP data from the 37 HD and MetS subjects), indicating that the higher the overall inflammation status the more pro-stimulatory the HDL that are associated with that plasma sample.

Figure 8:
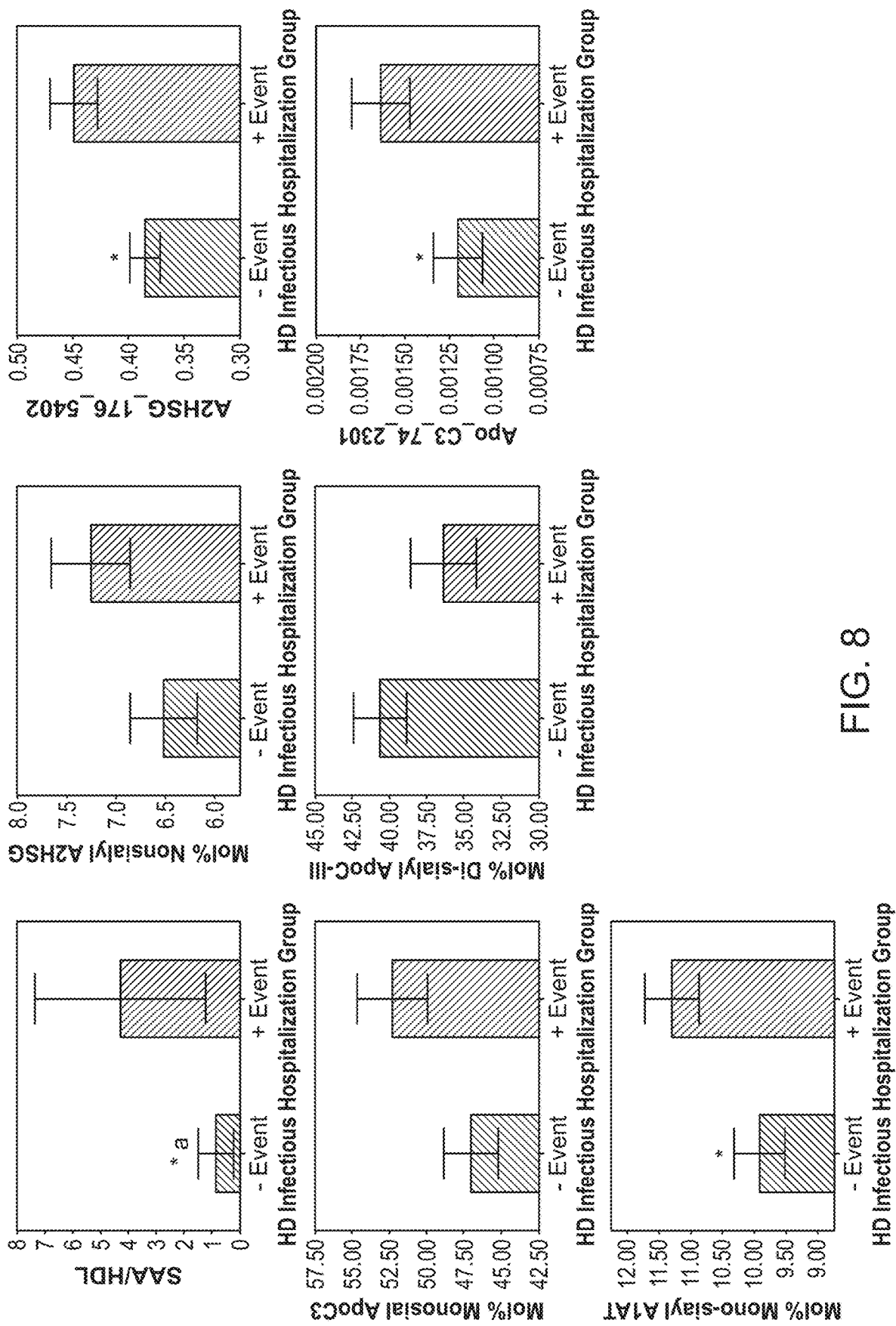
FIG. 8: Differences in protein amounts of serum amyloid A (SAA) and glycosylation patterns of α-2HS-glycoprotein (A2HSG, fetuin A), apolipoprotein C-III (ApoC-III), and αI-antitrypsin (A1AT) by hemodialysis (HD) patient infectious hospitalization group up comparing HDL from subjects who had an infectious hospitalization event within 60 days (+ Event) vs. those who had no event (− Event). Differences are indicated using '*' at p<0.05. "Results for SAA are shown excluding data from 3 outliers.

Differences Between HD Patients With vs. Without Infectious Hospitalization Event We also conducted subgroup analysis on the HD group separating HD patients who went onto be hospitalized for an infectious event within 60 days of their baseline visit (HD+) to those who had no events during almost three years of follow-up (HD−). There were no significant differences between the HD(−) and HD(+) groups in the anthropometric or clinical characteristics (Table 2). The total-amount of SAA was significantly higher in HD+ subject HDL compared to HD−(p<0.05)(FIG. 8) but only when 3 outliers were removed from the analysis. HD+ patients also had higher levels of the individual di-silylated glycan 5402 on site 176 of A2HSG (p<0.05). HDL from HD+ subjects also had higher levels of mono-sialylated ApoC-III but lower levels of di-sialylated ApoC-III, though this did not reach statistical significance while the individual glycan 2301 on site 74 was increased in HD+(p=0.038). The HD+ subjects also had higher levels of mono-sialylated A1AT (p=0.023) and lower levels of trisialyated A1AT though this did not reach statistical significance. Thus, HD+ patients had lower levels of sialylation across the three glycoproteins studied but higher levels of the glycan 5402 at site 176 of A2HSG.

Discussion

Our results indicate that the glycoprotein composition of important HDL-associated proteins does indeed successfully differentiate between clinical groups across the range of insulin sensitivity from normal, to pre-diabetic, to diabetic with renal failure, especially Apo C-III isoforms. HDL from HD patients were enriched in SAA, LBP, ApoC-III, di-sialylated ApoC-III (ApoC-III$_2$) and desialylated A2HSG. Based on the prototypical assay of HDL's immunomodulatory capacity (to modulate IL-6 secretion in LPS-stimulated monocytes), HDL that increased IL-6 secretion were enriched in ApoC-III, di-sialylated glycans on A1AT and desialylated A2HSG, and depleted in mono-sialylated ApoC-III (ApoC-III$_1$. Subgroup analysis on HD patients who experienced an infectious hospitalization event within 60 days vs. those with no event showed that HDL from HD+ patients were enriched In SAA but had lower levels of sialylation across glycoproteins.

ApoC-III glycoforms were key in differentiating between the clinical groups. ApoC-III was higher in HDL of both HD and MetS patients compared to controls, confirming previous reports of increased levels of ApoC-III in HDL of diabetics [Onat, A. et al., *Diabet Med* 26, 981-988, doi: 10.1111/j.1464-5491.2009.02814.x(2009)] and patients with renal failure [Mange, A. et al., *PloS one* 7, e34107, doi: 10.1371/journal.pone.0034107 (2012); Shao, B. et al., *J Proteome Res* 14, 2792-2806, doi:10.1021/acs.jproteome, 5b00060 (2015)]. ApoC-III is known to exist in three different isoforms corresponding to differential migration on a gel due to differences in the number of sialic acid residues. ApoC-III containing no sialic acid is denoted as ApoC-III$_0$, 1 sialic acid as ApoC-III$_1$, and 2 sialic acid residues as ApoC-III$_2$ [Mauger, J. F. et al., *J Lipid Res* 47, 1212-1218, doi:10.1194/r.M500455-JLR200 (2006)]. Our data indicate an enrichment in ApoC-III$_2$ and lose of ApoC-III$_0$ and ApoC-III$_1$ isoforms in HD patients. Apo-III$_2$ isoforms have been shown to associate with LDL particles, in particular small dense LDL particles [Mauger, J. F. et al., *J Lipid Res* 47, 1212-1218, doi:10.1194/jlr.M500455-JLR200 (2006)], and dyslipidemia in HD patients is associated with an enrichment small dense LDL [Deighan, C. J. et al., *Am J Kidney Dis* 35, 852-862(2000)]. Thus, it is possible that the isolated HDL-fractions from the HD subjects were contaminated with small dense LDL. Alternately itis possible that there is an increased exchange of apoproteins between LDL and HDL in the blood of HD patients, or that there is transcriptional regulation or an effect of treatment on ApoC-III glycosylation that leads to this phenotype in HD patients. MetS subjects, in contrast, had significantly higher levels of ApoC-III$_0$ and ApoC-III$_1$ isoforms, and a trend toward lower levels of ApoC-III$_2$ isoforms relative to controls, suggesting a loss of sialylation in ApoC-III compared with controls, similar to previously published observations In MetS patients [Savinova, O. V. et al., *PloS one* 9, e104833, doi:10.1371/journa.pone.0104833 (2014)]. Our data highlight the importance of characterizing the glycosylation profile, with glycan specificity. For example, in spite of the fact that HDL-associated ApoC-III from HD patients were enriched in ApoC-III$_2$ glycoforms in general, the di-sialylated glycan 2212 was depleted, and may be a specific marker of aberrant glycosylation associated with HD.

We observed that HD patients bad the lowest levels of di-sialylated and highest levels of mono- and non-sialylated A2HSG glycans, with MetS subjects intermediate between HD and controls. Thus, in general, loss of sialylation of A2HSG was associated with progressive metabolic and kidney dysfunction. Saroha A et al observed a similar trend of desilylation to be associated with rheumatoid arthritis [Saroha, A. et al, *PloS one* 7, e46374, doi:10.1371/journal.pone.0046374 (2012)]. Yet, HD patients had an increased level of the di-sialylated glycan 5412 on A2HSG, which may be a marker of pathway-specific alterations in glycosylation.

Our data also indicate that HDL that induced a more pro-stimulatory phenotype in monocytes were enriched in ApoC-III but that this ApoC-III was depleted of mono-sialylated glycans, which are the predominant glycoform in normal healthy subjects. Similarly, we observed a loss of sialylation on A2HS in HDL that induced a pro-stimulatory phenotype in monocytes. In contrast, HDL tat induced a pro-stimulatory phenotype were enriched in two di-sialylated glycans (5402 and 5412) across multiple N-glycosilation sites of A1AT. However, since we did not find a significant-difference in the mol % of di-sialylated glycans in A1AT, it is possible that rather than a general trend toward higher sialylation of A1AT, these is a specific change in the content of these two specific di-sialylated glycans on A1AT that affects the functionality of HDL. A1AT is known as an acute phase reactant that has multiple functions including its well-known antiprotease function, as well as newer functions in modulating immune response, generally in the direction of suppressing immune activation and reducing inflammatory signaling (reviewed in Hunt, J. M & Tuder, R., *Curr Mol Med* 2, 827435 (2012)).

Our data suggest that HDL glycoproteomic profiling has the potential lead to discoveries into mechanisms regulating the immunomodulatory function of HDL. More studies are needed, especially ones powered to account for gender and age in addition to clinical characteristics, to determine the aspects of HDL glycoprotein composition that specifically affect HDL's immunomodulatory function. In addition, in this study we used a prototypical assay of HDL's immunomodulatory capacity using an LPS-stimulated monocyte model, yet it is known that HDL interact with a brood array of immune cell types, with a wide range of specific immunomodulatory effects (reviewed in Catapano, A. L. et al., *Cardiovasc Res* 103, 72-383, doi:10.1093/cvr/cvul50 (2014)). A larger repertoire of HDL immunomodulatory functional assays is needed to more comprehensively characterize the effects of changes in HDL composition on its capacity to modulate the immune system.

In our study we found increased levels of SAA in HDL from HD patients who had an infectious hospitalization event within 60 days. Previous studies have found the presence of SAA on HDL to be associated with loss of anti-inflammatory capacity [Van Lenten, B. J. et al., *J Lipid Res* 48, 2344-2353, doi:10.1194/jlr.M700138-JLR200 (2007); Van Lenten, B. J. et al., *J Clin Invest* 96, 2758-2767, doi:10.1172/JCI118345 (1995)], and increased binding to vascular proteoglycans [Chiba, et al., *Arteriosclerosis, thrombosis, and vascular biology* 31, 1326-1332, doi: 10.1161/ATVBAHA.111.226159(2011)]. Our results also indicate that HDL isolated from HD patients who went on to have an infectious hospitalization event were generally depleted of sialic acid across all three glycoproteins characterized. These data support the hypothesis that loss of sialic acid might be associated with loss of protection against infection.

The effects of sialylation on protein function have been documented. For example, it has been demonstrated that immunoglobulin (Ig)glycosylation is linked with the binding affinity of the Ig to its receptors on immune cells (reviewed in Maverakis, E. et al., *J Autoimmun* 57, 1-13, doi:10.1016/j.jaut.2014.12.002 (2015)). Fucosylated, sialylated N-glycans on Ig are associated with anti inflammatory properties compared to undecorated, ungalactosylated N-glycans, because these modifications modulate the binding affinity of the IgG to activating vs. inhibiting Fc receptors Maverakis; E, et al., *J Autoimmun* 57, 1-13, doi:10.1016/j.jaut.2014.12.002(2015). A2HSG (also known as fetuin A) and A1AT were found to be differentially glycosylated in chronic pancreatitis and pancreatic cancer [Sarrats, A. et al., *Proteomics Clin Appl* 4, 432-448, doi:10.1002/prca.200900150 (2010)]. However, to our knowledge, our study is the first to examine the effects of glycosylation, particularly site-specific glycosylation, of HDL-associated proteins on the immunomodulatory function of HDL.

Our study has several limitations. Firstly, this was a pilot study with a relatively small sample size in each clinical group, which may explain why some of our results did not reach statistical significance, and also requires fewer studies to corroborate our findings. We did not have many of the clinical measurements including LDL-C, TG, CRP for control subjects. In addition to larger sample size, future studies need to examine the effects of gender and ago, in addition to other clinical characteristics (e.g. type 1 diabetes) and lifestyle factors (e.g., smoking) on HDL compositional and functional profiles. In this study we measured the secretion of IL-6 as a prototypical cytokine response in LPS-stimulated monocytes. However, future studies should examine a more comprehensive profile of cytokines, chemokines, adhesion molecules, and other inflammatory mediators, as well as other inflammatory stimuli and in additional immune cell types to gauge the impact of HDL composition on its ability to modulate immune response.

CONCLUSIONS

We found that HDL glycoprotein and distinct site-specific glycosylation were characteristic of clinical groups, with largo differences and characteristic glycopeptide profiles among diabetic patients undergoing HD, subjects with MetS and healthy controls. Generally, loss of sialic acid on an array of glycopeptides was associated with disease, except that in HD patients, HDL was enriched in di-sialylated ApoC-III isoform (ApoC-II$_2$) and depleted in the less sialylated ApoC-III$_1$ and ApoC-III$_0$ isoforms. Yet specific glycans at specific sites did not follow these general patterns, highlighting the importance of comprehensive, site-specific glycoprofiling for biomarker discovery. Although, whether subjects were healthy or unhealthy strongly influenced their HDL glycoprofiles, the subjects' clinical characteristics were not indicative of whether their HDL were pro-vs anti-stimulatory. Instead, the glycoprofiles of key HDL-associated glycoproteins differeniated between those whose HDL induced vs. suppressed IL-6 secretion in stimulated monocytes. Finally, our data suggest that HDL glycoprotein profiles could potentially be predictive of susceptibility to serious infectious events. Together, these findings implicate glycoprofiling of HDL particles as a tool for developing biomarkers of disease, as well as understanding the mechanisms that mediate the immunomodulatory function of HDL particles.

TABLE 1

Characteristics of the subjects within each group: healthy controls, diabetic patients on hemodialysis (HD), and subjects with metabolic syndrome (MetS).

| | Control (n = 13) Mean ± SD | HD (n = 24) Mean ± SD | MetS (n = 13) Mean ± SD |
|---|---|---|---|
| BMI (kg/m2) | 22.71 ± 2.96[a] | 29.18 ± 5.92[b] | 31.77 ± 3.30 [b] |
| Systolic Blood pressure (mmHG) | 114.39 ± 11.19 [a]| 151.33 ± 20.50 [b]| 126.12 ± 17.54 [a] |
| Diastolic Blood pressure (mmHg) | 72.83 ± 8.82 | 79.88 ± 11.78 | 76.96 ± 11.94 |
| Age (y) | 33.33 ± 10.21 [a] | 55.00 ± 13.45 [b] | 44.69 ± 13.31[a,b] |
| Weighted Average HDL size (nm) | 14.65 ± 7.69 | 17.68 ± 9.26 | 11.41 ± 7.48 |
| IL-6 (% response) | −6.07 ± 17.07 | 12.91 ± 66.56 | −11.61 ± 25.42 |
| CRP (mg/L) | | 19.83 ± 43.57 | 4.99 ± 3.88 |
| TG (mg/dL) | | 115.83 ± 70.26 [a]| 174.24 ± 57.94 [b] |
| Composition of isolated HDL fraction | | | |
| Cholesterol (mg/dL) | 110.51 ± 42.83 [a] | 74.77 ± 24.61 [b] | 74.24 ± 25.00 [a,b] |
| A1AT^ | 2.22 ± 1.72 | 3.43 ± 2.03 | 2.62 ± 1.99 |
| A2HSG^ | 0.36 ± 0.17 [a,b] | 0.37 ± 0.17 [a] | 0.61 ± 0.38 [b] |
| ApoC-III^ | 13.47 ± 3.43 [a] | 34.26 ± 16.25 [b] | 25.54 ± 11.77 [b] |
| SAA^ | 0.04 ± 0.02 [a] | 7.74 ± 2.56 [b] | 0.17 ± 0.14 [b] |
| LBP^ | 20.15 ± 8.85 [a] | 50.78 ± 24.70 [b] | 35.44 ± 15.55 [b] |
| ApoA-I^ | 0.91 ± 0.39 | 0.91 ± 0.49 | 0.66 ± 0.26 |

Significant differences '[a]' and '[b]' superscripts indicate individual group differences at p < 0.05) using van der Weardan's non parametric test, followed by Steel-Dwaas multiple comparison tests;
^indicates that it was normalized to cholesterol (mg/dL) in the HDL fraction.

TABLE 2

Characteristics of the diabetic patients on hemodialysis who did not have an infectious event (HD−) vs. those who had an infectious hospitalization event within 60 days (HD+).

| | HD(−) (n = 12) Mean ± SD | HD(+) (n = 12) Mean ± SD |
|---|---|---|
| BMI (kg/m2) | 28.95 ± 6.10 | 29.41 ± 6.00 |
| Systolic Blood pressure (mmHG) | 159.08 ± 14.74 | 143.58 ± 22.98 |
| Diastolic Blood pressure (mmHg) | 82.58 ± 11.11 | 77.17 ± 12.26 |
| Age (y) | 53.64 ± 14.99 | 56.88 ± 11.72 |
| Weighted Average HDL size (nm) | 21.98 ± 8.51 | 13.38 ± 8.14 |
| IL-6 (% response) | −6.00 ± 29.04 | 31.83 ± 87.41 |
| CRP (mg/L) | 6.30 ± 5.13 | 19.83 ± 43.57 |
| HDL-C (mg/dL) | 57.38 ± 16.52 | 50.67 ± 13.16 |
| TG (mg/dL) | 109.46 ± 49.94 | 115.83 ± 70.26 |
| Composition of isolated HDL fraction | | |
| Cholesterol (mg/dL) | 80.69 ± 19.68 | 68.84 ± 28.32 |
| A1AT^ | 3.20 ± 1.55 | 3.65 ± 2.47 |
| A2HSG^ | 0.32 ± 0.09 | 0.41 ± 0.21 |
| ApoC-III^ | 30.85 ± 12.55 | 37.66 ± 19.20 |
| SAA^ | 0.83 ± 2.21 | 4.28 ± 10.68 |
| LBP^ | 44.45 ± 15.76 | 57.11 ± 30.65 |
| ApoA-I^ | 0.90 ± 0.47 | 0.92 ± 0.53 |

^indicates normalization to cholesterol (mg/dL) in the HDL fraction.

Example 2

Figure 9:
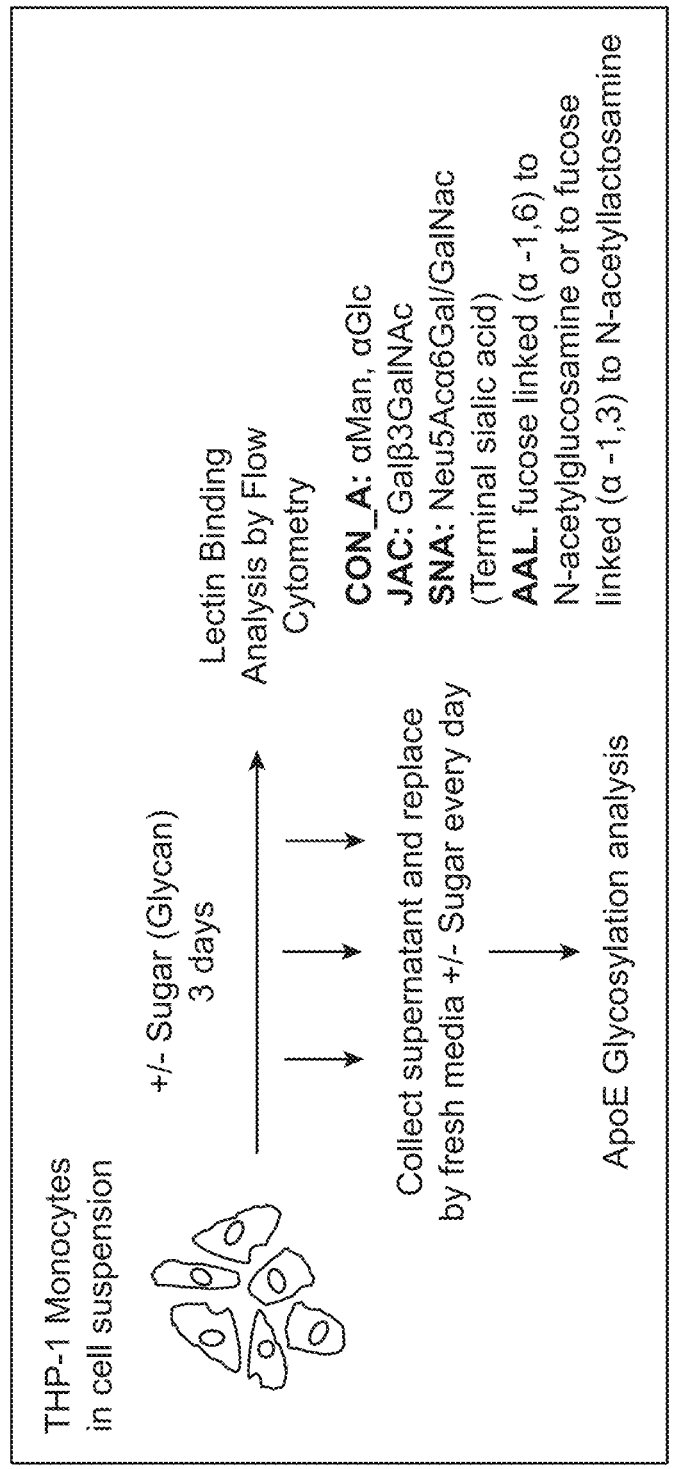
FIG. 9 shows a workflow example for determining the effect of sugars on ApoE glycosylation.

Effect of Monosaccharide Supplementation on THP-1 Monocyte Cell Surface Glycan Composition Study Design THP-1 cells (monocyte cell line) were incubated with different sugars (i.e. monosaccharides) for 3 days. Lectin arrays were used to detect changes in the cell surface glycan composition. Secreted HDL from the cell supernatant (monocytes secrete their own HDL) was isolated and then analyzed to determine the glycan composition. See FIG. 9.

Lectins were Used to Detect Glycan Composition Changes:
  ConA (Concanavalin A): binds internal and nonreducing terminal α-D-mannosyl (αMan) and α-D-glucosyl groups (αGlc)
  JAC (Jacalin): binds galactose-containing O-glycoproteins (Galβ3GalNac)
  SNA (*Sambucus nigra*): binds sialic acid attached to terminal galactose in α-2,6 and to a lesser degree, α-2,3 linkage (Neu5Acα6Gal/GalNac)
  AAL (Aleuria auanda lectin): binds fucose linked (α-1,6) to N-acetylglucosamine or to fucose linked (α-1,3) to N-acetyllactosamine related structures, exposed core (α-1, 6) and outer arm (α-1, 2 or α-1, 3) linked fucose moieties.

Sugar Treatments:
  L-fucose: Tested 2 doses: 300 umol/L (physiologic) and 100 mmol/L. (Marquardt T, *Blood*, December 15; 94(12):3976-85, 1999): Named L-Fuc Low and L-Fuc High
  Fructose: Tested 2 doses: 27 mmol/L (physiologic) and 100 mmol/L. (Hui H, *Pancreas*, August 38(6): 706-12, 2009); Named Fruc Low and Fruc High
  N-acetylglucosamine (GlcNAc): Tested 1 dose: 100 mmol/L. (Villiger TK, Controlling the time evolution of mAb N-finked glycosylation, Part I: Microbioreactor experiments, *Biotechnol Prog*, September; 32(5):1123-1134, 2016)
  Galactose: The two doses for the galactose treatment in the glycan array experiments were: 150 mmol/L and 75 mmol/L. (Villiger TK, Controlling the time evolution of mAb N-linked glycosylation, Part II: Model-based predictions, *Biotechnol Prog*, September; 32(5):135-1148, 2016)

Results

Galactose Treatment
  SNA birding increased on both doses: galactose increased the amount of terminal sialic acid on the glycans (especially α-2,6 sialic acid residues).
  JAC binding decreased on low dose, increased on high dose: galactose treatment deceased the amount of terminal galactose containing glycans on low dose but increased the amount of terminal galactose containing glycans on high dose.
  AAL binding increased on high dose: galactose treatment increased the amount of fucosylated glycans.
  ConA binding increased on high dose: galactose treatment increased the amount of glucose or mannose-terminated glycans.

N-Acetylglucosamine (GlcNac) Treatment
  SNA binding did not change: GlcNac treatment did not affect sialylation.
  JAC binding decreased: GlcNac treatment decreased the amount of terminal galactose containing glycans.
  AAL binding decreased: GlcNac treatment decreased the amount of fucosylated glycans.
  ConA binding decreased; GlcNac treatment decreased the amount of glucose or mannose-terminated glycans.

Fructose Treatment
  SNA binding decreased in response to low dose only: fructose treatment decreased sialylation but only at low dose, no effect on high dose.
  JAC binding decreased on high dose only: fructose treatment decreased the amount of terminal galactose containing glycans on high dose only.
  AAL binding decreased on low dose more than on high dose: fructose treatment decreased the amount of fucosylated glycans on low dose.
  ConA binding decreased: fructose treatment decreased the amount of glucose or mannose-terminated glycans.

Fucose Treatment
  SNA binding increased in response to both doses (dose-dependent) fucose treatment increased sialylation in a dose-dependent manner.
  JAC binding decreased more on low dose than on high dose: fucose treatment decreased the amount of terminal galactose containing glycans more on low dose than on high dose.
  AAL binding decreased in dose-dependent manner: fucose treatment decreased the amount of fucosylated glycans in response to low dose and even more so in response to high dose.
  ConA binding decreased: fucose treatment decreased the amount of glucose or mannose-terminated glycans on both doses.

Figure 10:
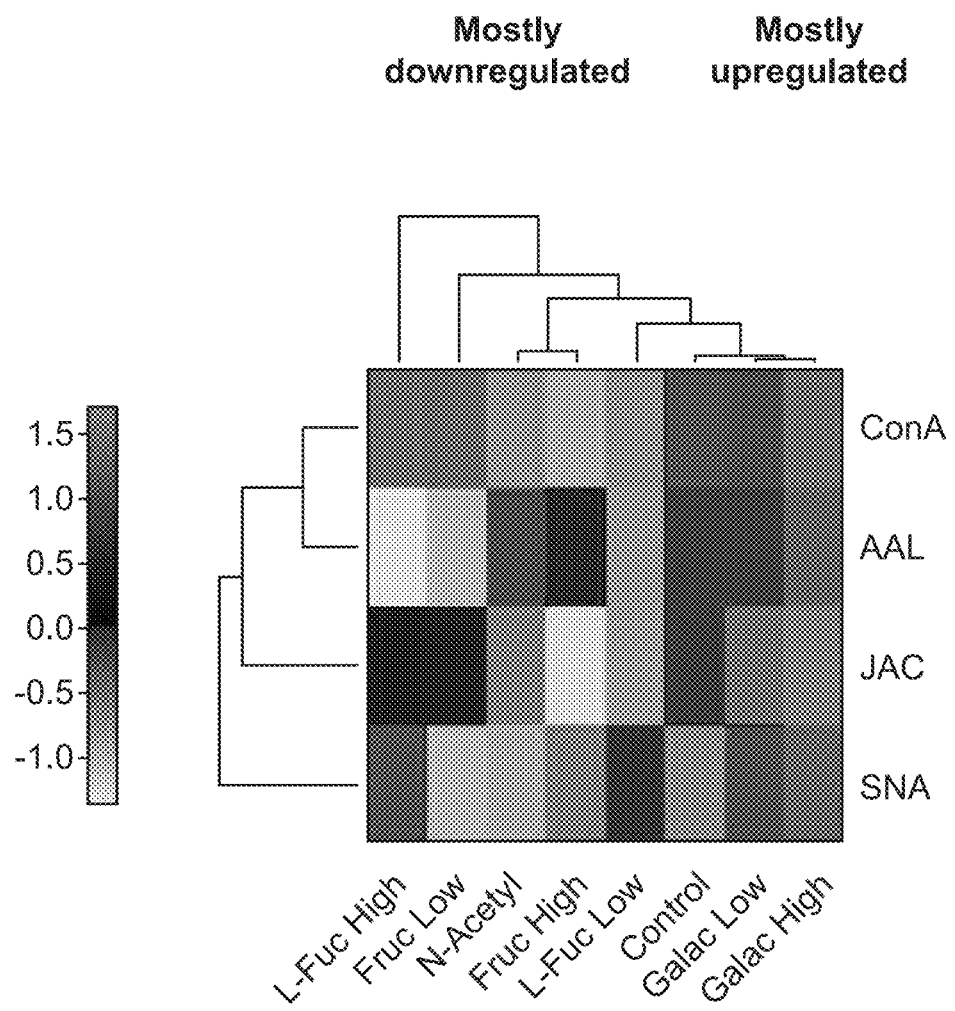
FIG. 10 summarizes the observed effect of various sugars on glycosylation in monocytes.
Figure 11:
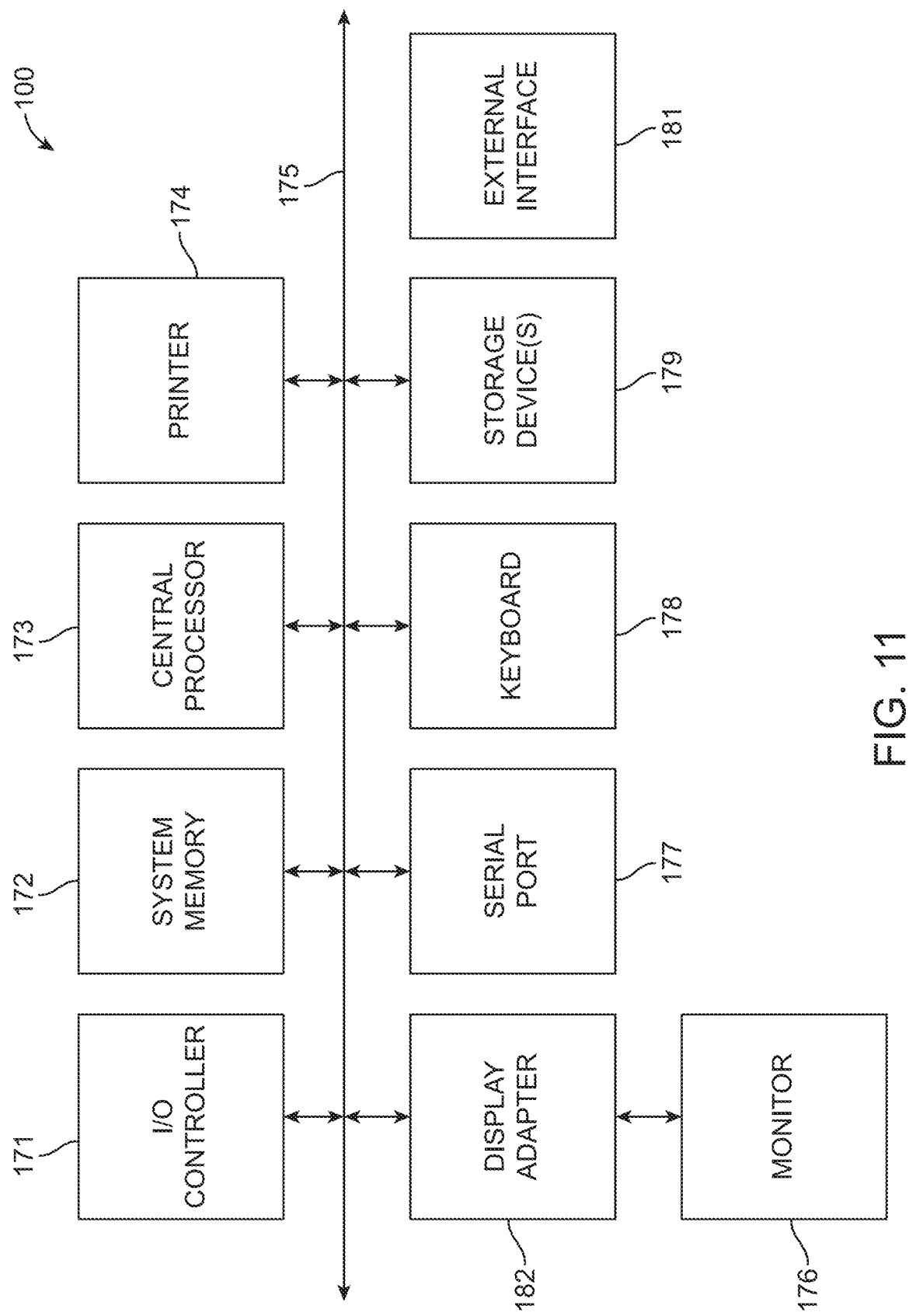
FIG. 11 shows a block diagram of an example computer system 100 usable with system and methods according to embodiments of the present disclosure.

These results (summarized in FIG. 10) indicate that both fucose and galactose treatment increases sialylation of proteins whereas fructose decreases the sialylation of proteins. If the glycosylation patterns are similarly affected in HDL proteins as they are in these cell surface proteins, these monosaccharide treatments would alter the glycan composition of HDL, thereby affecting their and inflammatory capacity.

Example 3

The large surface area of the gastrointestinal tract provides abundant opportunities for direct contact with substances in the environment Along its inner wall, at the interface of the intestinal lumen and mucosa, a single layer of epithelial cells mediate the passage f a wide composite of extracellular material, including nutrients from foods, products of microbial fermentation, as well as toxins. Proper growth and vitality of the epithelial monolayer is therefore critical for maintaining a healthy gut. A major proportion of their extracellular membrane proteins are uniquely and densely glycosylated with additions of saccharide chains. The presented array of glycans is vastly heterogeneous, wherein the degree of branching and composition are governed by the cooperative and non-templated actions of glycosidases and glycosltransferases (Aebi M et al., *Trends in biochemical sciences*, 35:7442 (2010)). Interruptions of the biosynthetic pathway at the gene or protein levels can potentially alter a multitude of structures that are expressed on the cell surface, which can in turn have long-standing consequences.

Among its explored roles, glycosylation in the gastrointestinal tract fosters host-microbe relationships, providing a source of energy in favor of the colonization of the natural gut flora or pathogens whose glycosyl hydrolases and receptors confer a survival advantage (Marcobal A et al., *Glycobiology*, 23:1038-1046 (2013); Moran A P et al., *Gut*, 60:1412-1425 (2011); Tailford L E et al., *Frontiers in genetics*, 6:81 (2015)). At a more fundamental level, considerable evidence suggests that the type of glycans presented on proteins participate in regulating key biological processes such as protein folding, stability, and localization as well as in determining biological activity (Cumming DA., *Gycobiology*, 1:115-130 (1991); Helenius A, Aebi M, *Sci-* ence, 291:2364-2369 (2001); Moremen K W et al., *Nature reviews. Molecular cell biology*, 13:448-462 (2012); O'Connor S E et al., *Chemistry & biology*, 3:803-412 (1996); Rasmussen J R, *Current opinion in structural biology*, 2:682-686 (1992); Stowell S R et al., *Annu Rev Pathol*, 10:473-510 (2015)). Given that a synergistic relationship between glycans and the underlying proteins exists, alterations that occur in intestinal cell surface glycosylation may not only curb or intensify extracellular interactions but also affect the cell's physiology. However, the contributors of intestinal glycosylation changes or the prolonged effects of differential expression are poorly understood. To assess glycan-environment relationships, we selected well established and widely studied human cell lines, Caco-2 and HT-29, which exhibit classical characteristics that model small intestinal absorptive epithelial calls upon reaching confluence (Hilgers A R er al., *Pharmaceutical research*, 7:902-910 (2001); Pinto M et al., *Biol Cell*, 47:323-330 (1903); Rousset M, *Biochimie*, 68:1035-1040 (1986)). Controlled changes in media composition, pH, and maintenance were made to understand which environmental stimuli significantly alter the intestinal glycosylation machinery. Assessment of these molecular changes is often undetectable under the microscope and requires sensitive analytical tools, which are continuing to be developed for large-scale system-wide studies.

Results

Metabolism of Dietary Components Route Glycan Expression

We examined whether supplementation of free monosacchaides derived from diet changes N-glycosylation outcomes on the intestinal cell-surface at concentrations relevant to physiological conditions. Changes in glycosylation were assessed by globally releasing glycans from membrane proteins extracted from fully differentiated (Caco-2) and partially differentiated (HT-29) intestinal epithelial cells and analyzing the mixture by porous graphitized carbon (PGC)-LC-MS. This approach allowed us to derive comprehensive maps encompassing over 300 unique structures and monitor their expression levels individually. The glycan profile under normal growth conditions was used as a frame of reference with which to compare the glycome at varied environments.

Figure 14:
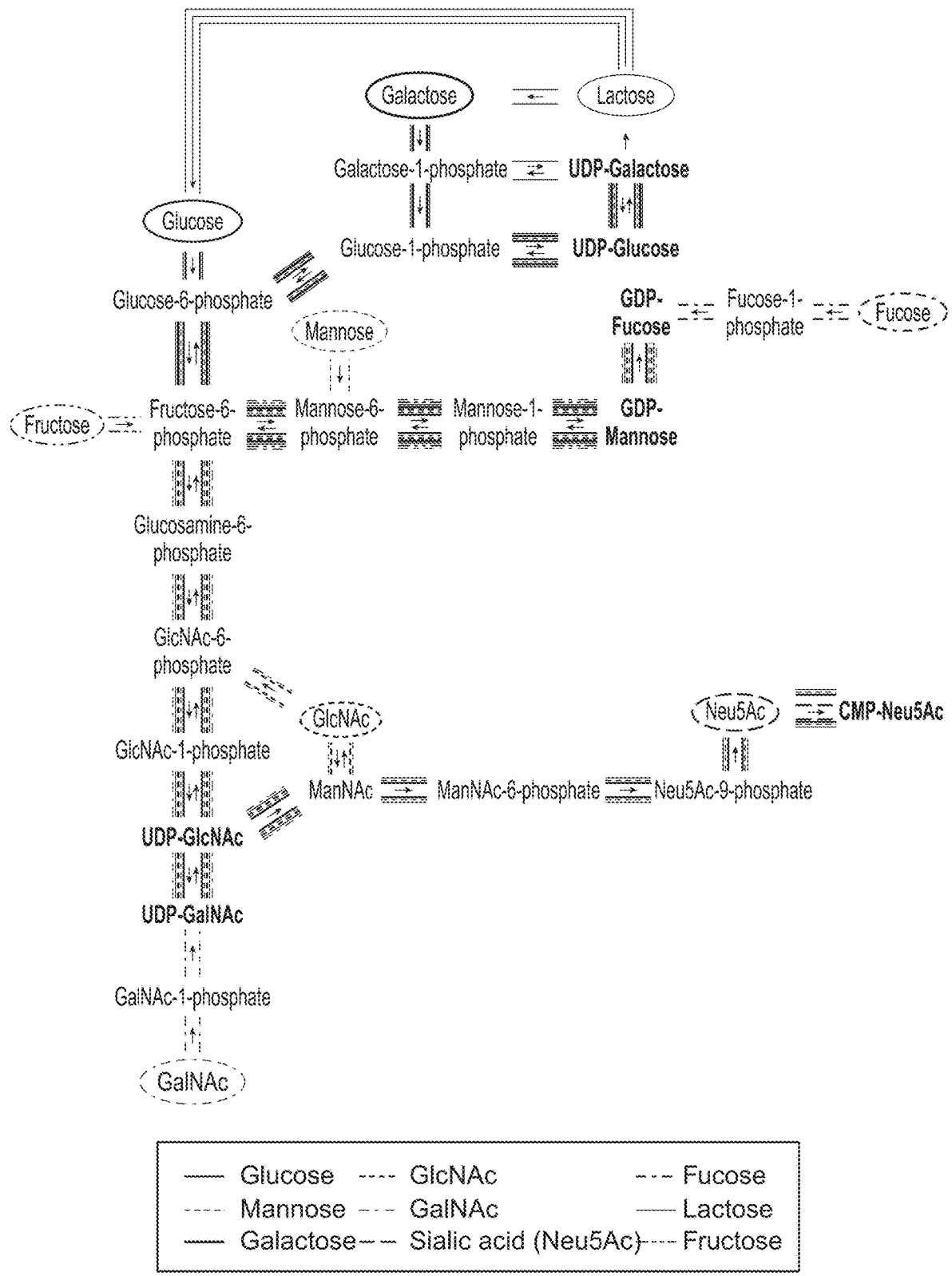
FIG. 14. An outline of the interconversion and activation pathways of exogenously introduced human monosaccharide components of diet. Significant routes from this study are highlighted by colored lines corresponding to each monosaccharide. Activated sugar forms are bold faced.
Figure 15A:
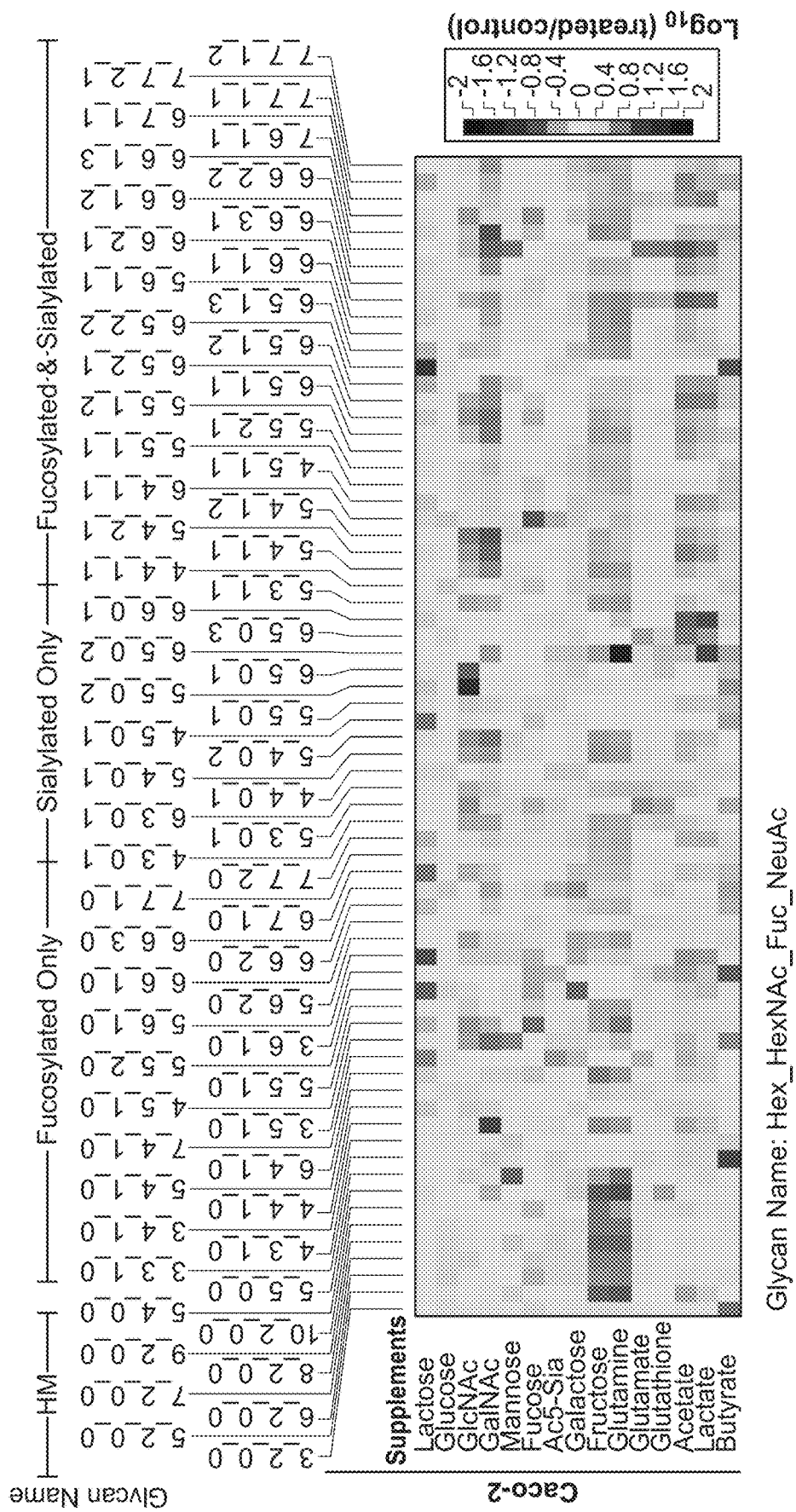
FIG. 15A-C. Changes in Caco-2 and HT-29 cell surface glycan abundances following supplementation. (A) Heatmap of altered glycan compositions from untreated to treated Caco-2 and HT-29 cells. A threshold of relative abundances>0.5% and fold changes>2 was used. Data are represented as the log value of the fold change. Glycan mass increases from left to right within each group. Naming is as follows: Hex_HexNAc_Fuc_NeuAc. (B-C) Relative distribution of fucosylation and sialylation in Caco-2 and HT-29 cells after treatment. Each feature is separated according to number of residues.

Abundant in nearly all carbohydrate-containing foods, glucose (Glc) is a soluble hexose sugar that can be efficiently metabolized by cells (FIG. 14) and utilized as a primary energy source. Delivery of glucose to the proximal gut is highly regulated in heathy individuals, keeping intraluminal glucose levels fairly constant regardless of dietary load, ranging from 0.2 to 50 mM in the mammalian small intestine (Ferraris R P et al., *Am J Physiol*, 259: G822-G837 (1990)). After high glucose supplementation (25 mM), we observed minimal changes in the groups of glycans presented on Caco-2 across all replicate samples (FIG. 19). Within groups, individual glycan compositions showed no more than 1.7-fold changes (FIG. 15A). On HT-29 cells, the abundances of non-decorated complex/hybrid glycans decreased by 20% ($p<0.05$) following treatment (FIG. 19). However, they constitute a minor component of the cell surface and sum to less than 4% of the total N-glycans. Overall, a high glucose environment did not have a substantial impact on cell surface N-glycosylation, indicating that absorbed glucose is ubiquitously interconverted into other activated monosaccharide forms without favoring specific biosynthetic routes (FIG. 14). Similar to glucose, mannose (Mau) is found is all glycoprotein-containing food products and is equally an important precursor for N-glycan synthesis. Predictably, no major changes were observed in Caco-2 cell surface glycans upon treatment with mannose, consistent with the effects observed by glucose treatment (FIG. 19). The lack of discrete changes provides support that exogenous mannose likewise is readily utilized by multiple metabolic routes. In fact, its activated phosphorylated form (Mau-6-P) can be converted into all of the monosacharide constituents transferred onto the nascent N-glycan chain (FIG. 14). In comparison, HT-29 cells grown in the presence of free mannose showed significant changes ($p<0.05$) collectively in high mannose type glycans (FIG. 19). When glycan species were evaluated individually, slight increases in Man 3, Man 7, and Man 9 were observed-(FIG. 15A). This data demonstrates that mannose utilization is better with exogenous mannose than via glucose interconversion, supporting earlier beliefs (Ichikawa M et al., *The Journal of biological chemistry*, 289:6751-6761 (2014)).

Figures 15B, 15C:
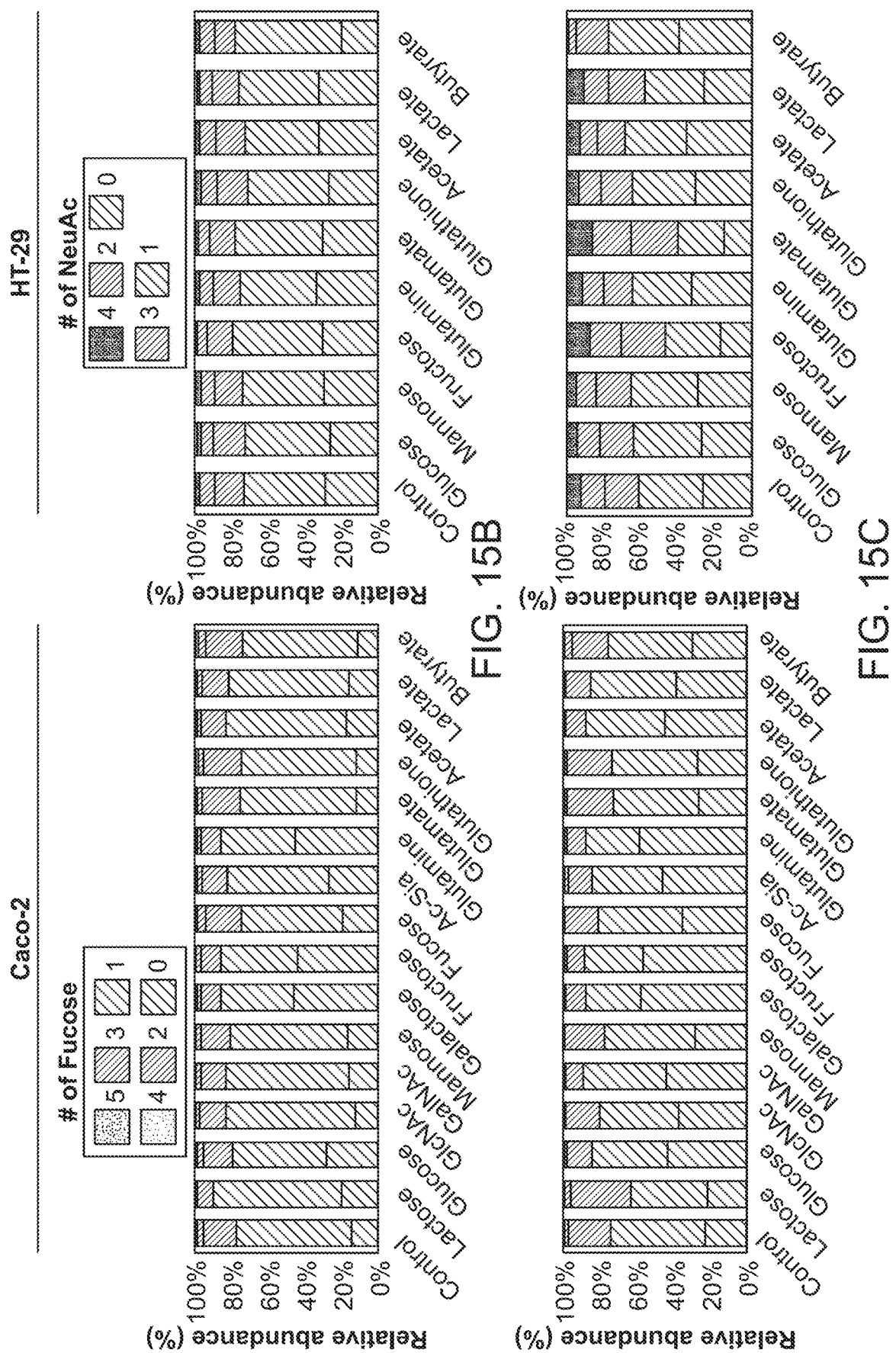

Although elementally similar to glucose, galactose (Gal), a common component of dairy and plant-based carbohydrates, is not readily metabolized and must first be converted. Unlike the effects observed by glucose treatment significant Increases ($p<0.05$) were observed for all high mannose (Man 3-Man 9)(FIG. 15A) and non-decorated complex/hybrid types of N-glycans (e.g., $Hex_5HexNAc_4$ and $Hex_5HexNAc_5$) in galactose-treated Caco-2 cells (FIG. 15A). Correspondingly, the relative abundances of fucosylated and sialylated glycans decreased after treatment by 12-28% ($p<0.05$)(FIG. 19). This effect is shown more clearly by the change in abundances of individual glycans. In untreated controls, afucosylated and asialylated glycans constituted 15% and 23%; respectively of all complex/hybrid glycans (FIGS. 15R and 15C). In contrast, the same group made up 46% and 58%, respectively, of all complex/hybrid glycans in galactose-treated cells. To validate the utility of using glycan profiles in describing discrete biological effects, we assessed the reproducibility of each treatment. Glycan profiles of biological replicates after galactose treatment demonstrated high sampels and instrument stability (FIG. 12).

A derivative of glucose, N-acetylglucosamine (GlcNAc) is also found, in all glycoprotein food products and involved in the biosynthesis of both CMP-N-acetylneuraminic acid (Neu5Ac; NeuAc) and GDP-fucose (Fuc) through divergent pathways (Keppler O T et al., *Science*, 284:1372-1376 (1999); Snider M D, *Curr Protoc Cell Biol*, Chapter 7:Unit 7 8 (2002)). When supplemented with 25 mM GlcNAc, fucosylated glycans collectively increased by 61.2% ($p<0.05$) while sialylated glycans decreased by 53.9% ($p<0.05$)(FIG. 19). Specifically, cells showed higher expression of monofucosylated types (e.g., $Hex_3HexNAc_5Fuc_1$, $Hex_4HexNAc_5Fuc_1$, $Hex_6HexNAc_7Fuc_1$, and $Hex_6HexNAc_7Fuc_1NeuAc_1$) and lower expression of desialylated structures (e.g., $Hex_5HexNAc_5NeuAc_2$, $Hex_5HexNAc_4NeuAc_2$, and $Hex_5HexNAc_4Fuc_1NeuAc_2$) (FIGS. 15A, 15B, and 15C). These results show that formation of GDP-Fuc is likely favored over CMP-Neu5Ac when excess extracellular GlcNAc is supplied to cells (FIG. 14). Closely integrated into GlcNAc metabolism the monosaccharide N-acetylgalactosamine (GalNAc) may also partake in glycoprotein synthesis through the conversion of UDP-GalNAc to UDP-GlcNAc. In support of this route, the glycan changes observed after GalNAc addition resembled those observed on GlcNAc-treated cells, where the abundances of fucose-containing structures increased (120%, $p<0.05$) and the abundances of sialic acid-containing structures decreased (31.9%, $p<0.05$)(FIG. 19). Compared with GlcNAc, changes resulting from GalNAc supplementation were more intense for purely fucosylated species. This effect is predominantly attributable to the heightened expression of two core-fucosylated, agalactosylated compounds, $Hex_3HexNAc_4Fuc_1$ and $Hex_3HexNAc_5Fuc_1$, which increased 13-fold and 7-fold, respectively (FIG. 15A). Contrary to GlcNAc treatment, addition of GalNAc resulted in a marked increase in non-decorated complex/hybrid structures (234%, $p<0.05$), particularly of a biantennary compound, $Hex_5HexNAc_4$ (FIG. 19).

We next investigated how-fucose, the only levorotatory monosaccharide utilized by mammalian systems, is incorporated onto glycoproteins from extracellular sources. When Caco-2 cells were supplemented with high concentrations (25 mM) of fucose, neither the total levels nor the degree of fucosylation deviated significantly from what was observed in the control (FIG. 19 and FIG. 15B). Based on compound-by-compound analysis, we found a select group of fucosylated structures that increased, including $Hex_4HexNAc_5Fuc_1$ and $Hex_5HexNAc_5Fuc_2$, and $Hex_3HexNAc_6Fuc_1$(FIG. 15A). We observed a parallel decrease in select fucosylated structures that were also sialylated (e.g., $Hex_6HexNAc_4Fuc_1NeuAc_1Hex_6HexNAc_7Fuc_1NeuAc_1$). In complement, an overall decrease in sialylated glycans accompanied treatment (FIG. 19). The earlier observations that mannose, GlcNAc, and GalNAc addition-affects the production of fucosylated glycoproteins indicates that cytosolic activation to GDP-Fuc does in fact occur in Caco-2 and HT-29 cells. Together, these results support the metabolic pathway wherein fucose is not rapidly converted into other activated monosaccharide forms (FIG. 14).

Among the most structurally unique and widely studied monosaccharides, sialic acids. (Neu5Ac; NeuAc; Sia) are metabolically produced by condensation of phosphorylated N-acetylmannosamine (ManNAc-6-P)(FIG. 14). Although free sialic acids are present in nature, diffusion across the membrane is limited due to their anionic charge and most exist as oligo-O-acetylated forms. Therefore, in this study, we utilized per-O-acetylated sialic acid (2,4,7,8,9-penta-O-acetyl N-acetylneuraminic acid (Ac5-Sia)) in concentrations of up to 10 mM, After 72 h, the abundances of sialylated compounds remained relatively unchanged compared to untreated controls. On the contrary, significant increases ($p<0.05$) were observed for monofucosylated glycans (FIG. 15B), primarily for agalactosylated compounds, $Hex_3HexNAc_3Fuc_1$ and $Hex_3HexNAc_6Fuc_1$ (FIG. 15A).

Besides the common monosaccharide building blocks found in glycosylated products, we assessed the effects of fructose, a major ingredient in foods that have high sugar content. Fructose availability in the gut is greatly affected by diet. Luminal fructose concentration in rats fed with high fructose diet was reported to be 26 mM or higher (Kirchner S et al., *American Journal of Clinical Nutrition*, 87:1028-1038 (2008)). Strikingly, Caco-2 growth in high fructose (50 mM) environments resulted in significant increases ($p<0.05$) in the concentrations of high mannose and non-decorated complex/hybrid type N-glycans, producing abundance changes of 511% and 672%, respectively (FIG. 19). The same upregulation was observed for monofucosylated, asialylated glycans that contain less than five GlcNAc residues (FIG. 15A). These include $Hex_3HexNAc_4Fuc_1$, $Hex_4HexNAc_5Fuc_1$, $Hex_6HexNAc_4Fuc_1$, and $Hex_5HexNAc_5Fuc_1$ which each increased more than 4-fold. When taken up by cells, fructose is converted to fructose-6-phosphate, which can then be incorporated onto cell surface glycoproteins by conversion to a variety of monosaccharide donors such as UDP-Glc, UDP-GlcNAc, and GDP-Man (Snider, M. D. 2002)(FIG. 14). In Caco-2, fructose supplementation favored mannosylation. While exogenous fructose directly participates in de nova glycan biosynthesis, utilization varies by cell type. In contrast to Caco-2, the majority of high mannose and fucosylated glycans in HT-29 cells remained unaltered (FIG. 15A).

Given that monosaccharides from exogenous sources directly participate in the glycosylation pathway, we next determined whether their naturally glycosylated forms have similar metabolic fates upon uptake. Lactose, the major component of milk, is a disaccharide sugar composed of glucose and galactose linked by a beta glycoside bond, which upon consumption can be cleaved by intestinal epithelial cells into the respective monosaccharide parts (FIG. 14). When we supplemented Caco-2 with lactose (70 mg/L), most types of complex/hybrid N-glycans changed following the same trends as under high galactose condition (FIG. 19). For example, fucosylated compounds significantly decreased by 20% ($p<0.05$) in both cases. However, unlike galactose treatment, addition of lactose did not cause dramatic changes in high mannose glycosylation. At the individual, single compound level, meaningful changes in abundances were solely observed in complex or hybrid type glycans that possessed at least one galactose residue (FIG. 15A).

Microbial Byproducts Create Glycan-Altering Environments

During fermentation of dietary fibers, gut microbes produce short chain fatty acids (SCFAs), which are readily absorbed by colonocytes. SCFA concentrations vary longitudinally along the intestines, ranging from 20-40 mM in the terminal ileum, 70-140 mM in the proximal colon, and 20-70 mM in the distal colon (Cummings J H et al., *Gut*, 28:1221-1227(1987); Nastasi C et al., *Sci Rep-Uk*, 5 (2015)). To examine the effects of microbial byproducts on intestinal epithelial glycosylation, we supplemented cells separately with acetate (C2), lactate (C3), and butyrate (C4) to a final concentration of 10 mM. In total, a significant increase in fucosylated glycans ($p<0.05$) accompanied treatment of Caco-2 cells with each SCFA (FIG. 19). In examining individual glycan compositions, we observed that the consequences of acetate and lactate treatments on Caco-2 were comparable, particularly for branched sialylated structures. Among these, distinguishable glycans include $Hex_6HexNAc_6NeuAc_1$, which increased with treatment (8.1-fold with acetate; 10-fold with lactate), as well as $Hex_6HexNAc_6Fuc_1NeuAc_3$ and $Hex_7HexNAc_7Fuc_1NeuAc_1$, which decreased with treatment (4.7-fold and 2.7-fold, respectively, with acetate; 3.7-fold and 3.4-fold, respectively, with lactate) (FIG. 15A). The changes in sialylated structures produced by butyrate, on the other hand, opposed those produced by acetate and lactate. This contrast is illustrated, for example, in the expression of glycans $Hex_6HexNAc_6NeuAc_1$, $Hex_6HexNAc_5NeuAc_2$, and $Hex_6HexNAc_5Hex_1NeuAc_3$.

Acetate treatment resulted in similar shifts in the HT-29 glycome. However, lactate had minimal effects (FIG. 19). Of the SCFAs, the influence of butyrate was strikingly more dramatic on HT-29 cells than on Caco-2. Upon treatment, fucosylation increased by 262% ($p<0.05$)(FIG. 19). Monofucosylated glycans were among the structures that showed the greatest change (FIG. 15B). Specifically. $Hex_3HexNAc_4Fuc_1$, $Hex_6HexNAc_7Fuc_1$ and $Hex_7HexNAc_7Fuc_1$ each increased more than 13-fold (FIG. 15A). In parallel, di- and trisialylated glycans (e.g., $Hex_6HexNAc_5NeuAc_3$, $Hex_7HexNAc_6NeuAc_2$ and Hex$_6$HexNAc$_5$Fuc$_1$NeuAc$_3$) decreased considerably in abundances in the presence of butyrate (FIG. 15A and 15C).

Non-Carbohydrate Health Supplements Integrate into Glycan Biosynthesis

Figure 16A:
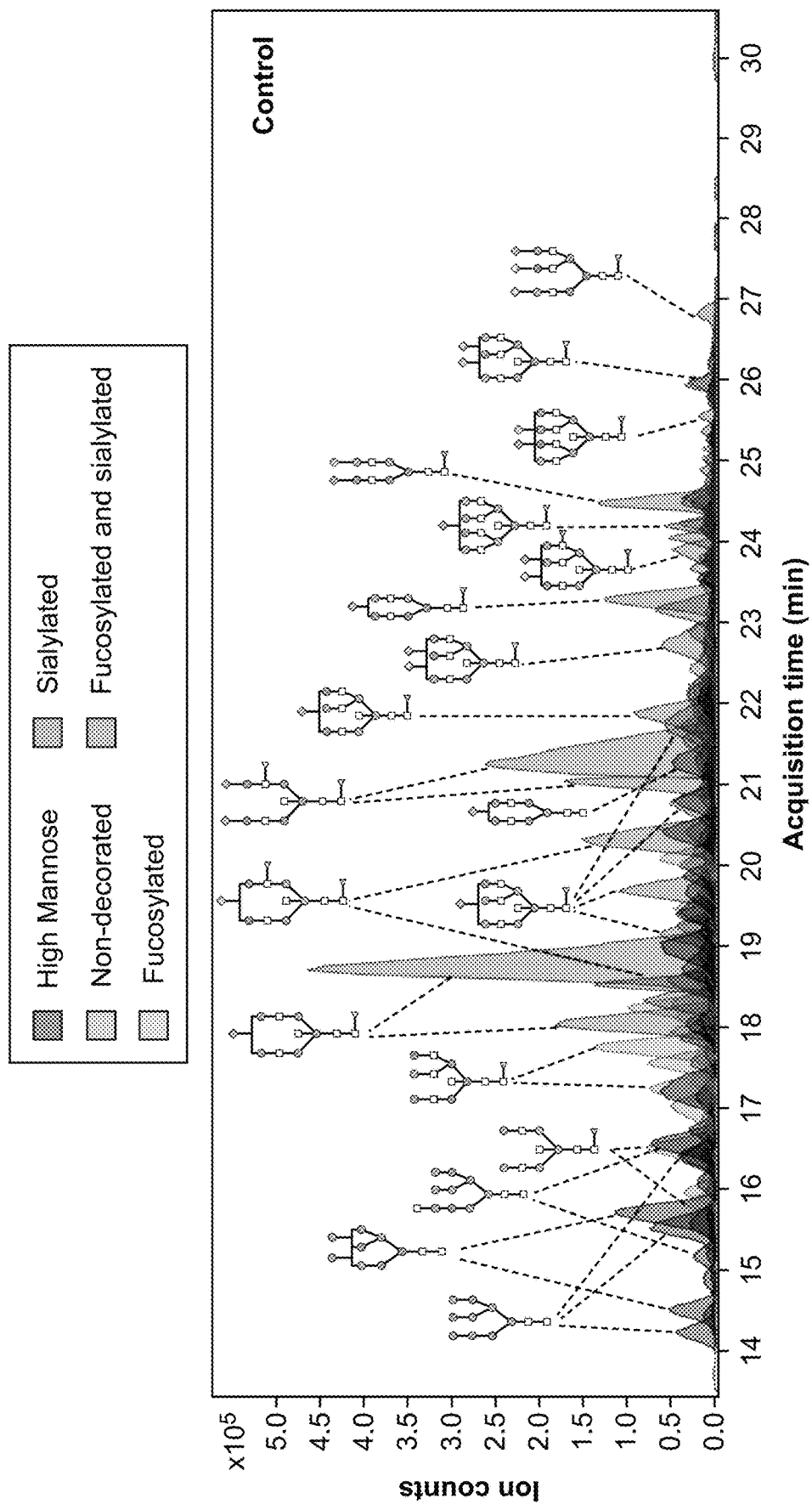
Figure 16B:
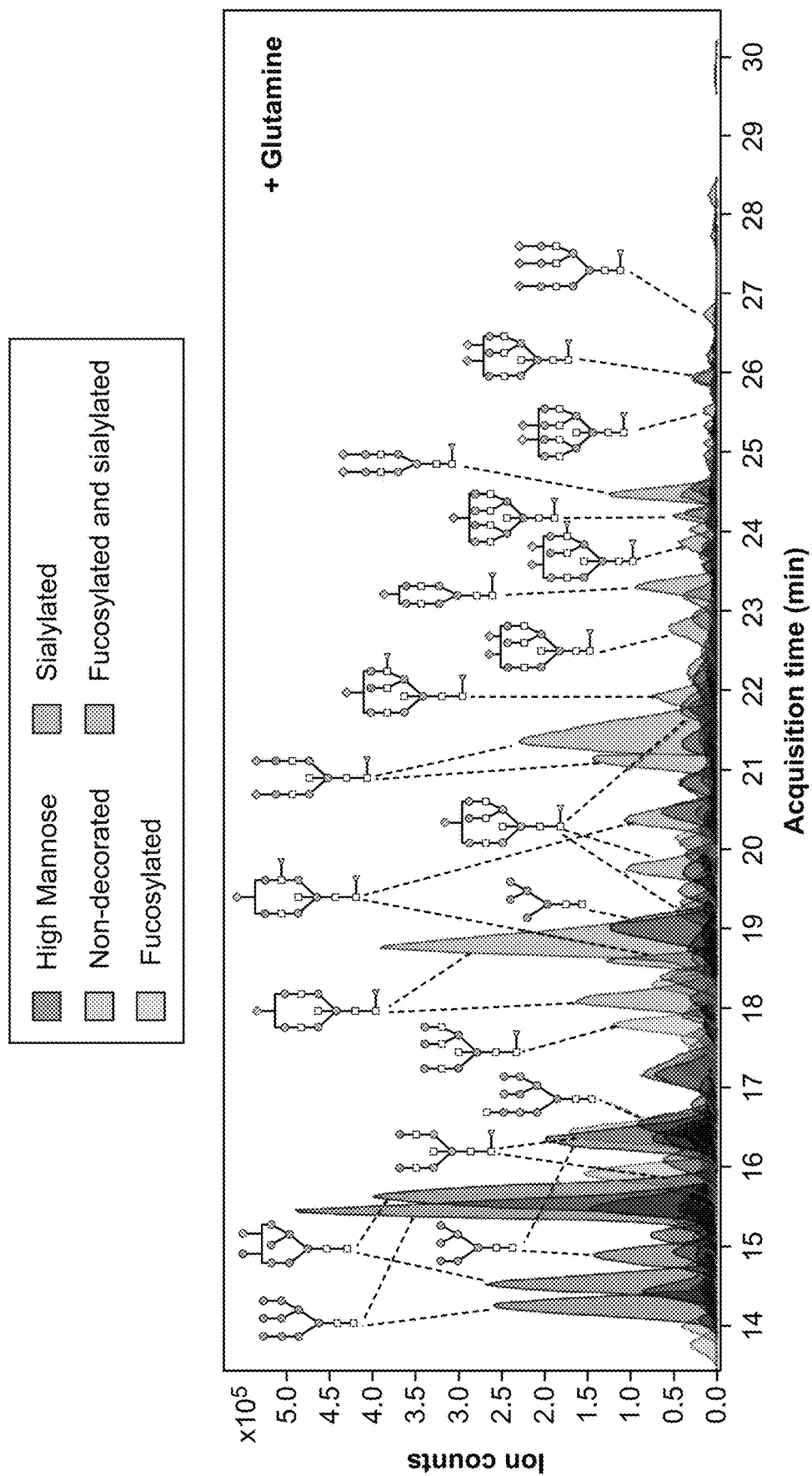

Intestinal epithelial cells can obtain energy from other non-carbohydrate sources. The amino acid $_L$-glutamine is the major bioenergetic substrate necessary for cell proliferation and survival. Additionally, oral and enteral administration of glutamine-rich formulations has been shown to attenuate gut dysfunction and reduce septic morbidity (Klimberg V S et al., *Archive of surgery,* 125:1040-4045 (1990); Vanderhulst RRWJ et al., *Lacet,* 341:1363-1365 (1993)). Glutamine is obligate for cell growth in vitro, usually in concentrations of 2-6 mM. When cells were supplemented with high glutamine (10 mM), significant increases (p<0.05) in high mannose, fucosylated, and nomdecorated complex/hybrid types of glycans were detected in both Caco-2 and HT-29 cells (FIG. 19). Representative chromatograms of identified glycans from Caco-2 cells cultured in normal and high glutamine environments are shown in FIG. 16A and 16B, respectively. According to relative abundances, high mannose type glycan collectively increased by 507% aftertreatment individually, Man 5-Man 9 each increased more than 6-fold (FIG. 15A). In addition, we observed elevation of core-fucosylated glycans Hex$_3$HexNAc$_4$Fuc$_1$, Hex$_6$HexNAc$_4$Fuc$_1$, Hex$_4$HexNAc$_5$Fuc$_1$, and Hex$_5$HexNAc$_5$Fuc$_1$. Contrastingly, larger fucosylated glycans with mom than six HexNAc residues decreased. Sialylated glycans showed remarkable constancy following treatment (FIG. 16A and 16B). According to absolute abundances, the summed abundances of all sialylated glycans in glutamine-treated cells and untreated controls were equal (FIG. 16).

In most cells, an immediate product of glutamine metabolism is glutamate. Uptake of glutamate accordingly correlates with decreased paracellular hyperpermeability and supports the protective effects of glutamine but also serves as an oxidative substrate within enterocytes (Blachier F et al., *The American Journal of clinical nutrition,* 90:814S-821S (2009)). Jejunal luminal content of glutamate was found to change with diet, elevating to as high as 2.6 mM in healthy human volunteers after a protein-rich meal Adibi S A, Mercer D W, *The Journal of clinical investigation,* 52:1586-1594 (1973)). Interestingly, additions of glutamate (2 mM) caused changes in cell, surface glycan expression that were unique to HT-29 but in a manner opposite to the effects of glutamine. In particular, a decline in fucosylation was measured with respect to the control (44.4%, p<0.05), mostly affecting monofucosylated structures (FIG. 19). High mannose glycan expression was unperturbed. Cell surface glycans presented on Caco-2 were relatively unaffected by glutamate treatment.

Another vital contributor to normal gut barrier function is glutathione, a water soluble, thiol-containing tripeptide (Glu-Cys-Gly) with antioxidant activity. It is present intestinal luminal contents at base levels of 0.5 mM, originating chiefly from biliary secretions, but can increase with dietary inclusion, typically at concentrations of 2 mM (Jones D P et al., *Nutrition and cancer,* 17:57-75 (1992)). When we examined the impact of the addition of glutathione (2 mM), the expression levels of the major groups of glycans were essentially unaltered (FIG. 19). Only minor decreases were observed exclusively in complex/hybrid glycans with more than five hexose residues (Hex$_6$HexNAc$_6$Fuc$_1$NeuAc$_3$, Hex$_6$HexNAc$_6$Fuc$_3$NeuAc$_1$, Hex$_5$HexNAc$_3$NeuAc$_1$, and Hex$_5$HexNAc$_4$ on Caco-2; Hex$_6$HexNAc$_7$Fuc$_1$NeuAc$_1$ and Hex$_6$HexNAc$_6$NeuAc$_2$ on HT-29)(FIG. 15A). Such glycosylation changes closely resembled those produced by glutamate. On HT-29, high mannose type glycans increased by 37.1% (p<0.05), an effect

Extracellular Acidification Remodels the Glycome

Figure 16C:
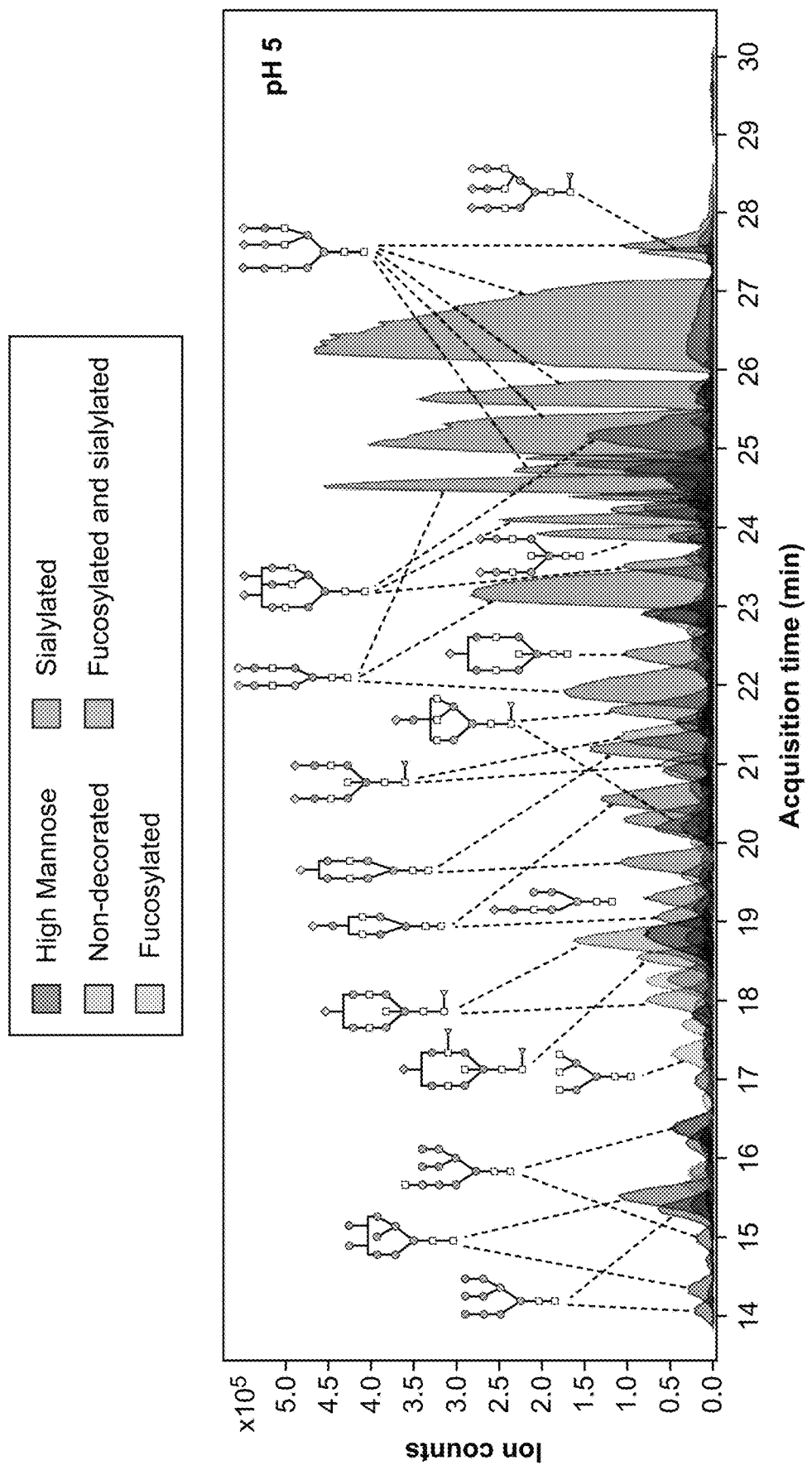
Figure 17A:
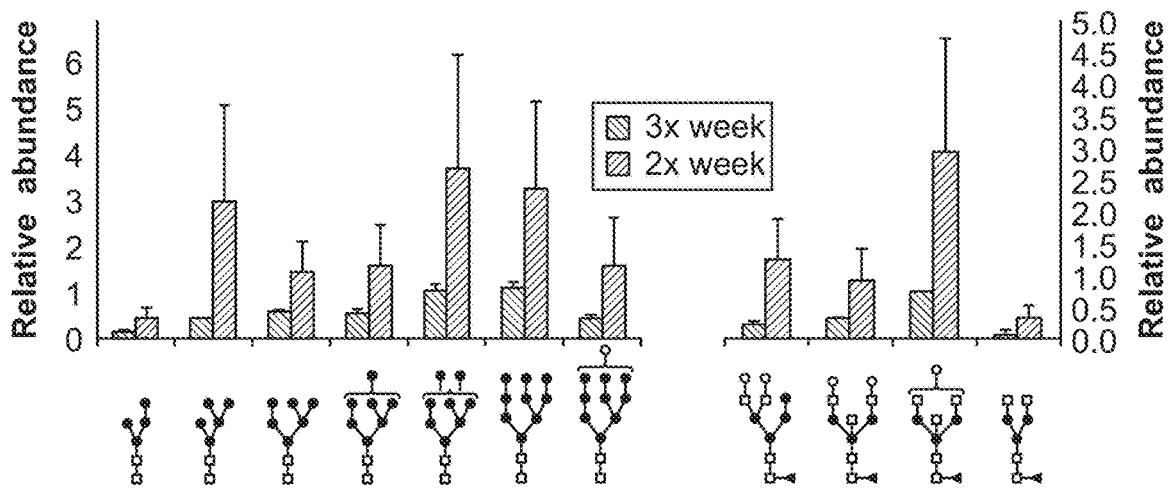
FIG. 17A-C. Effects of growth conditions on cell surface glycans in Caco-2. (A) Increases in abundances in high mannose and fucosylated glycans observed when comparing cells maintained with media renewal twice or three times a week. (B) Fold changes of fucosylated and/or sialylated glycans in cells grown in low pH compared to cells grown in normal media. Glycan notation is as follows: Hex_HexNAc_Puc_NeuAc. (C) Venn diagram indicates the number of glycan compositions identified in cells harvested at passage 16 compared to cells harvested at passage 82. Bar graph represents abundances of glycans from low passage samples that decreased compared to glycans from high passage cells. Monosaccharide symbols follow the SNFG (Symbol Nomenclature for Glycans) system details at NCBI(Varki, A., Cummings, R. D., et al. 2015).
Figure 17B:
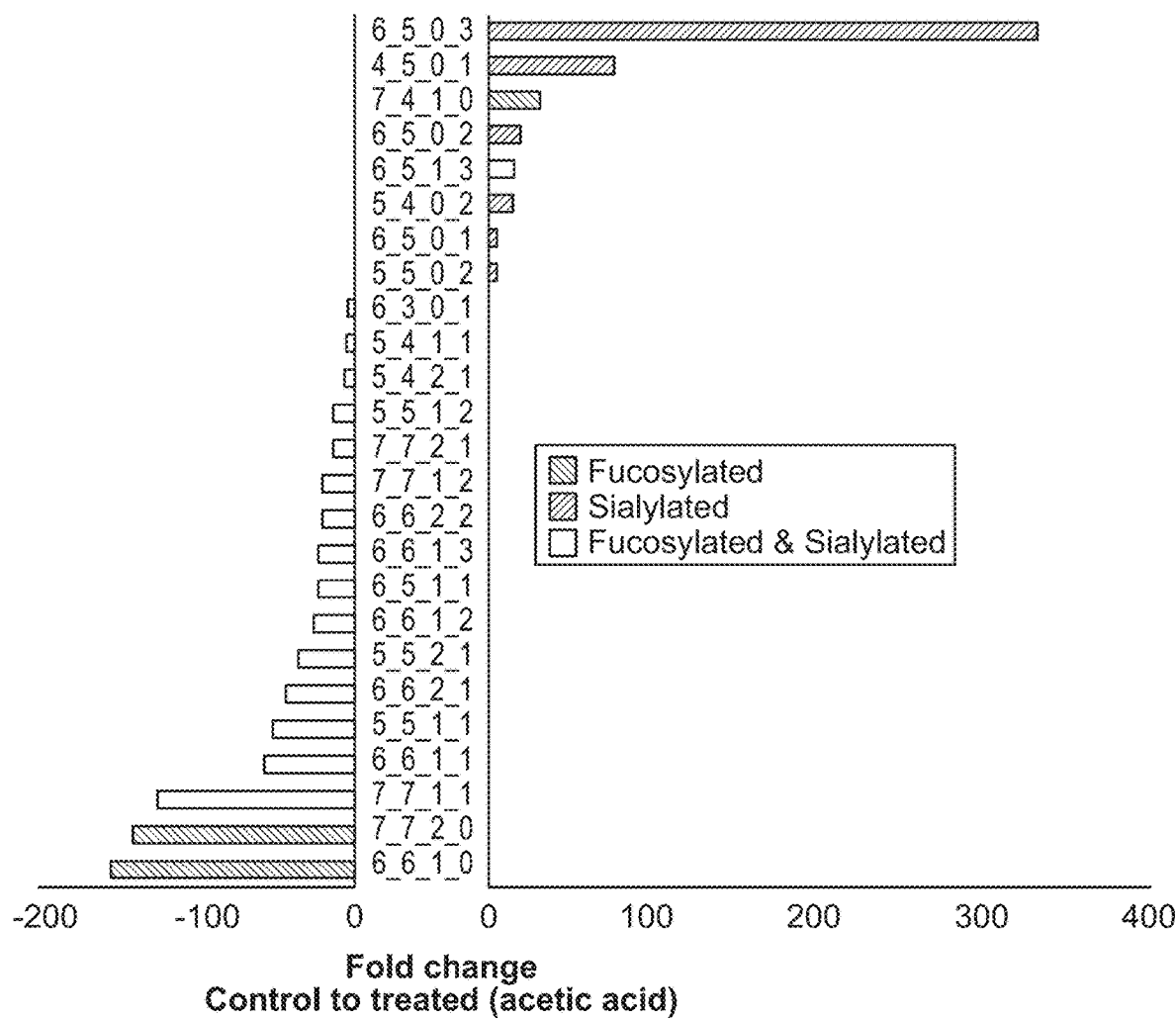

Oscillations in pH can occur when transport or metabolism is challenged. To evaluate the effects of abnormal pH on cell surface glycosylation, we acidified the growing media to a final pH of 4.5-4.6 using acetic acid (pKa 4.75) and sialic acid (pKa 2.6). The profiles of membrane glycans illustrate the striking redistribution toward purely sialylated compounds in cells grown at low pH compared to cells grown at neutral pH (FIGS. 16A and 16C). Interestingly, only a particular subset of sialylated structures was altered. Glycans that showed greater than 3-fold expression changes after addition of acetic acid and sialic acid include mono- or non-fucosylated sialylated structures ranging from one to three sialic acid residues (FIG. 17B). While abundant at acidic pH, these same structures were absent or other wise expressed in minute levels in cells grown in neutral pH. This effect was observed regardless of the acid used to acidify the media. We have previously demonstrated high reproducibility of our method in the detection of sialylated glycans without the need for derivatization (Hua S et al., *The Analyst,* 136:3663-3671(2011); Ruhaak L R et al., *Analytical and bioanalytical chemistry,* 405:4953-4958 (2013)). Verification of glycan identifications was performed using MS/MS

Cell Glycosylation is Sensitive to Growth Conditions

To further understand the causal factors of glycan changes, we evaluated the effects that the growing conditions have on cell surface N-glycosylation. Different environments are created by changes to the components of the growth medium. Caco-2 cell growth is supported in formulations such as Eagle's Minimum Essential Media (EMEM) and Dulbecco's Modified Eagle's Medium (DMEM). However. DMEM contains two to four times the concentration of amino acids (including glutamine), vitamins, ferric nitrate and sodium pyruvate as EMEM, as well as higher amounts of glucose. To evaluate the influence of the basal media on call surface glycosylation, we cultured Caco-2 cells separately in either EMEM or DMEM for the first ten passages and analyzed the N-glycans at passage 11 in triplicates. Generally, DMEM-cultured cells showed significant increases (p<0.05) in fucosylated and non-decorated complex/hybrid type glycans, similar to cells supplemented with 10 mM glutamine. In particular, truncated fucosylated structures (e.g., Hex$_3$HexNAc$_4$Fuc$_1$) showed the most prominent increase. Contrastingly, high mannose type glycans did not increase as they did under-high glutamine conditions. Differences in concentration and composition of the growth media alone led to distinct changes in glycan expression, supporting the observation that membrane glycosylation is impacted by the cell's environment.

Depletions of growth supplies during cell culture have implications on the glycosylation machinery. To account for this factor, Caco-2 cells were grown for at least twelve consecutive passages separately either with media renewal twice or three times a week. In general, glycan samples prepared from Caco-2 cells where media was damaged two times a week showed wider variability between biological replicates than cells where media was changed three times a week (FIG. 17A). Despite the variations, we consistently observed that the level of high mannose type glycans increased up to 6.5-fold with less frequent media changes (FIG. 17A, left panel). Another distinguishing feature between cells was the increase in the abundances of select core fucosylated glycans, Hex$_3$HexNA$_4$Fuc$_1$, Hex$_4$HexNAc$_5$Fuc$_1$, Hex$_5$HexNAc$_5$Fuc$_1$, and Hex$_6$HexNAc$_4$Fuc$_1$ (FIG. 17A, right panel).

Figure 17C:
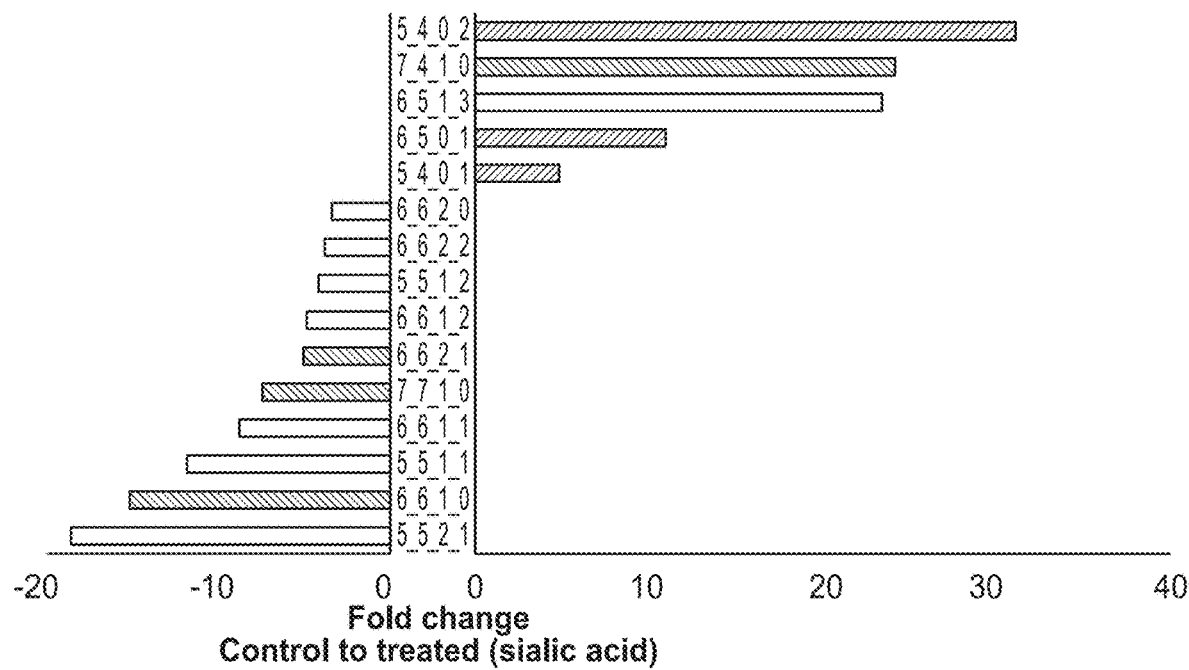
Figure 17C:
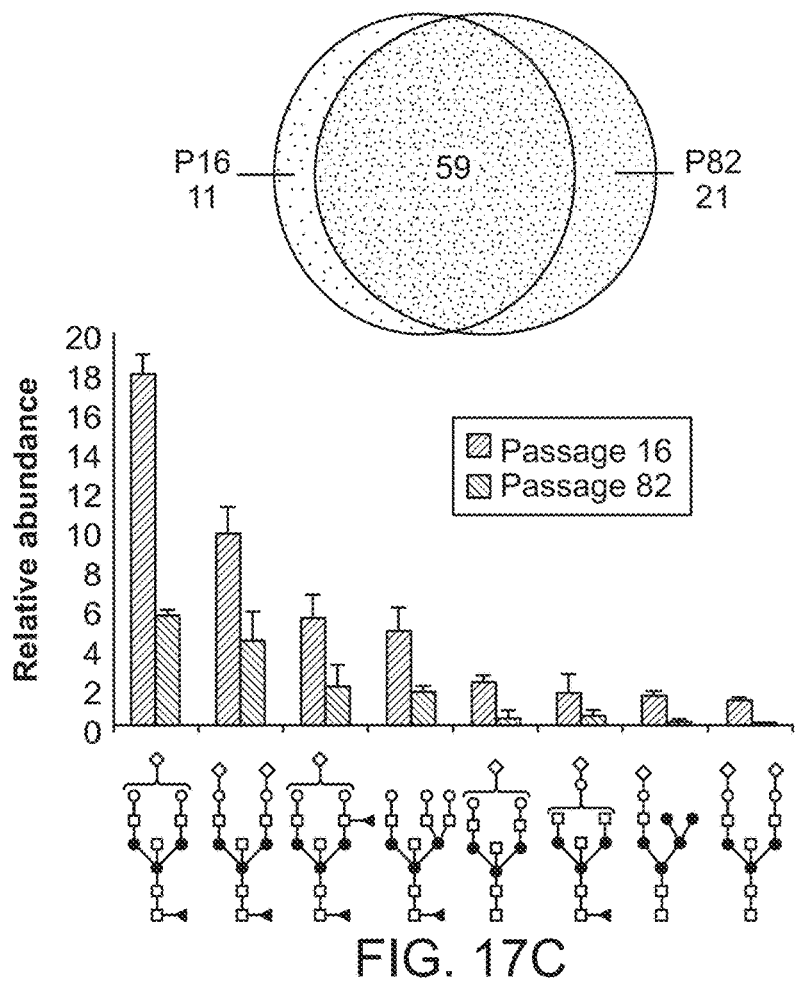

An inherent variability between experiments is passage number, or the number of times cell populations have been subcultured. The use of high passage cells has been reported to obstruct cell proliferation, protein expression, and transcriptional activity (Briske-Anderson M J et al., *Proceedings of the Society for Experimental Biology and Medicine, Society for Experimental Biology and Medicine*, 214:248-257 (1997); Chantret I et al., *Journal of cell science*, 107 (Pt 1):213-225 (1994)). We have previously shown at passages. P10-P47, the glycosylation profile of Caco-2 remains essentially unaltered (Park D et al., *Mol Cell Proteomics*, 14:2910-2921 (2015)). To evaluate the consequences of passage number on cell surface glycosylation, cells subcultured at earlier passages were compared to cells subcultured at later passages (P>80). On average, of the 90 unique compositions identified, low passage and high passage cells shared 59 (65%) of the same glycan compositions (FIG. 17C). Significant decreases of the most abundant complex and hybrid structures were apparent from low to higher passages, including Hex$_5$HexNAc$_5$Fac$_1$NeuAc$_1$, Hex$_5$HexNAc$_5$Fuc$_1$NeuAc$_2$, Hex$_5$HeXNAc$_5$Fuc$_2$NeuAc$_1$, and Hex$_6$HexNAc$_6$Fuc$_1$.

High Mannose Overexpression Shapes Intestinal Cell Membrane Protein Functions

Having established that exogenous factors can significantly alter cell surface N-glycosylation, we then interrogated whether glycan changes affect cell physiology. Due to the recurrent observations of marked changes in high mannose glycans, we examined the functional consequences of selectively increasing their expression levels. For such structure-function correlative studies, exclusivity and biocompatibility are needed. Application of an α-mannosidase I inhibitor, kifunensine, achieved nearly complete conversion into high mannose glycans in Caco-2 without affecting viability. Using this approach, we subsequently analyzed cell responses in untreated and hyper-mannosylated cells.

Epithelial monolayer integrity is ensured by transmembrane tight junction proteins near the apical surface, where differential glycosylation may have fictional influence. Paracellular permeability changes in untreated and kifunensine-treated cells were assessed in vitro by measuring the apical to basal passage of FITC conjugated dextran (FITC-D4). Cells with altered high mannose glycosylation exhibited significantly higher permeability than unaltered cells (FIG. 5A). A dose-dependent effect was observed with kifunensine, which governed the extent of conversion of all surface glycans into high mannose-glycans. Of note, increases in permeability were observed even without complete conversion, at 1 μg/mL treatment. After 2 h, passage of FITC-D4 from the upper to the lower chamber showed a maximum increase of 64% with 100 μg/mL treatment (untreated to treated; p=5.30×10$^{-5}$; n=4). To ensure the integrity of the monolayer, we measured the transepithelial electrical resistance (TEER) before and after shaking, which showed that the transwell movement of FITC-D4 was not due to breaching of the monolayer during treatment.

Figure 18A:
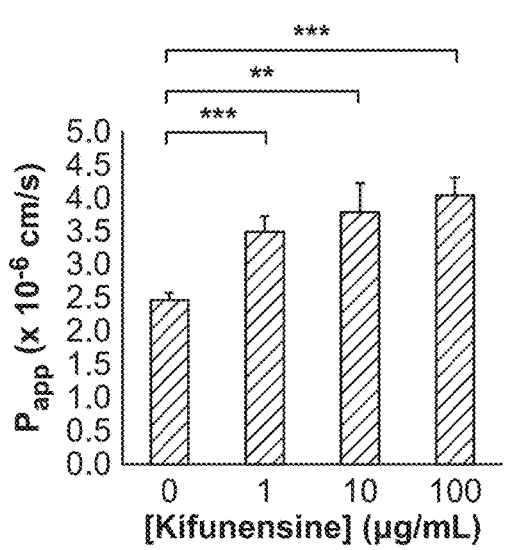
FIG. 18A-C. Functional assays after transformation of cell surface glycans into high manuose type by kifunensine treatment. (A) Intensity of FITC-dextran measured in the basolateral face after passage through cell monolayers. Error bars depict standard deviation (n=4). Asterisks denote statistically significant changes, where p<0.01 and * p<0.001. (B) Comparison of bacterial adhesion and translocation of untreated vs. kifunensine-treated host cells. Asterisks denote statistically significant changes, where *p<0.05 and **p<0.001. (C) Enzymatic activity of IAP and DPPIV in membrane fractions of control and kifunensine-treated cells.
Figure 18B:
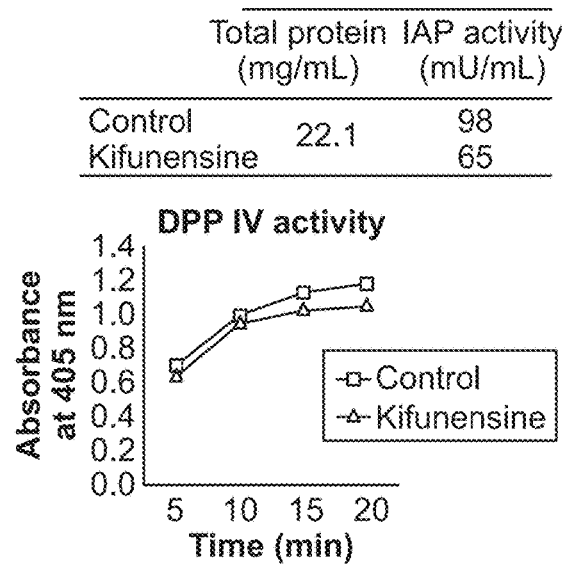
Figure 18C:
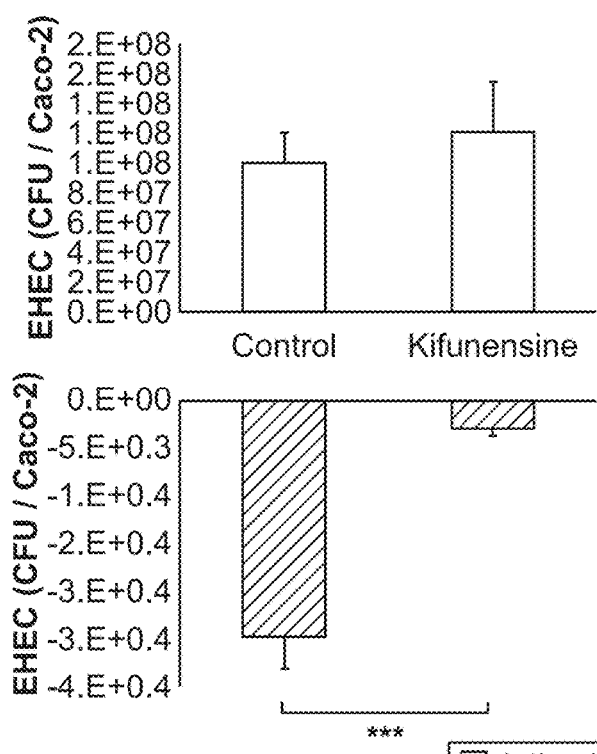
Figure 18C:
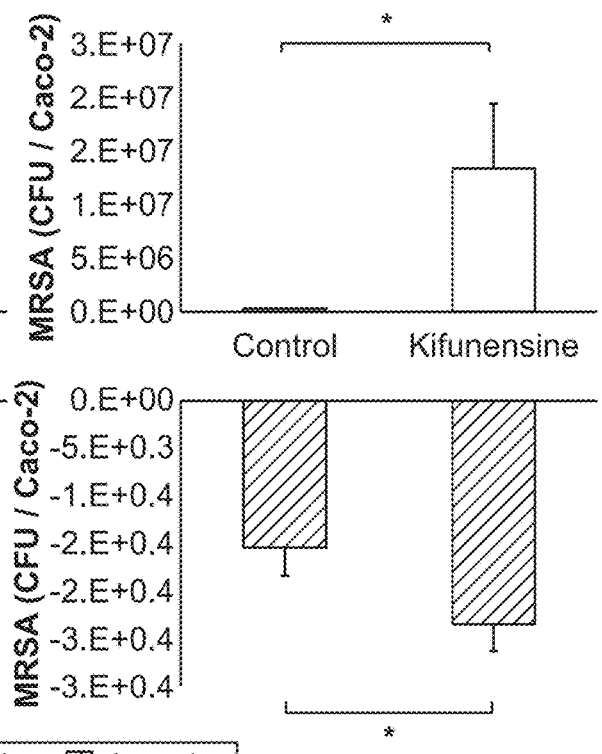

Using comparative proteomic analysis, we and others have determined that key hydrolases associated with brush border formation, including alkaline phosphatase (IAP) and dipeptidyl peptidase IV (DPP IV), are expressed on differentiated Caco-2 cells (Park D et al., *Mol Cell Proteomics*, 14:2910-2921 (2015); Stierum R et al., *Biochimica et biophysica acta*, 1650:73-91(2003)). In this study, remodeled cells were used to examine the correlation between the proteins' glycosylation patterns and their activities. The activity of IAP measured in the enriched membrane fractions of high mannose rich cells showed a significant decrease in activity (~32%) when compared with unaltered Caco-2 cells (FIG. 18B, top panel). In contrast, DPP IV activity was nearly unaffected by kifunensine treatment (FIG. 18B, bottom panel). Furthermore, neither IAP nor DPP IV activity was measured in the cytoplasmic fractions.

Intestinal Cell Glycosylation Modulates the Intensity of Bacterial Infections

The intestinal glycocalyx mediates the first events of contact between the cell and the external environment, particularly against pathogens. We previously showed that high mannose over expression on the host is associated with increased *Salmonella* typhimurium invasion (Park D et al., *Mol Cell Proteomics*, 15:3653-3664 (2016)). To further assess the ability of different bacteria to adhere and penetrate host cells with a typical high mannose glycosylation, we infected unaltered and altered host cells with model gram negative (enterohaemorrhagic *Escherichia coli* (EHEC)) and gram positive (methicillin-resistant *Staphylococcus aureus* (MRSA)) bacterial strains that express a succession of surface proteins and secrete toxins during early encounter. Within 2 h, whereas hyper-mannosylation of Caco-2 did not significantly affect EHEC binding the ability of MRSA to adhere to the monolayer increased substantially (>5000%, p=*0.02) (FIG. 5C). This data suggests that initial attachment of bacteria is orchestrated by the "at present" extracellular N-glycosylation patterns of the host, which we showed can be shaped by dietary and environmental stimuli.

Adhesion and delivery of toxins is followed by bacterial entry into host cells. Both strains were moderately invasive. In comparison to control cells, EHEC uptake was significantly reduced (p=0.0005) in cells that were rich in high mannose glycans as to render the interaction non-invasive. In contrast, approximately 30% more MRSA bacteria were able to invade transformed host cells than untreated cells (p=0:01).

Discussion

We showed by exogenous supplementation that the amounts and types of resources made available to cells influence, heir displayed glycan compositions and abundances. Mono- and disaccharides are common additions to foods and the smallest carbohydrate units of digested material. Although the molecular structures of monosaccharides are similar, we found that the abundance of one over another can guide the synthesis of the final glycosylated products. For example, glucose alone yielded subtle changes on cell surface glycans compared to its epimer, galactose, which induced prominent increases in high mannose type glycans. Survey of the Leloir pathway in the context of galactosemia, a genetic metabolic disorder, has provided detailed insight into galactose metabolism. Gleaning from these studies, surplus galactose may have adverse effects through accumulation of metabolic intermediates or formation of alternate products such as galactitol or galactonate (Lai K et al., *IUBMB life*, 61:1063-1074(2009)), Indeed, due to the closely integrated metabolic routes of monosaccharides, glycosylation changes are likely caused by dysregulation of more than a single pathway. However, by considering each monosaccharide individually, we observed selective responses, which inform our understanding of the precise junctures in the biosynthetic pathway that are regulated by imbalances dietary intake. Intriguingly, while with most monosaccharide additions, we saw an effect on multiple pathways, when we introduced $_L$-fucose, it was not converted into other monosaccharide forms before incorporating onto membrane glycoconjugates, Rather, exogenous fucose primarily affected the expression of select glycan structures that were purely fucosylated. The limited utilization of free fucose by the epithelium may in fact accentuate the beneficial effects of fucose liberation by the gut microbiota (Pickard, J. M., Maurice, C. F., et al. 2014).

Although biosynthesis of N-glycans is regulated by the bioavailability of macronutrients, cells uptake certain metabolites more readily than others. The increased availability of free per-O-acetylated sialic acids did not promote increased expression of sialylated products. Earlier reports on hematopoietic cell sialylation showed that incorporation of sialic acid into glycoproteins occurs from exogenous sources through a putative transporter (Oetke C et al., *European journal of biochemistry/FEBS*, 268:4553-4561 (2001).) Our results show that the efficiency of uptake may be adhered by the presence of acetylation, undoubtedly an important post-glycosylation modification of free sialic acids found in nature (Klein A et al., *Biochimie*, 80:49-57 (1998)). We also note that sialic acids mostly exist as glycosidically linked forms, which may not reflect the fate of free sialic acids, as supported by the analogous but non-identical effects of lactose and galactose treatments. Similarly, we observed low efficiency of glutamate and glutathione metabolism in differentiated Caco-2 cells. Utilization of these compounds likewise may be regulated by the activities of highly specific transporters. Glutamate is negatively charged and requires amino acid transporters that have been reported to be present at low density in the plasma membrane (Newsholme P et al., *Brazilian journal of medical and biological research=Revista brasileria de pesquisas medicas e biologicas*, 36:153-163 (2003)). Glutathione is absorbed intact through a specialized transport system separate from the intestinal peptide transport system.

Excess fructose consumption has been linked with chronic diseases and contributes to inflammation (Brymora A et al., *Nephrology, dialysis, transplantation: official publication of the European Dialysis and Transplant Association-European Renal Association*, 27:608-612 (2012)). Our results suggest that the detrimental effects of fructose on the intestinal epithelial monolayer may be intensified by increased high mannose production. High mannose type glycans, assembled during the earlier steps of glycosylation, are minimally processed. Therefore, higher production may be dictated by factors related to post-glycosylation trafficking, including impaired ability of proteins to recycle through the trans-Golgi network (Parry S et. al., *Gycobiology*, 16:623-634(2006)). It is not able that both cell lines exhibited similar responses in the supplementation studies. However, cases where their responses were dissimilar indicate that utilization and metabolism of dietary substances are cell-dependent. HT-29, as a partially differentiated type, generally showed less intense changes in its glycome than Caco-2. Currently studies are ongoing to track the incorporation of monosaccharides from external sources into cell- and tissue-specific biomolecules for examining nutrient distribution.

Like glucose, glutamine contributes heavily to multiple fundamental metabolic mechanisms in proliferating cells as a source of γ-nitrogen (as in hexosamine synthesis (Orlando R et al., *Journal of proleome research*, 8:3816-3823(2009))), α-nitrogen, and carbon backbone (DeBerardinis R J, Cheng T., *Oncogene*, 29:313-324 (2610)). Accordingly, we examined the metabolic fate of glutamine in support of complex type N-glycan production bearing aminosugars GlcNAc and NeuAc. On the contrary, at high concentrations of supplementary glutamine, we primarily observed several fold increases in the levels of high mannose glycans. Gut mucosal barrier is dependent on steady levels of glutamine (De-Souza D A, Greene L J., *Critical care medicine*, 33:1125-1135(2005); Souba W W et al., *The Journal of surgical research*, 48:383-391 (1990); van der Hulst R. R et al., *Lancet*, 341:13.63-1365 (1993)). Absorption of glutainein excess may provoke cells to be in a more basic environment due to the generation of ammonia during the degradation of glutamine, leading to more high mannose glycans on the surface.

An increasing number of studies describe the beneficial roles of short chain fatty acids in barrier function, energy metabolism, and immune modulation (Correa-Oliveira R et al., *Clinical & translational immunology*, 5;e73 (2016); den Besten G et al., *Journal of lipid research*, 54:2325-2340 (2013); Wong J M et al., *Journal of clinical gastroenterology*, 40:235-243 (2006)). In the presence of low millimolar concentrations of SCFAs, Caco-2 and HT-29 cells responded similarly in favor of fucose-containing glycans. The induced increase of intestinal epithelial cell fucosylation points to the potential role of SCFAs in maintaining host-commensal symbiosis and supporting host defense against pathogens (Goto Y et al., *Science*, 345:1254009 (2014); Pickard J M et al., *Nature*, 514:638.641 (2014)). Additionally, we observed that varying lengths of SCFAs have different intensity of effects on cellular glycosylation, which has implications where microbial communities and SCFA distribution differ along the length of the intestines.

Intraluminal pH is adjusted by many factors such as diet, microbial byproducts, and disease (Fallingborg J et al., *Danish medical bulletin*, 46:183-196 (1999); Ovesen L et al., *Gastroenterology*, 90:958-962 (1986); Ovesen, L., Bendtsen, F., et al., 1986; Pye G et al., *Gut*, 31:1355-1357 (1990)). Often, these factors are associated with lowering the pH. In this study, we showed that sialylated glycans dominate the surface of intestinal epithelial cells at acidic pH, which is supported by the likely enhancement of sialyltransferase activity over other glycosyltransferases (Gawlitzek M et al., *Biotechnol Bioeng*, 68:637-646 (200); Ha T K, Lee G M., *J Biotechnol*, 180:23-29 (2014)). Acidic extracellular environments have been reported to induce physiological changes such as integrin activation and metastasis (Kato Y et al., *Cancer Cell Int*, 13 (2013); Paradise R K et al., *PloS one*, 6:e15746 (2011); Rofstad E K. et al., *Cancer research*, 66:6699-6707(2006)), Based on our findings, hyper-sialylation of proteins may be a key contributor that governs these behaviors.

The impact of glycosylation on membrane functions was evident upon transforming Caco-2 cells, which natively exhibit high levels of sialylation, into high mannose-rich cells using kifunensine. Paracellular permeability, known to be governed by tight junction proteins, was instantly impaired despite the extent of conversion. IAP showed a decline in activity after maximal high mannose conversion whereas DPP IV activity remained unaltered. As expected, glycan changes affect individual apical plasma membrane proteins differently. Two potential explanations are proposed: (1) Abnormal protein glycosylation results in impaired transport to the cell surface; (2) Uniform conversion to high mannose glycosylation contribute to unsuitable protein conformations such that its functional properties are greatly reduced or lost. Loss-of-glycosylation studies have implied that a fundamental relationship exists between protein functions and proper glycosylation but often lack protein-specific information. Continuing efforts are concentrated on isolating intact glycoforms to selectively monitor individual glycoproteins and glycosites. Importantly, the consequences of glycan changes are not only observed in the cell itself but extracellularly, in the strength of bacterial interactions.

Our analysis provides details of glycomic changes induced by dietary and microbial compounds and shows that Caco-2 and HT-29 membrane glycosylation is a sensitive sensor of the cell's extracellular environment. The methods described here can be used for screening the effects of a variety of environmental changes. Cell models have limitations in that that they do not simulate the composition of the normal intestinal monolayer, which contains more than one cell type, and lack a fully formed mucus layer to separate the epithelial cell layer from the luminal content. Further progress is being made to determine whether intestinal glycosylation can be shaped by dietary supplements in vivo and whether such glycan changes contribute to gastrointestinal disturbances. Understanding the causes and effects of glycan changes has the potential to provide therapeutic strategies to strengthen barrier function by controlling local glycosylation.

CONCLUSION

Elements that affect the cell's intricate glycosylation pathway need to be further evaluated. The impact of cell growth conditions is dependent on a number of determinants such as cell type, origin, species, etc. In the gut, environmental conditions can quickly vary with metabolite concentrations, pH, and colonizing microbe communities. This study explores the types of environments that cause changes to the glycosylation patterns of intestinal epithelial cells. We demonstrate that unchecked dietary and bioenergetic supplements cause irregular glycosylation to occur, which indeed cause penalties to the functions and integrity of cells. These results facilitate the translation of analytical tools into physiological systems and progress toward the development of improved glycosylated products by programmed changes to relevant parameters during cell growth.

Materials and Methods

Cell Culture

Human colorectal adenocarcinoma Caco-2 cells derived from a Caucasian male 72 years of age, were obtained from American Type Culture Collection (ATCC, VA) and grown in Eagle's Minimum Essential Medium (EMEM) supplemented with non-essential amino acids, 2 mM $_L$-glutamine, 10% (v/v) fetal bovine serum (Life Technologies, NY), 1 mM sodium pyruvate, 1.5 g/L sodium bicarbonate, 100 U/mL penicillin, and 100 µg/mL streptomycin. Alternatively, Caco-2 cells were grown in Dulbecco's Modified Eagle's Medium (DMEM) supplemented with 10% (v/v) fetal bovine serum, 100 U/mL penicillin, and 100 µg/mL streptomycin. Human colorectal adenocarcinoma HT-29 cells, derived from a Caucasian female 44 years of age, were obtained from ATCC and grown in McCoy's 5A medium supplemented with 10% (v/v) fetal bovine serum, 100 U/mL penicillin, and 100 µg/mL streptomycin. Cells were subcultured at 80% confluency and maintained at 37° C. in a humidified incubator with 5% $CO_{=2}$. All treatments were added to the media after cell differentiation. Caco-2 cells were fully differentiated 14-days post-confluency. HT-29 cells were partially differentiated 4-days post-confluency. After 72 h, cells were collected in biological triplicates by scraping A fixed count of $2\times10^6$ viable cells was used for each experiment Passage number between experiments was controlled to no higher than P40 and a delta P of no more than 20. High passage cells were scraped after P80. Media was renewed three times a week unless specified. Monolayer integrity and quality of cell borders were evaluated under the microscope routinely during growth and before harvest.

Enterohaemorrhagic *Escherichia coli* O157H;7 (EHEC) and methicillin-resistant *Staphyloccuus aureus* (MRSA) were grown at 37° C. with continuous shaking for 14-16 h.
Permeability Assay Caco-2 cells were seeded on porous polycarbonate filter membranes (3401; Corning, NY) until cells formed a single monolayer and were fully differentiated. Kifunensine (Carbosynth, CA) was added post-differeniation for 72 h. Four replicates were prepared for both control and kifunensine-treated cases. Permeability experiments were performed in Hank's Balanced Salt Solution, prepared with 25 mM HEPES, 0.35 g/L sodium bicarbonate, and adjusted to pH 7.4 with sodium hydroxide. The prepared membranes were washed and inserted into a new micro-well plate. FITC-dextran (4 kDa) (Sigma-Aldrich, MO) was introduced to the upper (apical) chamber at 10 mg/mL. The plate was placed in a 37° C. incubator devoid of $CO_2$ for 2 h on an orbital shaker at 100 rpm. The amount of FITC-dextran that transferred through the cells was measured in the lower (basolateral) chamber by fluorescence at 492/520 nm (excitation/emission) using a Perkin Elmer Victor3 Multilabel Plate Reader (Parkin Elmer, MA). The apparent permeability coefficient was determined according to the following equation:

$$P_{app} = \frac{dQ/dt}{AC_0}$$

where dQ/dt is the rate of permeation across cells, A is the surface area of the membrane, and $C_0$ is the initial donor concentration. Transepithelial electrical resistance (TEER) values were measured using a Millicell ERS Voltohmmeter (EMD Millipore, MA) at room temperature.
Enzyme Activity Assay Intestinal alkaline phosphatase (IAP) activity was measured in membrane-enriched factions using a colorimetric assay per manufacturer's instructions (Abcam, MA). Cells were incubated with 50 µM p-nitrophenyl phosphate (p-NPP) for 60 min. Dephosphorylated was monitored by the production of p-nitrophenyl, which turns the solution to a visible yellow color. Absorbance readings were taken at 405 nm with a microplate photometer. Enzyme activities were determined with a standard curve generated using IAP enzyme. Activity was measured in U/mL, where a Unit is defined as the amount of enzyme to hydrolyze 1 µmol of p-NPP per minute at 37° C.

Dipeptidyl peptidase IV (DPP IV) activity was measured in membrane-enriched fractions using a colorimetric assay per manufacturer's instructions (Enzo Life sciences, NY). Membrane extracts from control and kifunensine-treated cells were incubated with a chromogenic substrate (H-Gly-Pro-pNa) at 25° C. for 30 min. Cleavage of p-nitroaniline (pNA) was monitored by absorbance measurements at 405 am with a microplate photometer. Enzyme activities were compared to a standard curve generated using a pNA standard. A reaction containing a DPP IV inhibitor (P32/98) was included as a control for enzymatic specificity.
Bacterial Association Assay Caco-2 cells were seeded into 24-well plates at $5\times10^5$ cells per well. Wells were designated as control (Row 1) or treated with kifunensine (Row 2). For adhesion, the left half of the plate was infected with logarithmically growing enterohaemorrhagic *Escherichia coli* O157:H7 (EHEC), and the right half of the plate was infected with methicillin-resistant *Staphylocaccus aureus* (MRSA). Triplicate setups were prepared for each condition. After 2 h, the wells were washed 3× with PBS and the adherent cell counts were determined by serial dilutions and spotting of the lysate generated upon treatment of the wells with, PBS/0.5% Triton for 5 min. CFU are expressed per mL as a comparison between the different treatments. For measuring uptake, the duplicate plate was similarly infected with EHEC and MRSA. Two hours post-infection, the unbound bacteria were washed with PBS (3×) and the Caco-2-cells were treated with media containing 100 µg/mL gentamicin to lyse cell surface associated bacteria. Following a 2 h-treatment, the internalized bacterial cell counts were derived upon lysing the Caco-2 cells with PBS/0.5% Triton followed by serial dilution and CFU counts.

Cell Membrane Extraction

Extraction of the cell membrane compartment was performed as described previously with modified procedures (An H J et al., *Mol Cell Proteomics*, 11:M1.1101066V (2012)). In brief harvested cells were resuspended in homogenization buffer containing 0.25 M sucrose, 20 mM HEPES-KOH (pH 7.4), and 1:100 protease inhibitor (EMD Millipore, CA). Cell lysis was performed on ice using a probe sonicator (Qsonica, CT) with five alternating and on and off pulses in 5 and 10 s intervals, respectively. Lysates were certified at 2,000×g for 10 min to remove the nuclear fraction and cellular debris. The supernatant was collected and brought to 1 mL with homogenization buffer for ultracentrifugation at 200,000×g for 45 min at 4° C. The pallet was resuspended and repelleted by ultracentrifugation in 0.2 M Na$_2$CO$_3$ (pH 11) followed by water to fragment the endoplasmic reticulum and remove the cytoplasmic fraction, respectively. The resulting membrane faction was isolated and stored at −20° C. until further processing.

Enzymatic Release and Enrichment of N-Glycans

Membrane pellets were resuspended with 100 µL of 100 mM ammonium bicarbonate in 5 mM dithiothreitol and heated for 10 s at 100° C. to thermally denature the proteins. To cleave N-glycans from membrane proteins, 2 µL of peptide N-glycosidase F (New England Biolabs, MA) were added to the samples and incubated at 37° C. in a microwave reactor (CEM Corporation, NC) for 10 min at 20 watts. After addition of 400 µL of chilled ethanol, samples were placed in −80° C. for 1.5 h and centrifuged for 20 min at 21,130×g to precipitate residual deglycosylated proteins. The supernatant containing the released N-glycans was collected and dried. N-Glycans were purified by solid phase extraction containing a porous graphitized carbon (PGC) matrix. Eluted fractions were dried in vacuo.

Mass Spectrometric Analysis

Glycan samples were reconstituted in nanopure water for analysis using an Agilent nanoLC/ESI-QTOF-MS system (Agilent Technologies, CA) Samples were introduced into the MS with a microfluidic chip, which consists of enrichment and analytical columns packed with porous graphitized carbon and a nanoelectrospray tip. A binary gradient was applied to separate and elute glycans at a flow rate of 0.4 µL/min: (A)3% (v/v) acetonitrile and 0.1% (v/v) formic acid in water and (B) 90% (v/v)acetonitrile in 1% (v/v) formic acid in water. MS spectra were acquired at 1.5 s per spectrum over a mass range of m/s 600-2000 in positive ionization mode. Mass inaccuracies were corrected with reference mass m/z 1221.991.

Collision-induced dissociation (CD) was performed with nitrogen gas using a series of collision energies ($V_{collision}$) dependent on the m/z values of the N-glycans, based on the equation:

$$V_{collision} = \text{slope}(m/z) + \text{offset},$$

where the slope and offset were set at (1.8/8100 Da) V and −2.4 V, respectively.

Data Analysis

N-Glycan compounds were identified with an in-house retrosynthetic library of all possible glycan compositions according to accurate mass (Kronewitter S R et al., *Proteomics*, 9:2986-2994 (2009)). Subtypes including high mannose, complex and hybrid were grouped accordingly by knowledge of die mammalian N-glycan biosynthetic pathway. Quantitative reproducibility and tandem MS confirmation of library matches were previously validated, enabling rapid and accurate assignment of glycan compounds (Hus S et al., *The Analyst*, 136:3663-3671 (2011); Ruhaak L R et al., *Analytical chemistry*, 84:396-402 (2012)). Signals above a signal-to-noise ratio of 5.0 were filtered and deconvoluted using MassHunter Qualitative Analysis B.06.01 (Agilent Technologies, CA). Deconvoluted masses were compared to theoretical masses using a mass tolerance of 20 ppm and a false discovery rate of 0.6%. Area under the peak was used to represent the data. Relative abundances were determined by integrating ion counts for observed glycan masses and normalizing to the summed ion counts of all glycans detected. Statistical evaluation of significant glycan abundance changes was performed using an unpaired, two-tailed Student's t-test. Structures that were not observed in two of three replicates were excluded in the analysis.

In the claims appended hereto, the term "comprise" and variations thereof such as "comprises" and "comprising" when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of improving high density lipoprotein (HDL) immunomodulatory function in a human in need thereof, the method comprising, administering a sufficient amount of monosaccharides selected from at least one or more of galactose, fructose, fucose, or N-acetyl glucosamine to improve HDL immunomodulatory function in the human, wherein before the administering the human has HDLs having levels of glycosylation of one or more specific proteins indicative of reduced HDL immunomodulatory function compared to healthy humans and wherein the administering improves HDL immunomodulatory function, wherein the specific proteins and their levels of glycosylation indicative of reduced HDL immunomodulatory function are as shown in Table 1 and are selected from at least one of:

ApoC-III,
Mono-sialylated ApoC-III,
ApoC-III_74_2221,
Non-sialylated alpha-2HS-glycoprotein (A2HSG), Di-sialylated A2HSG,
A2HSG_O_346_2200,
A2HSG_176_5402,
alpha-1-antitrypsin (A1AT),
A1AT_70_5402,
A1AT_271_5402,
A1AT_70_5412,
A1AT_107_5412, or
A1AT_271_5412.

2. The method of claim 1, further comprising before the administering, obtaining an HDL sample from the human and detecting the level of glycosylation of at least one or more of the specific proteins.

3. The method of claim 1, wherein after the administering, obtaining an HDL sample from the human and detecting the level of glycosylation of at least one or more of the specific proteins.

4. The method of claim 2, wherein the detecting comprises detecting the level of glycosylation of:
   (i) ApoC-III,
      mono-sialylatd ApoC-III, and
      ApoC-III_74_2221; or
   (ii) A1AT, and
      di-sialylated A1AT; or
   (iii) non-sialylated A2HSG, and
      A2HSG_O_346_2200, and
      di-sialylated A2HSG, and
      A2HSG_176_5402.

5. The method of claim 2, wherein the detecting comprises binding the specific protein in the sample with a binding reagent that specifically binds the specific protein or an oligosaccharide thereon, wherein the binding agent is a lectin or an antibody.

6. The method of claim 5, wherein the detecting comprises mass spectrometry or liquid chromatography.

7. The method of claim 1, wherein the monosaccharide is galactose.

8. The method of claim 1, wherein the monosaccharide is fructose.

9. The method of claim 1, wherein the monosaccharide is fucose.

10. The method of claim 1, wherein the monosaccharide is N-acetyl glucosamine.

11. The method of claim 1, wherein the specific protein is at least ApoC-III.

12. The method of claim 1, wherein the specific protein is at least Mono-sialylated ApoC-III.

13. The method of claim 1, wherein the specific protein is at least ApoC-III_74_2221.

14. The method of claim 1, wherein the specific protein is at least non-sialylated alpha-2HS-glycoprotein (A2HSG).

15. The method of claim 1, wherein the specific protein is at least di-sialylated alpha-2HS-glycoprotein (A2HSG).

16. The method of claim 1, wherein the specific protein is at least A2HSG_O_346_2200.

17. The method of claim 1, wherein the specific protein is at least A2HSG_176_5402.

18. The method of claim 1, wherein the specific protein is at least alpha-1-antitrypsin (A1AT).

19. The method of claim 1, wherein the specific protein is at least A1AT_70_5402.

20. The method of claim 1, wherein the specific protein is at least A1AT_271_5402.

21. The method of claim 1, wherein the specific protein is at least A1AT_271_5402.

22. The method of claim 1, wherein the specific protein is at least A1AT_70_5412.

23. The method of claim 1, wherein the specific protein is at least A1AT_107_5412.

24. The method of claim 1, wherein the specific protein is at least A1AT_271_5412.

* * * * *